(12) United States Patent
Tachibana et al.

(10) Patent No.: US 11,022,882 B2
(45) Date of Patent: Jun. 1, 2021

(54) COMPOUND AND COMPOSITION FOR FORMING ORGANIC FILM

(71) Applicants: SHIN-ETSU CHEMICAL CO., LTD., Tokyo (JP); INTERNATIONAL BUSINESS MACHINES CORPORATION, Armonk, NY (US)

(72) Inventors: Seiichiro Tachibana, Joetsu (JP); Takeru Watanabe, Joetsu (JP); Keisuke Niida, Joetsu (JP); Hiroko Nagai, Joetsu (JP); Takashi Sawamura, Joetsu (JP); Tsutomu Ogihara, Joetsu (JP); Alexander Edward Hess, San Jose, CA (US); Gregory Breyta, San Jose, CA (US); Daniel Paul Sanders, San Jose, CA (US); Rudy J. Wojtecki, San Jose, CA (US)

(73) Assignees: SHIN-ETSU CHEMICAL CO., LTD., Tokyo (JP); INTERNATIONAL BUSINESS MACHINES CORPORATION, Armonk, NY (US)

( * ) Notice: Subject to any disclaimer, the term of this patent is extended or adjusted under 35 U.S.C. 154(b) by 146 days.

(21) Appl. No.: 16/013,728

(22) Filed: Jun. 20, 2018

(65) Prior Publication Data

US 2019/0391493 A1 Dec. 26, 2019

(51) Int. Cl.
| | | |
|---|---|---|
| G03F 7/025 | (2006.01) | |
| C07C 13/54 | (2006.01) | |
| C07C 43/23 | (2006.01) | |
| G03F 7/039 | (2006.01) | |
| C08K 5/00 | (2006.01) | |
| C08L 49/00 | (2006.01) | |
| H01L 21/027 | (2006.01) | |
| H01L 21/308 | (2006.01) | |

(52) U.S. Cl.
CPC .......... *G03F 7/0392* (2013.01); *C07C 13/54* (2013.01); *C07C 43/23* (2013.01); *C08K 5/0016* (2013.01); *C08K 5/0025* (2013.01); *C08L 49/00* (2013.01); *G03F 7/025* (2013.01); *C08L 2203/16* (2013.01); *C08L 2203/20* (2013.01); *H01L 21/0274* (2013.01); *H01L 21/3081* (2013.01)

(58) Field of Classification Search
CPC .. C07D 335/10; C07D 311/80; C07D 491/04; C07D 221/06; C07D 495/04; C07C 43/23; C07C 43/215; C07C 2603/18; C07C 13/54; C08L 49/00; C08L 2203/16; C08L 2203/20; C08K 5/0016; C08K 5/0025; G03F 7/025
See application file for complete search history.

(56) References Cited

U.S. PATENT DOCUMENTS

| | | | | |
|---|---|---|---|---|
| 3,819,654 | A | * | 6/1974 | Pfister et al. ........ C07D 311/86 549/393 |
| 7,319,151 | B1 | * | 1/2008 | Tan ....................... C07D 277/66 548/152 |
| 9,261,788 | B2 | | 2/2016 | Tachibana et al. |
| 9,281,207 | B2 | | 3/2016 | Stowers et al. |
| 10,444,628 | B2 | * | 10/2019 | Kori ........................ C07C 49/653 |
| 2002/0106909 | A1 | | 8/2002 | Kato et al. |
| 2005/0255712 | A1 | | 11/2005 | Kato et al. |
| 2006/0019195 | A1 | | 1/2006 | Hatakeyama et al. |
| 2006/0204891 | A1 | | 9/2006 | Hatakeyama |
| 2009/0274978 | A1 | | 11/2009 | Ohashi et al. |
| 2010/0099044 | A1 | | 4/2010 | Hatakeyama et al. |
| 2012/0252218 | A1 | | 10/2012 | Kori et al. |
| 2013/0189533 | A1 | | 7/2013 | Okuyama et al. |

(Continued)

FOREIGN PATENT DOCUMENTS

| | | |
|---|---|---|
| JP | 2002-334869 A | 11/2002 |
| JP | 2005-128509 A | 5/2005 |

(Continued)

OTHER PUBLICATIONS

Berscheid et al., "Concave dyestuffs: A triply bridged triphenylmethyl dication", Synth vol. 1992(01/02) pp. 58-62 (Jan. 2, 1992).*

(Continued)

*Primary Examiner* — Martin J Angebranndt
(74) *Attorney, Agent, or Firm* — Oliff PLC

(57) ABSTRACT

A compound shown by the following general formula (1-1),

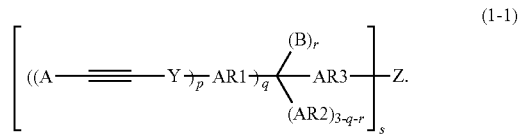

AR1 and AR2 each independently represent an aromatic ring or an aromatic ring containing at least one nitrogen and/or sulfur atom, two AR1s, AR1 and AR2, or two AR2s are optionally bonded; AR3 represents a benzene, naphthalene, thiophene, pyridine, or diazine ring; A represents an organic group; B represents an anionic leaving group; Y represents a divalent organic group; "p" is 1 or 2; "q" is 1 or 2; "r" is 0 or 1; "s" is 2 to 4; when s=2, Z represents a single bond, divalent atom, or divalent organic group; and when s=3 or 4, Z represents a trivalent or quadrivalent atom or organic group. This compound cures to form an organic film, and also forms an organic under layer film.

3 Claims, 3 Drawing Sheets

(56) References Cited

U.S. PATENT DOCUMENTS

| | | | |
|---|---|---|---|
| 2013/0302990 A1 | 11/2013 | Watanabe et al. | |
| 2013/0310514 A1 | 11/2013 | Minegishi et al. | |
| 2014/0342273 A1* | 11/2014 | Kim | G03F 7/094 430/5 |
| 2016/0085152 A1 | 3/2016 | Nakafuji et al. | |
| 2016/0111287 A1 | 4/2016 | Hatakeyama et al. | |
| 2017/0015779 A1 | 1/2017 | Jung et al. | |
| 2017/0018436 A1 | 1/2017 | Hatakeyama et al. | |
| 2017/0183531 A1* | 6/2017 | Kori | C09D 155/00 |
| 2017/0184968 A1 | 6/2017 | Kori et al. | |
| 2017/0199457 A1 | 7/2017 | Hatakeyama et al. | |
| 2019/0390000 A1* | 12/2019 | Tachibana | C07D 335/10 |

FOREIGN PATENT DOCUMENTS

| | | | | |
|---|---|---|---|---|
| JP | 2006-285095 A | | 10/2006 | |
| JP | 2006-293298 A | | 10/2006 | |
| JP | 2007-199653 A | | 8/2007 | |
| JP | 2009-269953 A | | 11/2009 | |
| JP | 2010-122656 A | | 6/2010 | |
| JP | 2010-181605 A | | 8/2010 | |
| JP | 2012-093784 | * | 5/2012 | G03F 7/028 |
| JP | 2012-215842 A | | 11/2012 | |
| JP | 2013-253227 A | | 12/2013 | |
| JP | 2015-091775 | * | 5/2015 | C08F 16/22 |
| JP | 2016-044272 A | | 4/2016 | |
| JP | 2016-060886 A | | 4/2016 | |
| JP | 2017-119671 A | | 7/2017 | |
| KR | 2012-0110048 A | | 10/2012 | |
| KR | 20170076585 A | | 7/2017 | |
| WO | 2004/066377 A1 | | 8/2004 | |
| WO | 2014/208324 A1 | | 12/2014 | |

OTHER PUBLICATIONS

Sep. 27, 2019 Extended European Search Report in European Patent Application No. 19178431.3.
Apr. 22, 2018 Search Report.
May 11, 2020 Office Action issued in Taiwanese Patent Application No. 108121174.
Sep. 11, 2020 Office Action issued in European Patent Application No. 19178431.3.
Sep. 25, 2020 Office Action issued in Korean Patent Application No. 10-2019-0073089.
Mar. 9, 2021 Office Action issued in Korean Patent Application No. 10-2019-0073089.

* cited by examiner (G)

(H)

(I)

(J)

(K)

COMPOUND AND COMPOSITION FOR FORMING ORGANIC FILM

TECHNICAL FIELD

The present invention relates to a compound and a composition for forming an organic film containing the compound that are usable in a process for producing a semiconductor device.

BACKGROUND ART

Semiconductor devices have been highly integrated and advanced in processing speed by shifting the wavelength of a light source shorter to attain a finer pattern size in lithography technologies using a light exposure (photolithography) as common arts. In order to form such a fine circuit pattern on a semiconductor device substrate (a substrate to be processed), this substrate is usually processed by dry etching using a photoresist film having a formed pattern as an etching mask. Practically, however, there is no dry etching method having a complete etching selectivity between the photoresist film and the substrate to be processed. Accordingly, substrate processing by a multilayer resist process has been commonly used recently. In this method, a middle layer film having a different etching selectivity from a photoresist film (hereinafter, a resist upper layer film) is set between the resist upper layer film and a substrate to be processed, and a pattern is obtained on the resist upper layer film, and subsequently the pattern is transferred to the middle layer film by dry etching using the resist upper layer film pattern as a dry etching mask, and the pattern is further transferred to the substrate to be processed by dry etching using the middle layer film as a dry etching mask.

One of the multilayer resist processes is a three-layer resist process, which can be performed by using a conventional resist composition that is used in a single layer resist process. In this process, an organic under layer film material composed of a composition containing an organic resin is applied onto a substrate to be processed and is baked to form an organic under layer film (hereinafter, an organic film), a resist middle layer film material composed of a silicon-containing resin composition is applied thereto and is baked to form a silicon-containing film (hereinafter, a silicon middle layer film), and a conventional resist upper layer is formed thereon. After patterning the resist upper layer film, the resist upper layer film pattern can be transferred to the silicon middle layer film by dry etching with a fluorine-base gas plasma, since organic resist upper layer films have excellent etching selectivity to silicon middle layer films. This method makes it possible to easily transfer a pattern to a silicon middle layer film even in the use of a resist upper layer film without having a sufficient film thickness for directly processing a substrate to be processed or a resist upper layer film without having a sufficient dry etching durability since the silicon middle layer film usually has a film thickness equal to or less than that of the resist upper layer film. The pattern can be transferred to the organic under layer film that has sufficient dry etching durability for substrate processing by transferring the pattern to the organic under layer film by dry etching with an oxygen base or hydrogen base gas plasma using the silicon middle layer film having the pattern transferred thereon as a dry etching mask. This organic under layer film pattern having the pattern transferred thereon can be transferred to a substrate by dry etching by using a fluorine base gas or a chlorine base gas.

On the other hand, the attempt to produce smaller pattern sizes in production processes of semiconductor devices is approaching the inherent limit due to the wavelength of a light source for photolithography. Accordingly, higher integration of semiconductor devices have been investigated recently without depending on a smaller pattern sizes. As one of these methods, semiconductor devices with complicated structures have been investigated including a multi gate structure and a gate all-around, and a part of them have been put to practical use already. When these structures are formed by a multilayer resist process, it is possible to apply an organic film material that is capable of planarization by gap filling a minute pattern formed on a substrate to be processed such as a hole, a trench, and a fin with the organic film material without a void, or planarization by filling a step or a pattern dense portion and no pattern region with the organic film material. Such an organic film material is used for forming a planar organic under layer film surface on a stepped substrate to decrease fluctuation of a film thickness of a silicon middle layer film or a resist upper layer film formed thereon, thereby making it possible to avoid the deterioration of depth of focus in photolithography or a margin in the subsequent processing step of a substrate to be processed. This makes it possible to produce semiconductor devices in good yield. On the other hand, it is difficult to produce semiconductor devices in a good yield by a single layer resist process since it requires an upper layer resist film to have thicker film thickness for gap filling a stepped or patterned substrate to be processed, thereby causing lower tolerance for pattern forming in exposure such as pattern collapse after exposure and development as well as degradation of a pattern profile due to reflection from a substrate in exposure.

As a method for next-generation semiconductor devices to achieve higher processing speed, investigations have been undertaken on new materials that have high electron mobility using strained silicon, gallium-arsenic, etc. or fine materials such as an ultrathin film polysilicon whose thickness is controlled at the angstrom level. When such a new fine material is applied to a substrate to be processed, however, the material can be corroded with oxygen in air atmosphere under conditions in forming a planar film using the organic under layer film material as described above, for example, the film forming conditions of 300° C. or more in air atmosphere. This risks the semiconductor device to fail to attain higher processing speed as it is designed, and fail to attain the yield that can be by industrial manufacturing. Accordingly, an organic under layer material that can be formed in an inert gas is demanded in order to avoid lowering of the yield due to corrosion of a substrate with air atmosphere under the higher temperature conditions.

As a material for forming an organic film for a multilayer resist process, condensation resins have been known including a phenolic or naptholic compound using a carbonyl compound such as ketones and aldehydes or aromatic alcohols as a condensation agent. Illustrative examples thereof include fluorene bisphenol novolak resins described in Patent Literature 1, bisphenol compounds and novolak resins thereof described in Patent Literature 2, novolak resins of adamantanephenol compounds described in Patent Literature 3, and bisnaphthol compounds and novolak resins thereof described in Patent Literature 4. These materials are formed into a film that has solvent resistance to the coating film material used in the subsequent step by crosslinking thereof with a methylol compound as a crosslinking agent or curing function due to crosslinking reaction including oxidation of the aromatic ring at the α-position by an effect of oxygen in air atmosphere, followed by condensation.

Additionally, Patent Literatures 5 to 10 have been known as examples of each material in which a triple bond is used as a group for intermolecular crosslinking of a curable resin. For these materials, however, the actual curing conditions in an inert gas is not exemplified. There is no information on forming the cured film of these materials in an inert gas or fluctuation of film thicknesses due to thermal decomposition under high temperature conditions.

CITATION LIST

Patent Literature

PATENT LITERATURE 1: Japanese Patent Laid-Open Publication (Kokai) No. 2005-128509
PATENT LITERATURE 2: Japanese Patent Laid-Open Publication (Kokai) No. 2006-293298
PATENT LITERATURE 3: Japanese Patent Laid-Open Publication (Kokai) No. 2006-285095
PATENT LITERATURE 4: Japanese Patent Laid-Open Publication (Kokai) No. 2010-122656
PATENT LITERATURE 5: Japanese Patent Laid-Open Publication (Kokai) No. 2010-181605
PATENT LITERATURE 6: International Patent Laid-Open Publication No. WO 2014-208324
PATENT LITERATURE 7: Japanese Patent Laid-Open Publication (Kokai) No. 2012-215842
PATENT LITERATURE 8: Japanese Patent Laid-Open Publication (Kokai) No. 2016-044272
PATENT LITERATURE 9: Japanese Patent Laid-Open Publication (Kokai) No. 2016-060886
PATENT LITERATURE 10: Japanese Patent Laid-Open Publication (Kokai) No. 2017-119671

SUMMARY OF INVENTION

Technical Problem

The present invention was accomplished in view of the above-described problems. It is an object of the present invention to provide a compound that is capable of curing under the film forming conditions that is not only in air but also in an inert gas without forming volatile byproducts to form an organic under layer film that has good dry etching durability during substrate processing, excellent heat resistance and favorable characteristics of gap filling and planarizing a pattern formed on a substrate; a composition for forming an organic film using the compound, and a compound that is suitable as an intermediate to obtain the compound.

Solution to Problem

To solve the above problems, the present invention provides a compound shown by the following general formula (1-1),

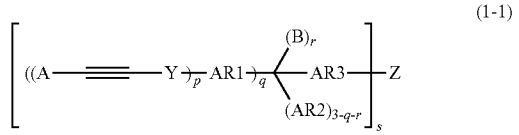

wherein AR1 and AR2 each independently represent an aromatic ring optionally having a substituent or an aromatic ring that contains at least one nitrogen atom and/or sulfur atom optionally having a substituent, two AR1s, AR1 and AR2, or two AR2s are optionally bonded with each other to form a ring structure; AR3 represents a benzene ring, a naphthalene ring, a thiophene ring, a pyridine ring, or a diazine ring optionally having a substituent; A represents an organic group having 1 to 30 carbon atoms; B represents an anionic leaving group capable of forming a reactive cation by an action of either or both of heat and acid; Y represents a divalent organic group that optionally contains one or more oxygen atoms having 1 to 10 carbon atoms; "p" is 1 or 2; "q" is 1 or 2; "r" is 0 or 1; "s" is 2 to 4; when s=2, Z represents a single bond, a divalent atom, or a divalent organic group; and when s=3 or 4, Z represents a trivalent or quadrivalent atom or organic group.

The inventive compound is capable of curing to form an organic film even in an inert gas not only in air atmosphere without forming byproducts. The inventive compound is also capable of forming an organic under layer film that has good dry etching durability in substrate processing not only excels in heat resistance and characteristics of gap filling and planarizing a topography formed on a substrate. The organic film obtained by crosslinking the compound becomes an organic film free from fluctuation of the film thickness due to thermal decomposition even during CVD (Chemical Vapor Deposition) deposition of a hard mask.

In this case, the above compound is preferably a compound shown by the following general formula (1-2),

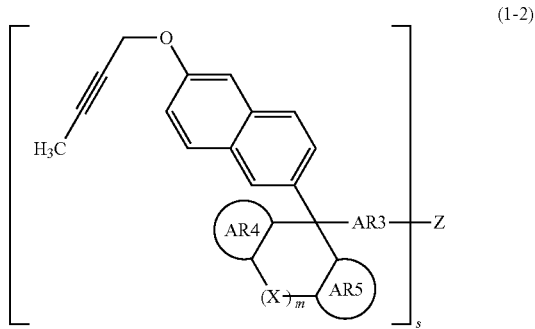

wherein AR3 has the same meaning as defined above; AR4 and AR5 each represent a benzene ring, a naphthalene ring, a thiophene ring, or a pyridine ring optionally having a substituent; "m" is 0 or 1; when m=0, AR4 and AR5 do not form a bridged structure, when m=1, AR4 and AR5 form a bridged structure through X; X represents a single bond or any of groups shown by the following formulae (1-2-1);

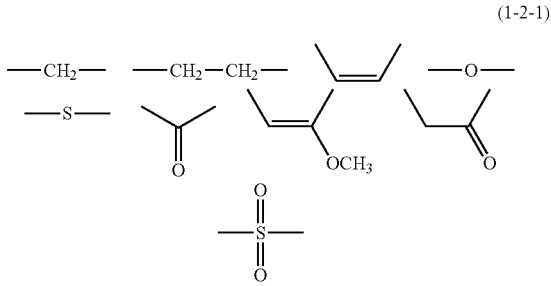

and "s" and Z have the same meanings as defined above.

In this case the above compound is preferably a compound shown by the following general formula (1-3).

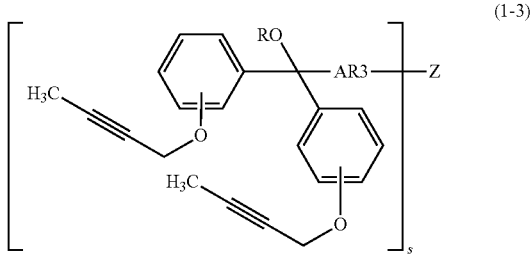

wherein AR3 has the same meaning as defined above; R represents a hydrogen atom or a monovalent organic group having 1 to 30 carbon atoms; and "s" and Z have the same meanings as defined above.

As described above, the compounds shown by the formula (1-2) and the compounds shown by the formula (1-3) are preferable as the compound of the present invention.

The present invention also provides a composition for forming an organic film, comprising (A) a compound shown by the following general formula (1-1) and (B) an organic solvent,

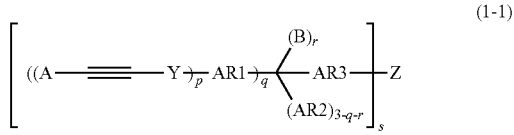

wherein AR1 and AR2 each independently represent an aromatic ring optionally having a substituent or an aromatic ring that contains at least one nitrogen atom and/or sulfur atom optionally having a substituent, two AR1s, AR1 and AR2, or two AR2s are optionally bonded with each other to form a ring structure; AR3 represents a benzene ring, a naphthalene ring, a thiophene ring, a pyridine ring, or a diazine ring optionally having a substituent; A represents an organic group having 1 to 30 carbon atoms; B represents an anionic leaving group capable of forming a reactive cation by an action of either or both of heat and acid; Y a divalent organic group that optionally contains one or more oxygen atoms having 1 to 10 carbon atoms; "p" is 1 or 2; "q" is 1 or 2; "r" is 0 or 1; "s" is 2 to 4; when s=2, Z represents a single bond, a divalent atom, or a divalent organic group, and when s=3 or 4, Z represents a trivalent or quadrivalent atom or organic group.

The inventive composition for forming an organic film is capable of forming an organic film in an inert gas, making the organic film have higher heat resistance, higher dry etching durability, and higher gap filling/planarizing characteristics.

In this case, it is preferable that the above compound (A) be a compound shown by the following general formula (1-2),

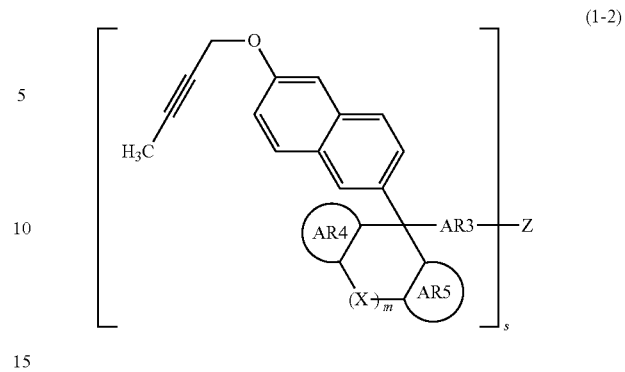

wherein AR3 has the same meaning as defined above; AR4 and AR5 each represent a benzene ring, a naphthalene ring, a thiophene ring, or a pyridine ring optionally having a substituent; "m" is 0 or 1; when m=0, AR4 and AR5 do not form a bridged structure, when m=1, AR4 and AR5 form a bridged structure through X; X represents a single bond or any of groups shown by the following formulae (1-2-1);

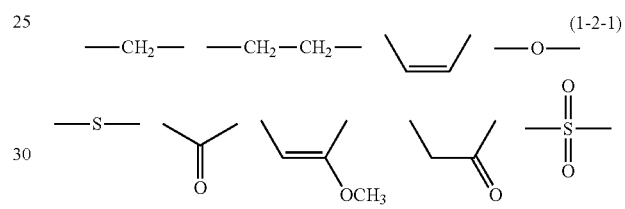

and "s" and Z have the same meanings as defined above.

In this case, it is preferable that the above compound (A) be a compound shown by the following general formula (1-3),

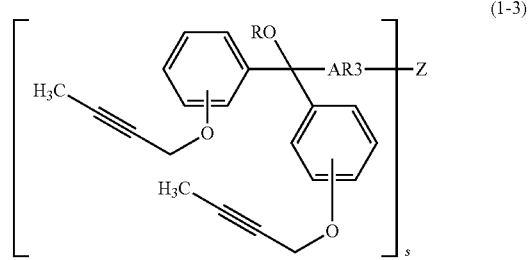

wherein AR3 has the same meaning as defined above; R represents a hydrogen atom or a monovalent organic group having 1 to 30 carbon atoms; and "s" and Z have the same meanings as defined above.

As described above, the compounds shown by the formula (1-2) and the compounds shown by the formula (1-3) are preferable as the compound (A).

The inventive composition for forming an organic film can comprise at least one of (C) an acid generator, (D) a surfactant, (E) a crosslinking agent, and (F) a plasticizer.

The inventive composition for forming an organic film can contain at least one of the components (C) to (F) in accordance with the object.

The present invention also provides a compound shown by the following general formula (1-4),

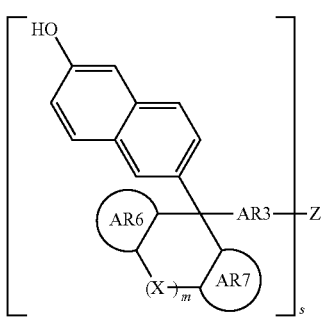

wherein AR3 represents a benzene ring, a naphthalene ring, a thiophene ring, a pyridine ring, or a diazine ring optionally having a substituent; AR6 and AR7 each represent a benzene ring, a naphthalene ring, a thiophene ring, or a pyridine ring optionally having a substituent; "m" is 0 or 1; when m=0, AR6 and AR7 do not form a bridged structure, when m=1, AR6 and AR7 form a bridged structure through X; X represents a single bond or any of groups shown by the following formulae (1-2-1);

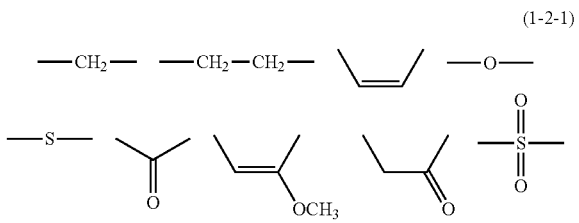

when AR6 and AR7 are bonded through a single bond, at least one of ARE and AR7 is not a benzene ring; "s" is 2 to 4; when s=2, Z represents a single bond, a divalent atom, or a divalent organic group, and when s=3 or 4, Z represents a trivalent or quadrivalent atom or organic group.

The present invention also provides a compound shown by the following general formula (1-5),

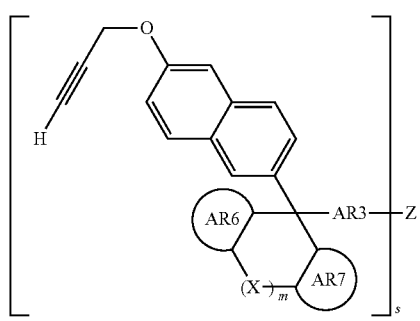

wherein AR3 represents a benzene ring, a naphthalene ring, a thiophene ring, a pyridine ring, or a diazine ring optionally having a substituent; AR6 and AR7 each represent a benzene ring, a naphthalene ring, a thiophene ring, or a pyridine ring optionally having a substituent; "m" is 0 or 1; when m=0, AR6 and AR7 do not form a bridged structure, when m=1, AR6 and AR7 form a bridged structure through X; X represents a single bond or any of groups shown by the following formulae (1-2-1);

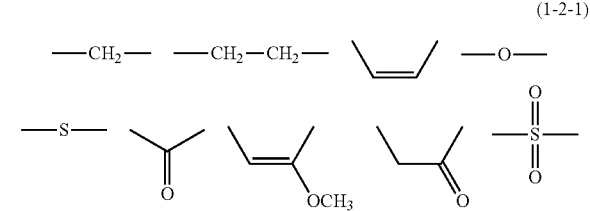

when AR6 and AR7 are bonded through a single bond, at least one of AR6 and AR7 is not a benzene ring; "s" is 2 to 4; when s=2, Z represents a single bond, a divalent atom, or a divalent organic group; and when s=3 or 4, Z represents a trivalent or quadrivalent atom or organic group.

The inventive compounds shown by the general formulae (1-4) and (1-5) are suitable as an intermediate to produce the compound shown by the general formula (1-1), which is a material for forming an organic film capable of forming an organic film in an inert gas, making the organic film have higher heat resistance, higher dry etching durability, and higher gap filling/planarizing characteristics.

Advantageous Effects of Invention

As described above, the inventive compound shown by the general formula (1-1) is a compound that is useful for curing a film forming in inert gas, which prevents a substrate from corrosion, the formation of volatile byproducts and forms an organic under layer film that has superior gap filling and planarizing characteristics. The composition for forming an organic film containing this compound is a material capable of forming an organic film that has excellent gap filling/planarizing characteristics combined with various properties such as heat resistance and etching durability. Accordingly, they are very useful as an organic film material in multilayer resist processes such as a two-layer resist process, a three-layer resist process using a silicon middle layer film, and a four-layer resist process using a silicon middle layer film and an organic bottom antireflective coating as well as a planarization material for producing a semiconductor device. The organic film formed from the inventive composition for forming an organic film is excellent in heat resistance, and is favorably used for patterning without causing fluctuation of the film thicknesses due to thermal decomposition even during the formation of hard mask via a CVD process on the organic under layer film.

DESCRIPTION OF EMBODIMENTS

Figure 1:
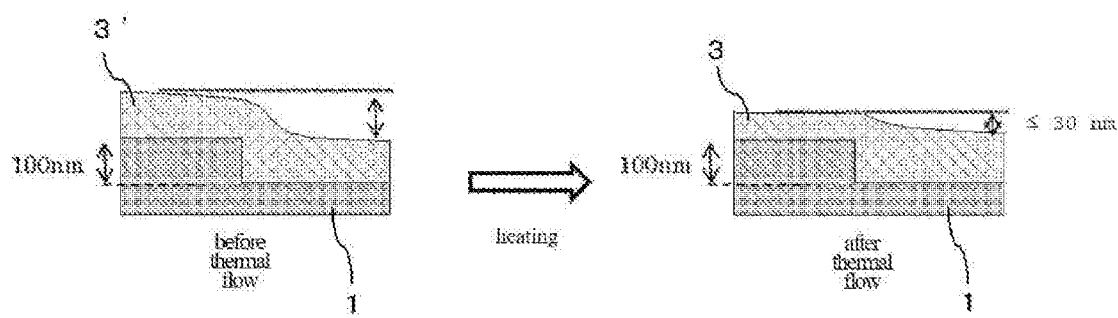
FIG. 1 is an explanatory diagram of the planarizing characteristics in the present invention.

As described above, it has been demanded for an organic under layer film that is formed without the generation of volatile byproduct during film forming conditions under inert gas, for example, at a temperature of 300° C. or more, to prevent corrosion of a substrate, and is excellent in characteristics of gap filling and planarizing a pattern formed on a substrate as well as dry etching durability in substrate processing. Additionally, it has been demanded for an organic film that is free from fluctuation of the film thickness due to decomposition even during CVD hard mask deposition is formed on the organic under layer film, and it has been desired to develop a compound for forming an organic film to attain these properties.

The formation of an organic under layer film is usually performed such that a compound for forming an organic film is dissolved in an organic solvent to form a formulation. This is applied onto a substrate having semiconductor device structures or wiring formed thereon followed by baking to form an organic under layer film. The composition forms a coating film in accordance with the shape of a stepped structure on the substrate immediately after application thereof. When the coating film is baked, however, most of the organic solvent is evaporated during the curing, and an organic film is formed from the compound for forming an organic film remaining on the substrate. The inventors noticed this behavior and have conceived that if the compound for forming an organic film remaining on the substrate has sufficient thermal fluidity which allows the planarization of substrate topography during film formation and curing to form a planer film.

In order to provide a material that has high heat resistance and is capable of curing in an inert gas without containing oxygen to prevent a substrate from corrosion, the inventors continued to diligently investigate a structure that can cure under such conditions. Thus the present inventors have found that the compound shown by the general formula (1-1), having at least one triple bond as a substituent as an intermolecular crosslinking group, is capable of curing under the film forming conditions in either air atmosphere or an inert gas through the substituents with a triple bond that are disposed efficiently to show curing properties equal to conventional under layer film materials even in an inert gas without forming byproducts in the curing reaction, and brings higher heat resistance due to the aromatic rings that are disposed efficiently. The present inventors have also found that this compound possesses higher gap filling/planarizing characteristics due to the good thermal fluidity to give a composition for forming an organic film that has excellent dry etching durability and heat resistance that is free from thickness fluctuation of the coated film due to thermal decomposition even when a CVD hard mask is formed; thereby brought the present invention to completion.

Hereinafter, the present invention will be explained in detail, but the present invention is not limited thereto.
<Compound (1)>

Thus, the present invention is a compound shown by the following general formula (1-1) (hereinafter, referred to as Compound (1)),

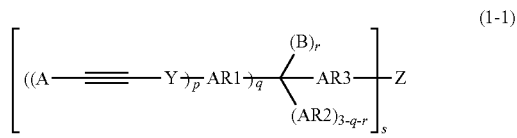

wherein AR1 and AR2 each independently represent an aromatic ring optionally having a substituent or an aromatic ring that contains at least one nitrogen atom and/or sulfur atom optionally having a substituent, two AR1s, AR1 and AR2, or two AR2s are optionally bonded with each other to form a ring structure; AR3 represents a benzene ring, a naphthalene ring, a thiophene ring, a pyridine ring, or a diazine ring optionally having a substituent; A represents an organic group having 1 to 30 carbon atoms; B represents an anionic leaving group capable of forming a reactive cation by an action of either or both of heat and acid; Y represents a divalent organic group that optionally contains one or more oxygen atoms having 1 to 10 carbon atoms; "p" is 1 or 2; "q" is 1 or 2; "r" is 0 or 1; "s" is 2 to 4; when s=2, Z represents a single bond, a divalent atom, or a divalent organic group; and when s=3 or 4, Z represents a trivalent or quadrivalent atom or organic group.

As described above, AR1 and AR2 each independently represent an aromatic ring optionally having a substituent or an aromatic ring that contains at least one nitrogen atom and/or sulfur atom optionally having a substituent, two AR1s, AR1 and AR2, or two AR2s are optionally bonded with each other to form a ring structure. Illustrative examples of these AR1 and AR2 include a benzene ring, a naphthalene ring, a thiophene ring, and a pyridine ring optionally having a substituent. Illustrative examples of the substituent include an alkyl group and an alkoxy group.

Additionally, A represents an organic group having 1 to 30 carbon atoms, and is preferably an alkyl group, particularly a methyl group, for example. B represents an anionic leaving group capable of forming a reactive cation by an action of either or both of heat and acid such as a hydroxy group, an alkoxy group, an acyloxy group, a sulfonyloxy group. Y represents a divalent organic group that optionally contains one or more oxygen atoms having 1 to 10 carbon atoms, particularly an organic group that contain one oxygen atom having 1 to 5 carbon atoms.

In addition, "p" is 1 or 2; "q" is 1 or 2; "r" is 0 or 1; "s" is 2 to 4. When s=2, Z represents a single bond, a divalent atom (e.g., oxygen atom, sulfur atom, etc.), or a divalent organic group. When s=3 or 4, Z represents a trivalent or quadrivalent atom (e.g., nitrogen atom, carbon atom, etc.) or organic group.

The Compound (1) is specifically Compound (2) shown by the following general formula (1-2) or Compound (3) shown by the following general formula (1-3).

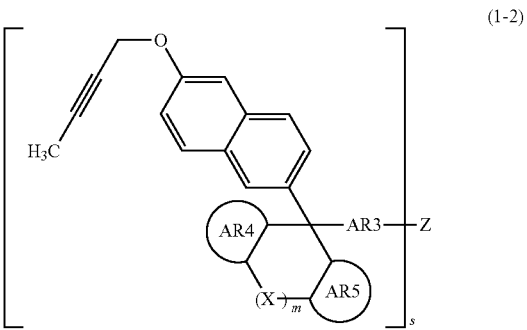

wherein AR3 has the same meaning as defined above; AR4 and AR5 each represent a benzene ring, a naphthalene ring, a thiophene ring, or a pyridine ring optionally having a substituent; "m" is 0 or 1; when m=0, AR4 and AR5 do not form a bridged structure, when m=1, AR4 and AR5 form a bridged structure through X; X represents a single bond or any of groups shown by the following formulae (1-2-1);

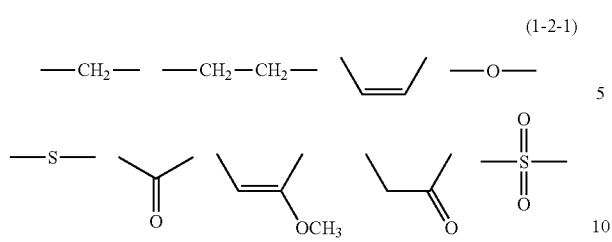

(1-2-1)

and "s" and Z have the same meanings as defined above.

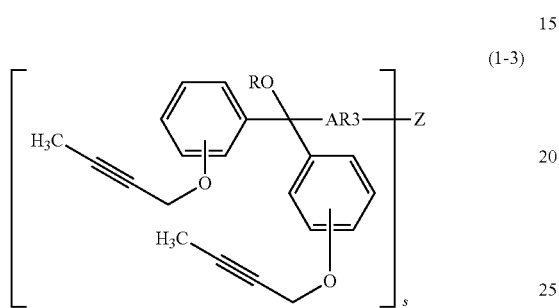

(1-3)

wherein AR3 has the same meaning as defined above; R represents a hydrogen atom or a monovalent organic group having 1 to 30 carbon atoms; and "s" and Z have the same meanings as defined above.

Among the Compound (1), a compound shown by the general formula (1-2) is preferable. Illustrative examples of the Compound (2) include the following, but are not limited thereto.

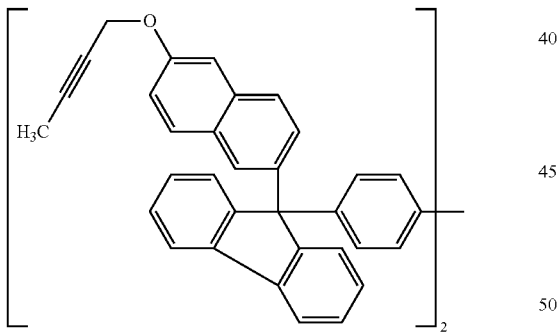

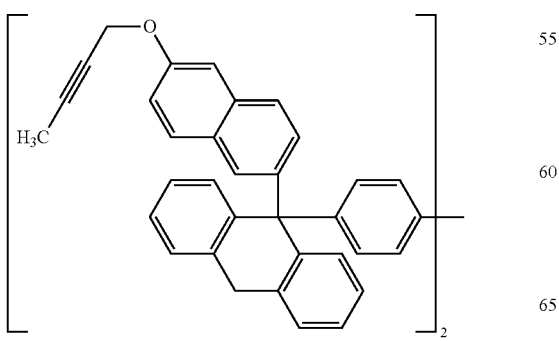

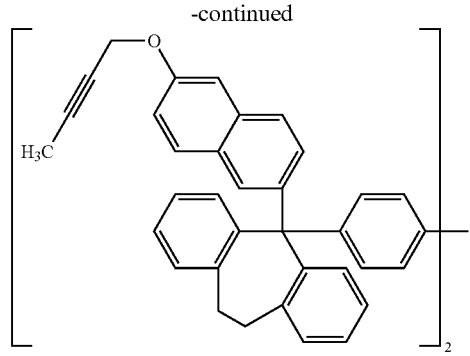

-continued

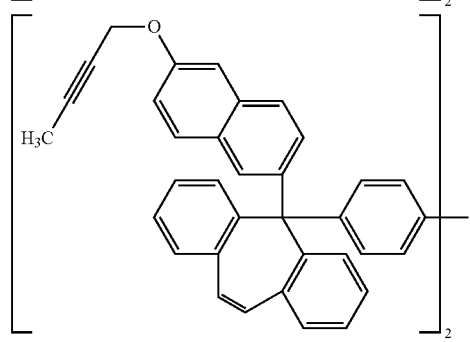

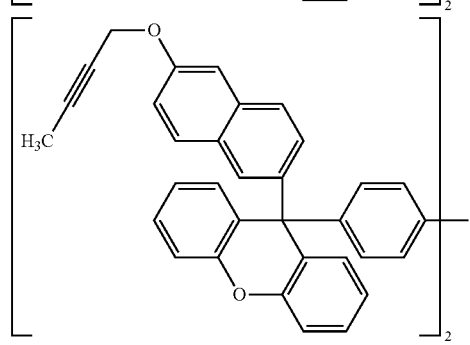

-continued
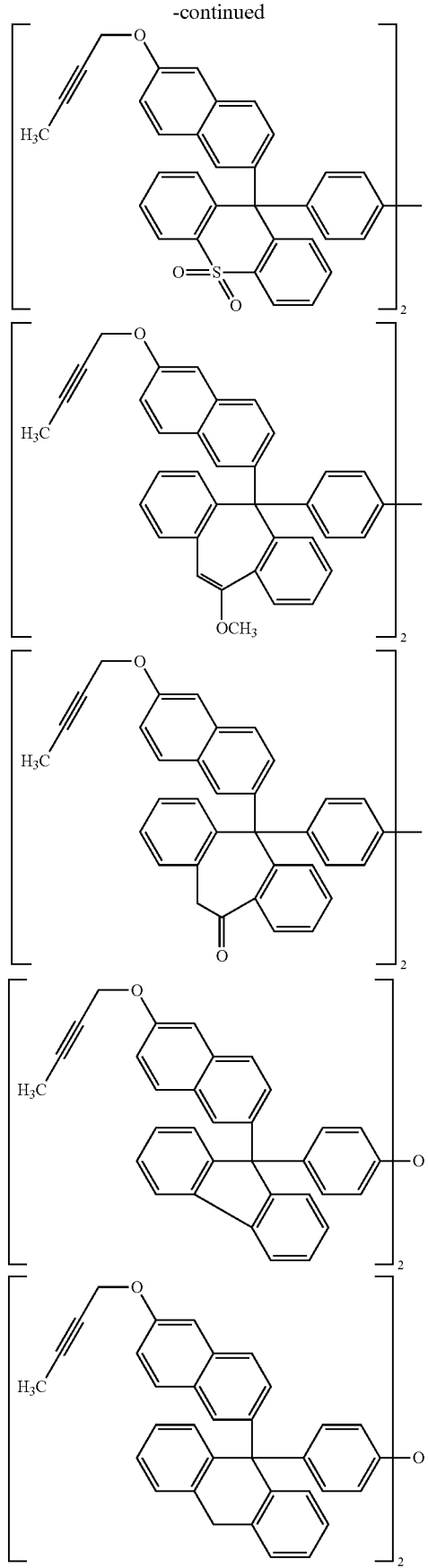
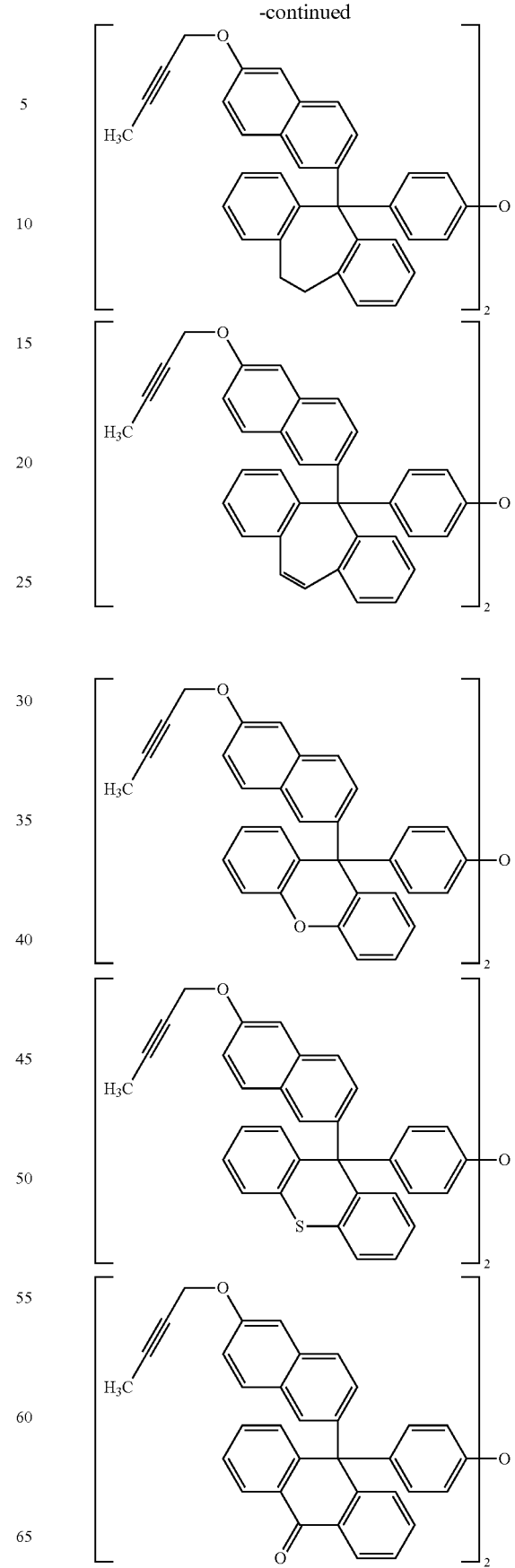

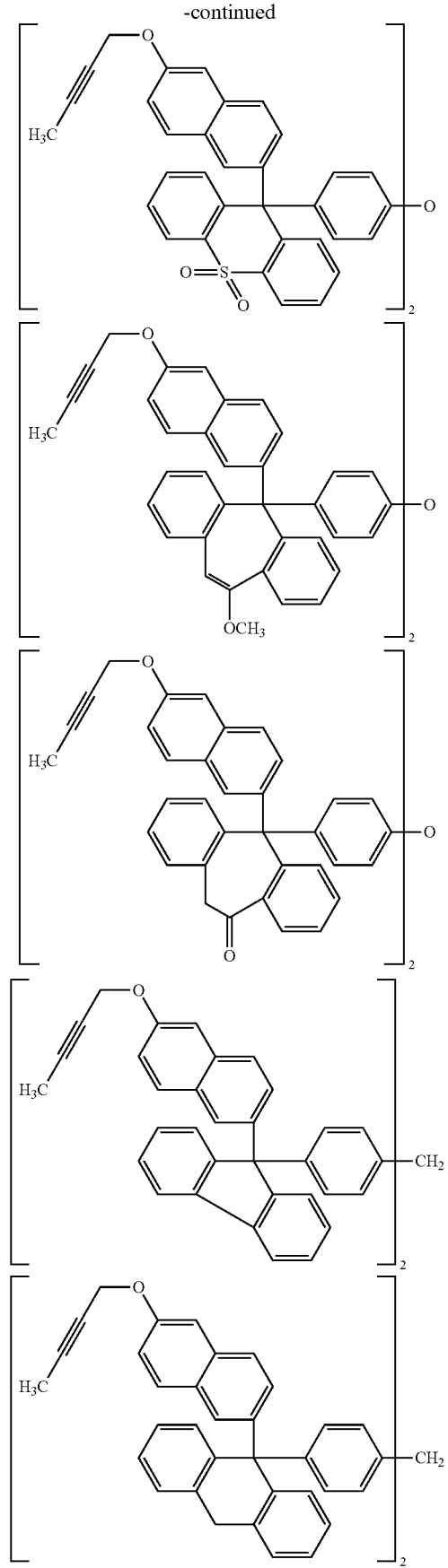
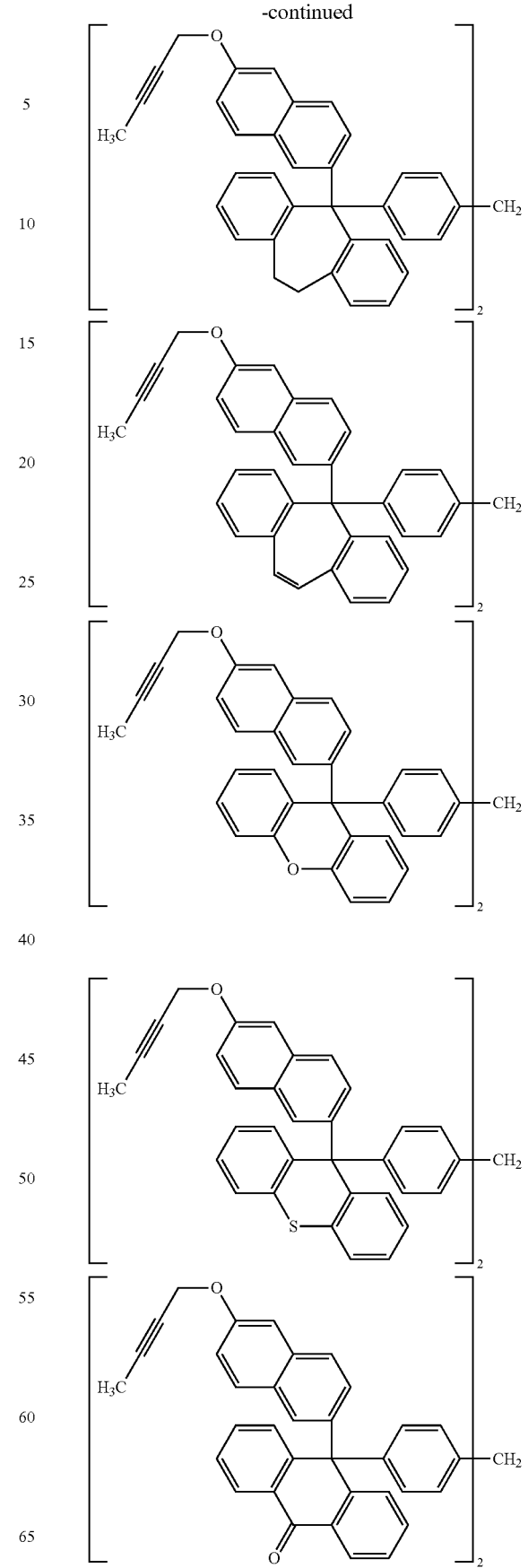

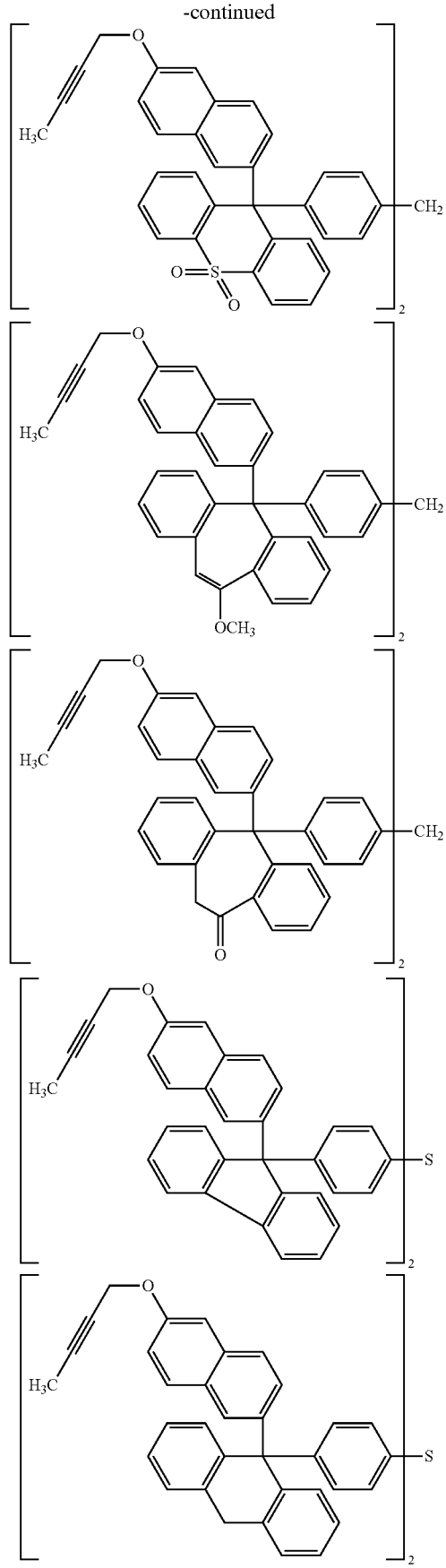
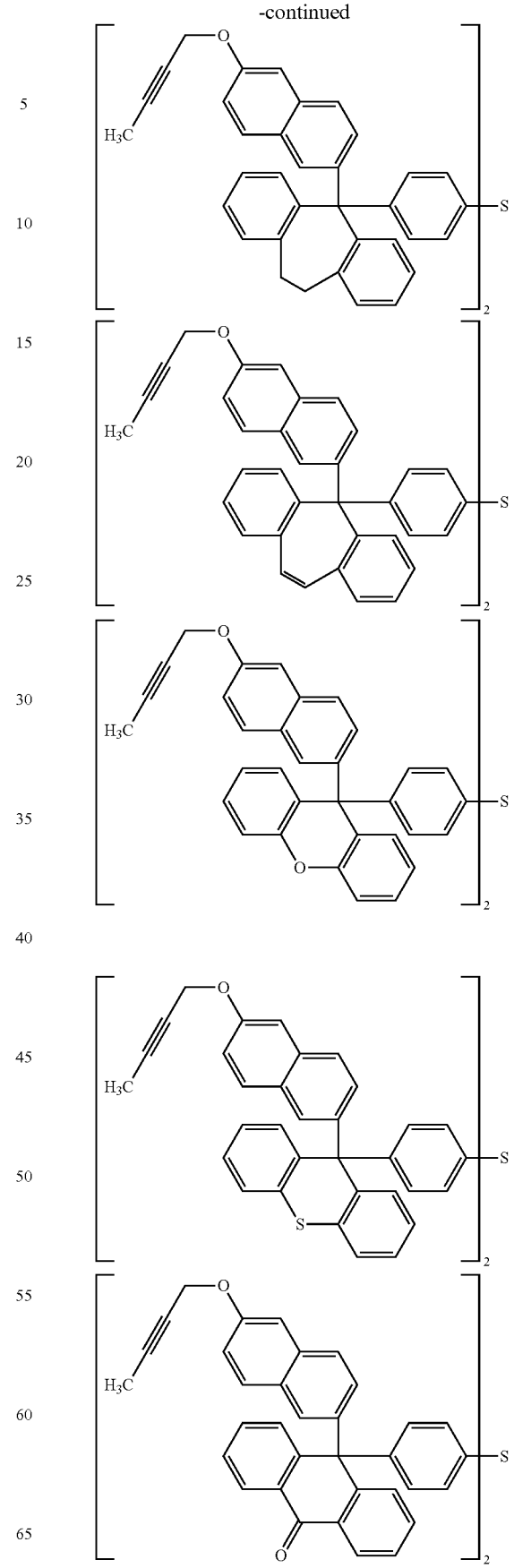

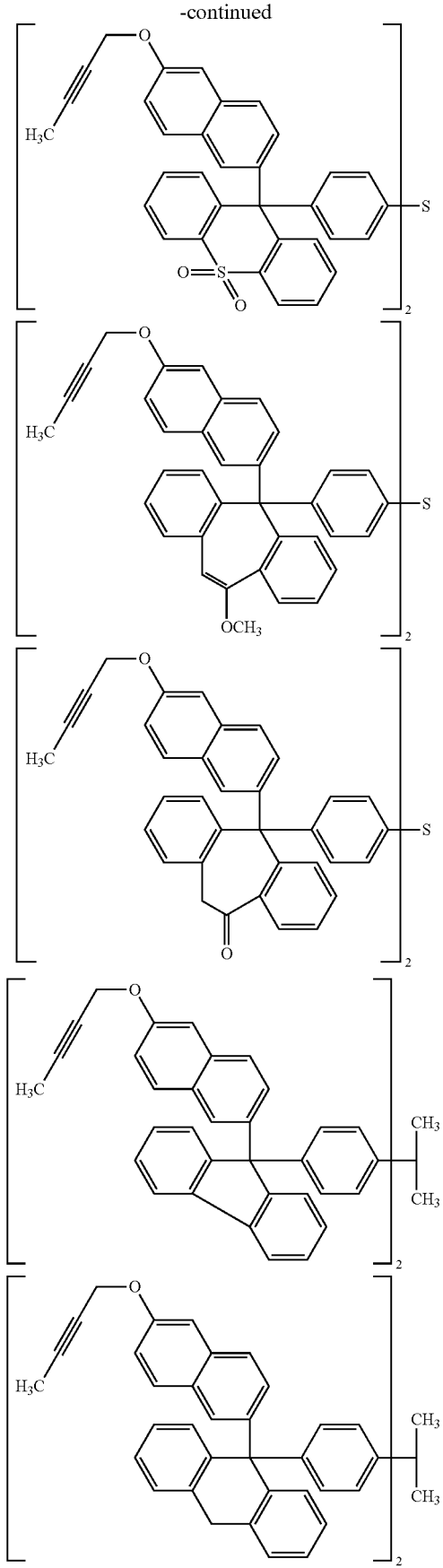
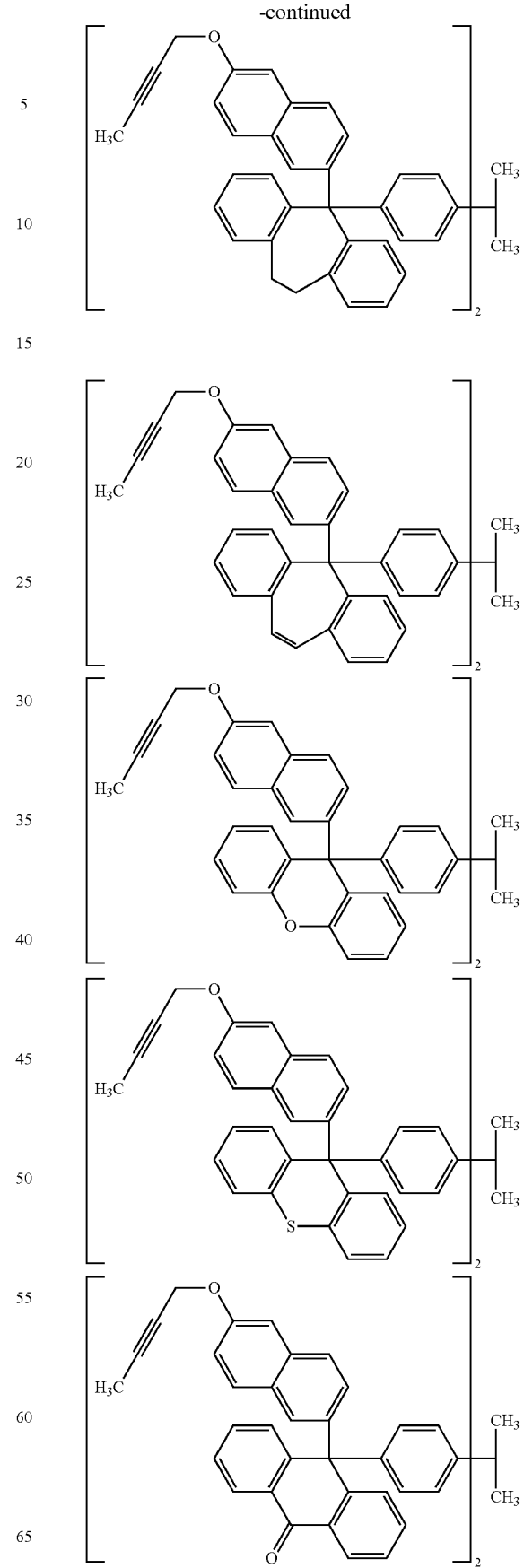

-continued
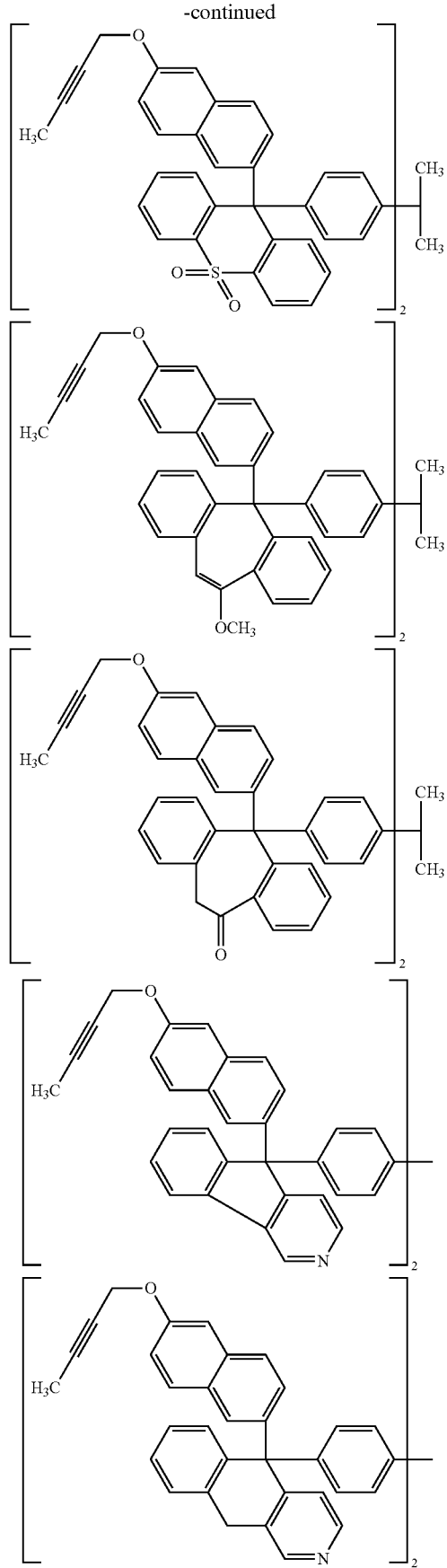
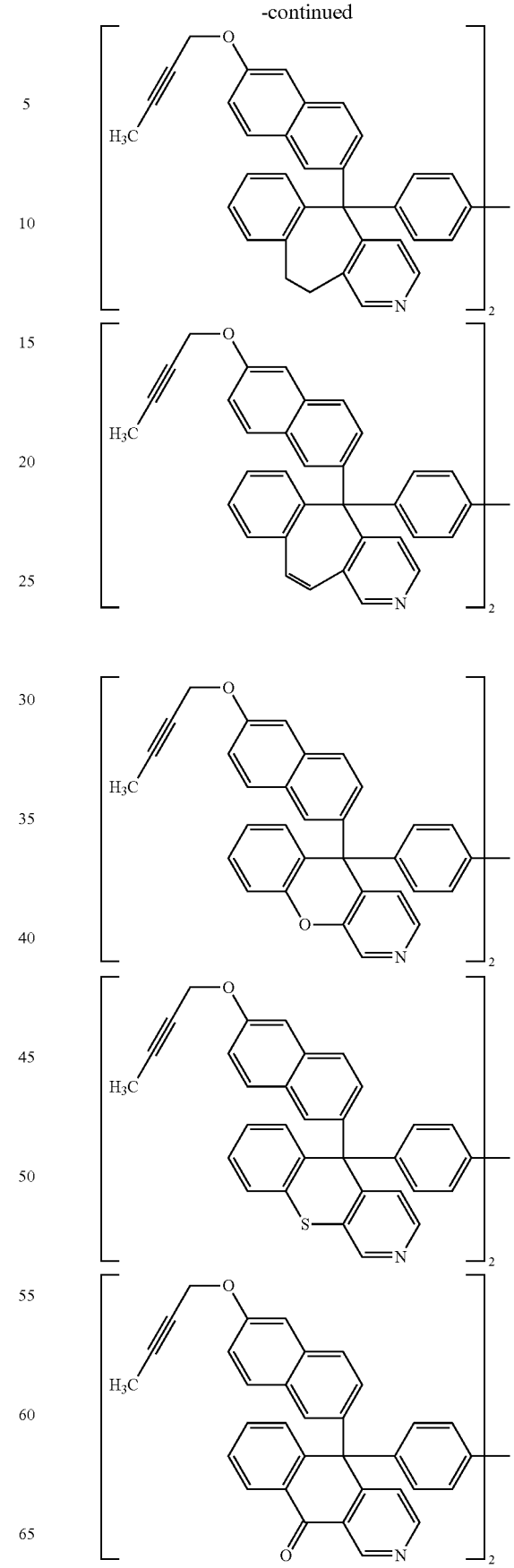

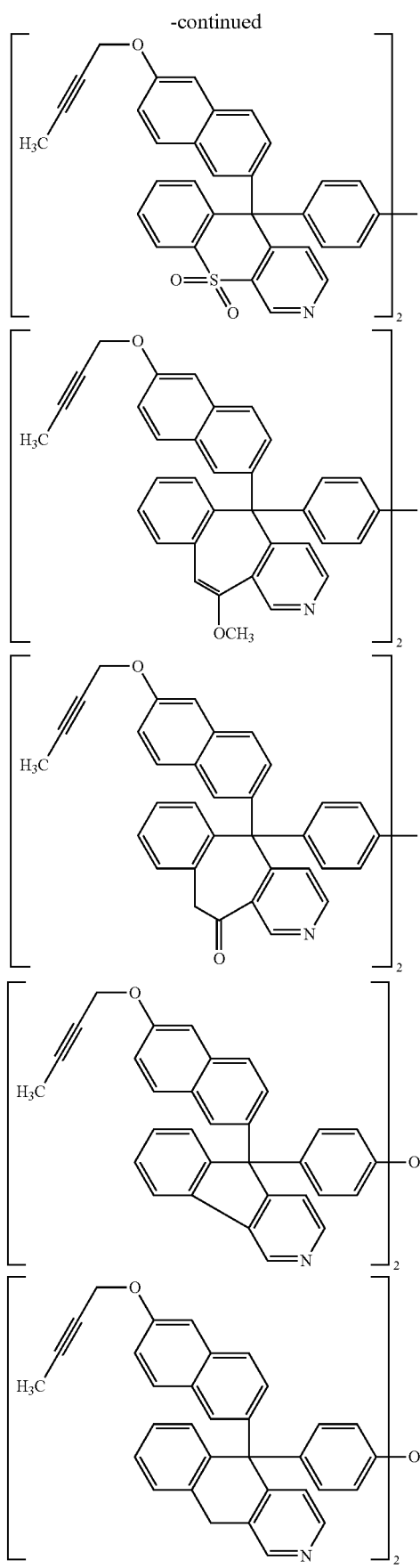
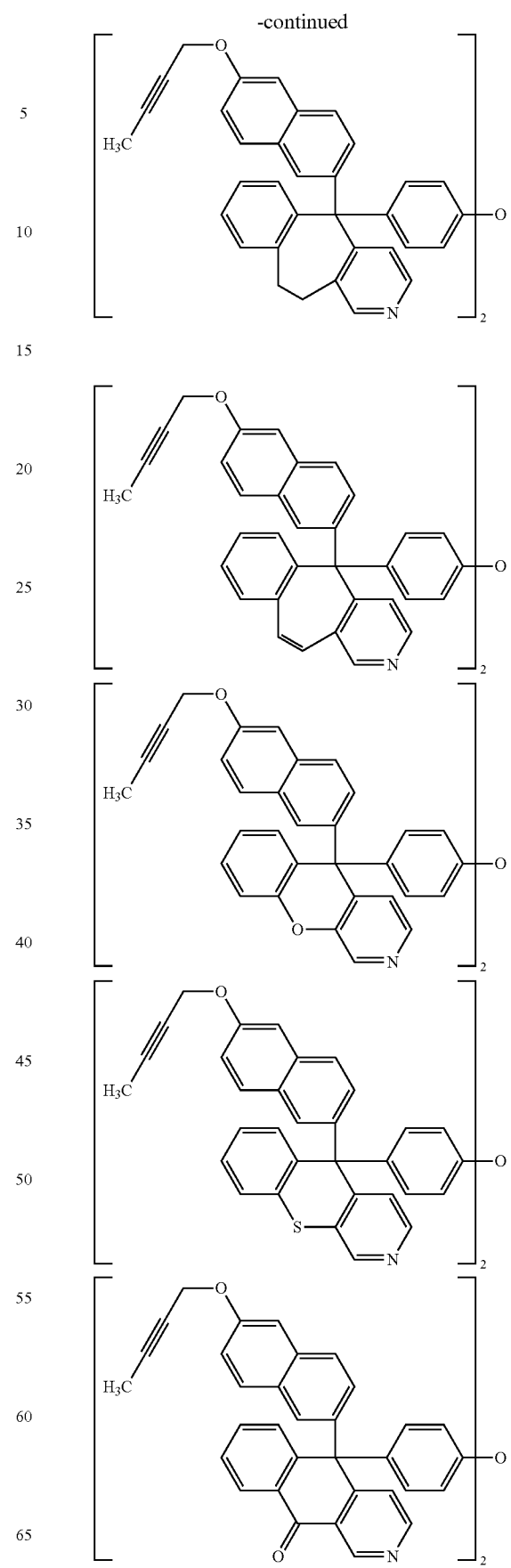

-continued
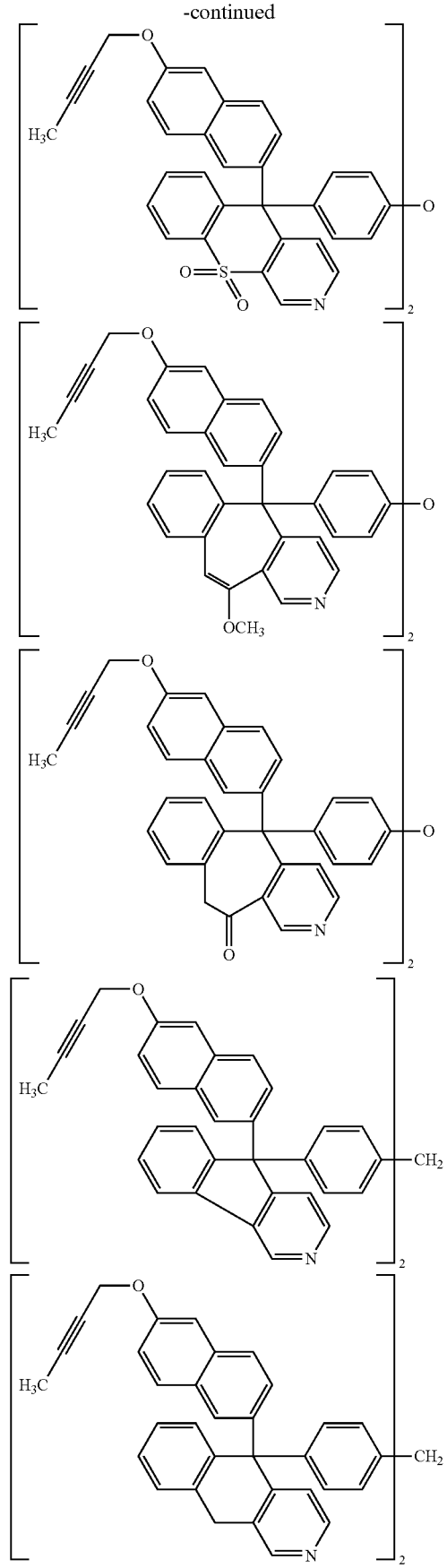
-continued
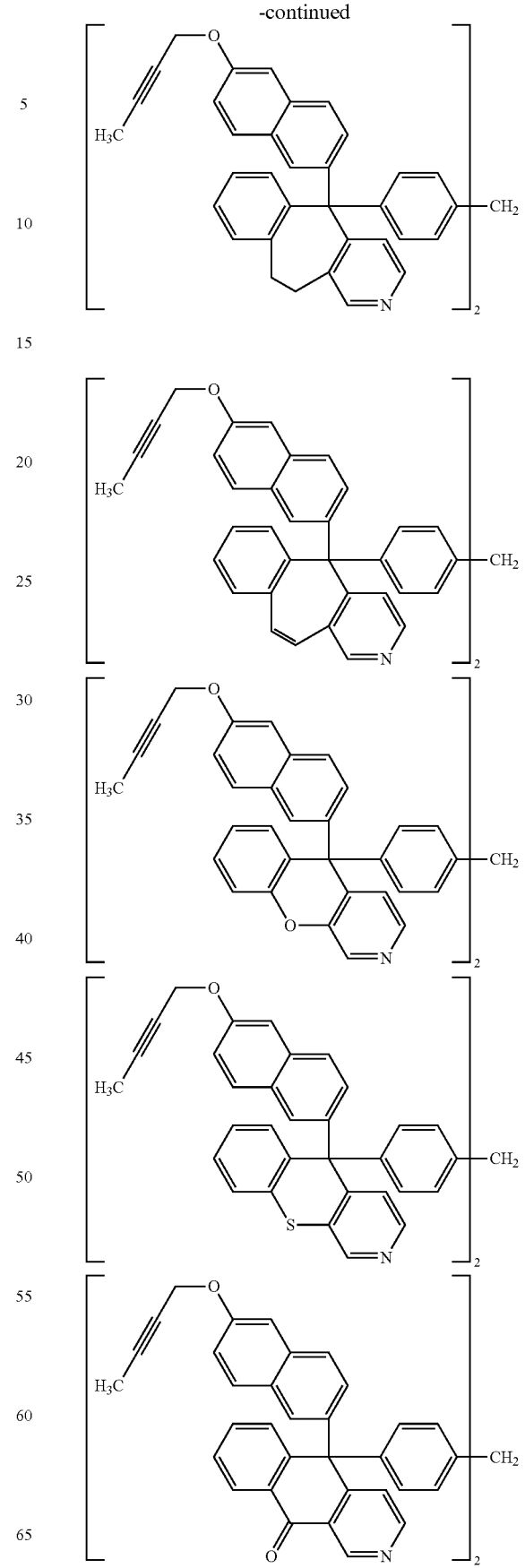

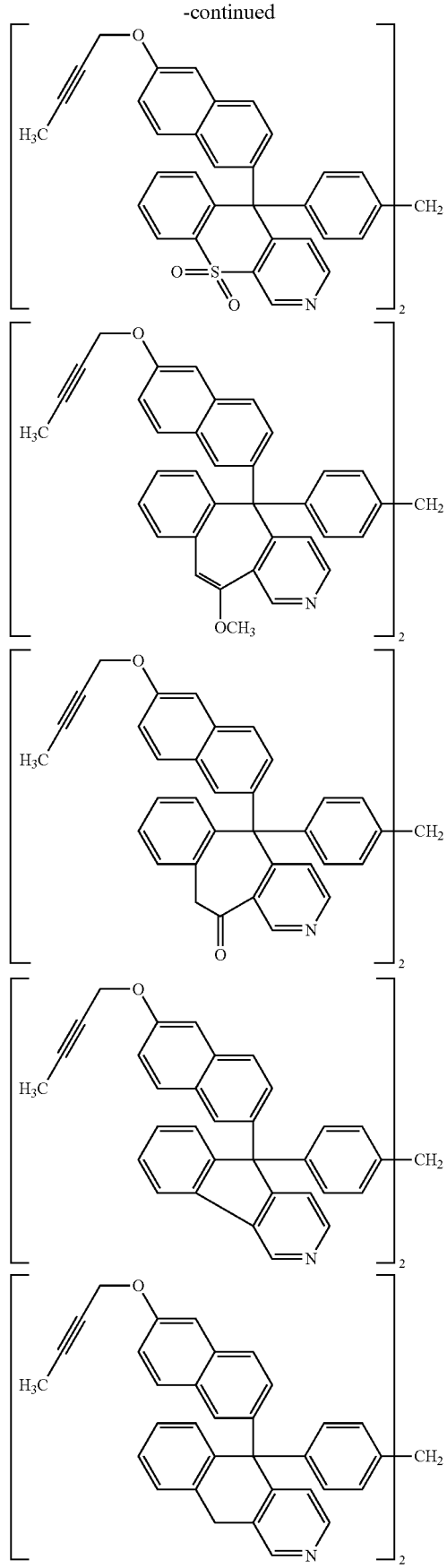
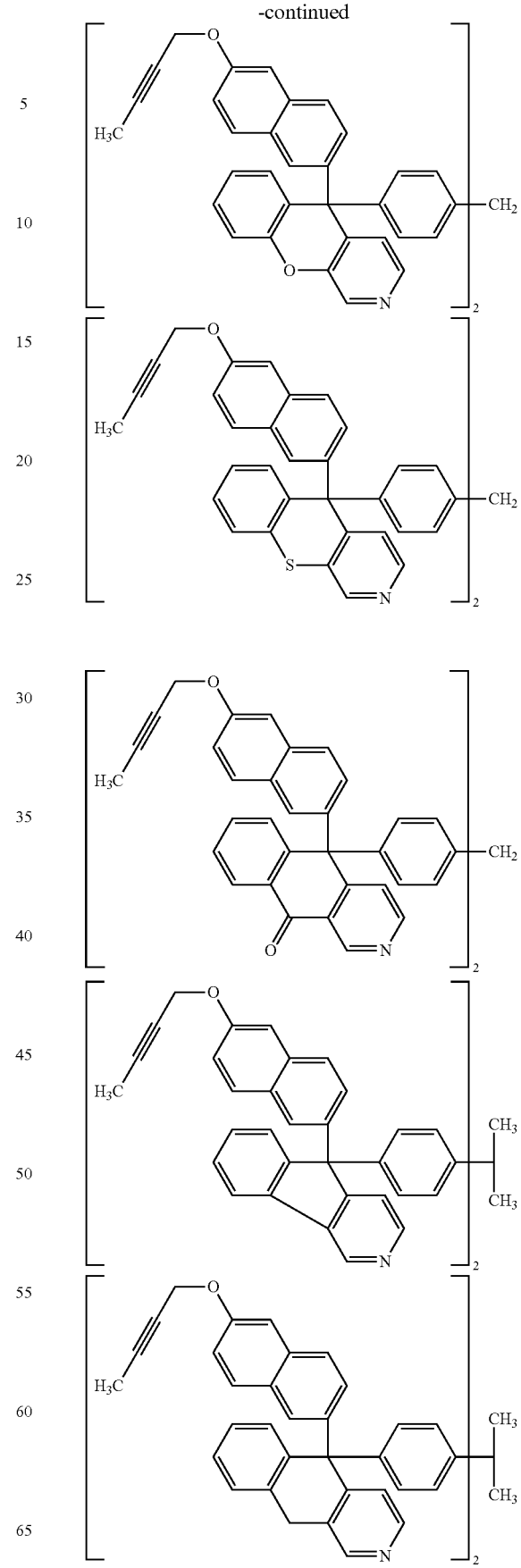

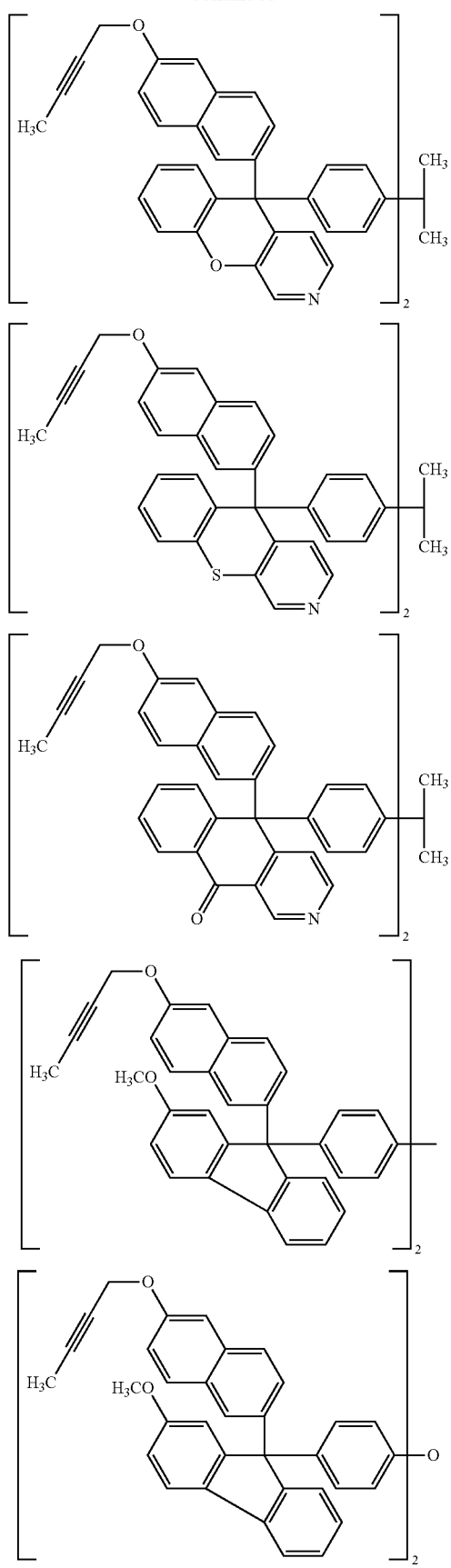
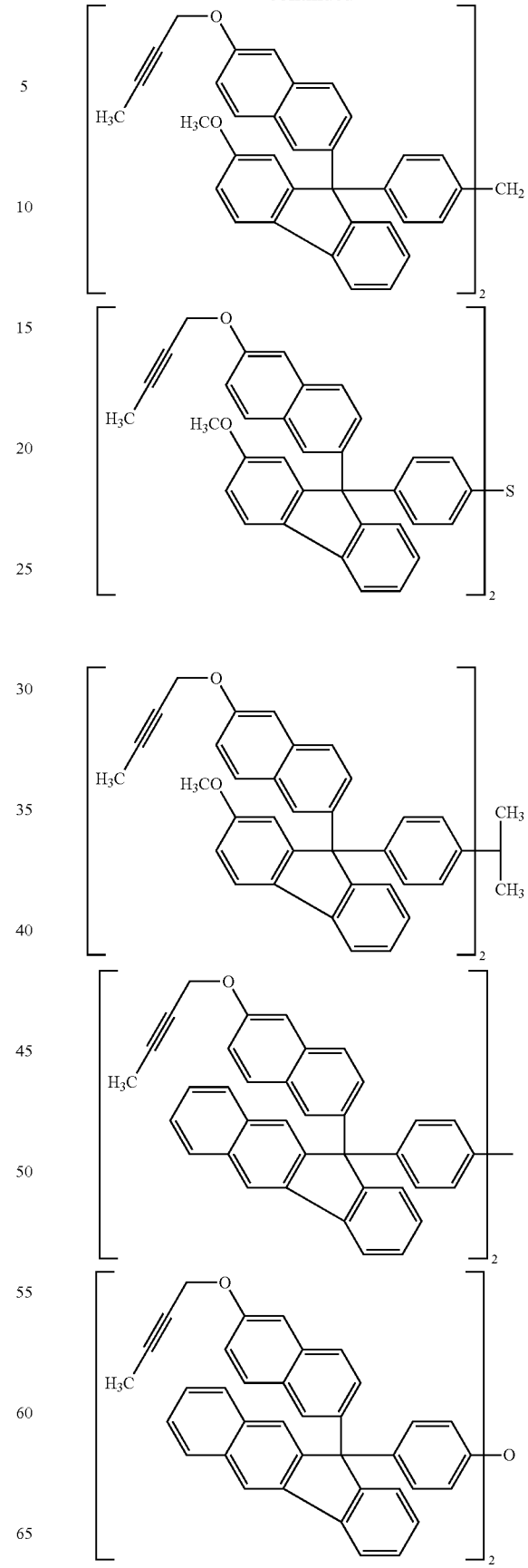

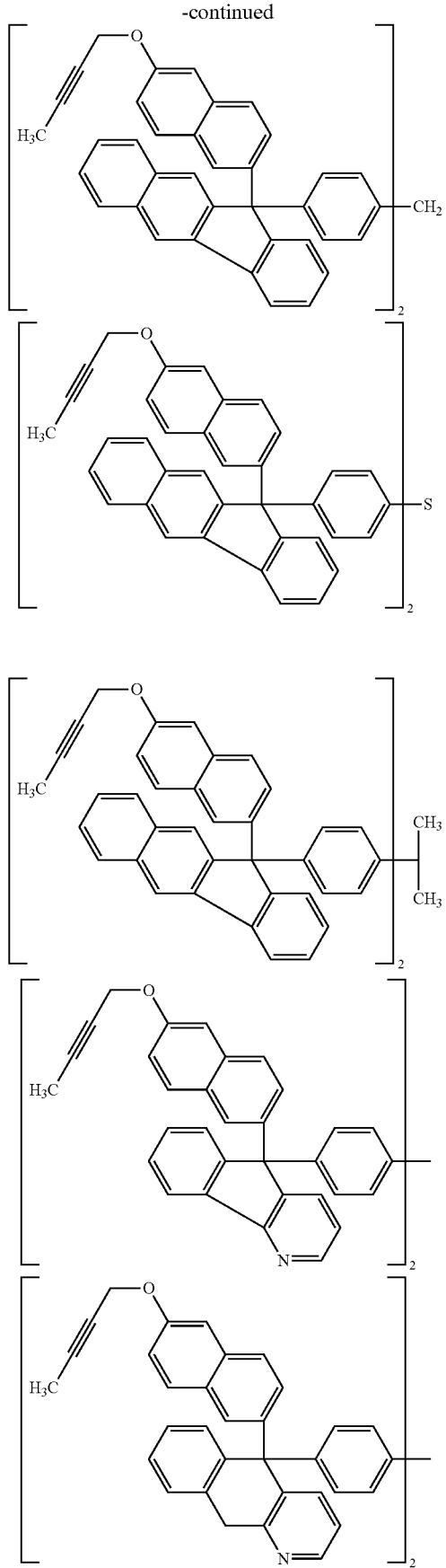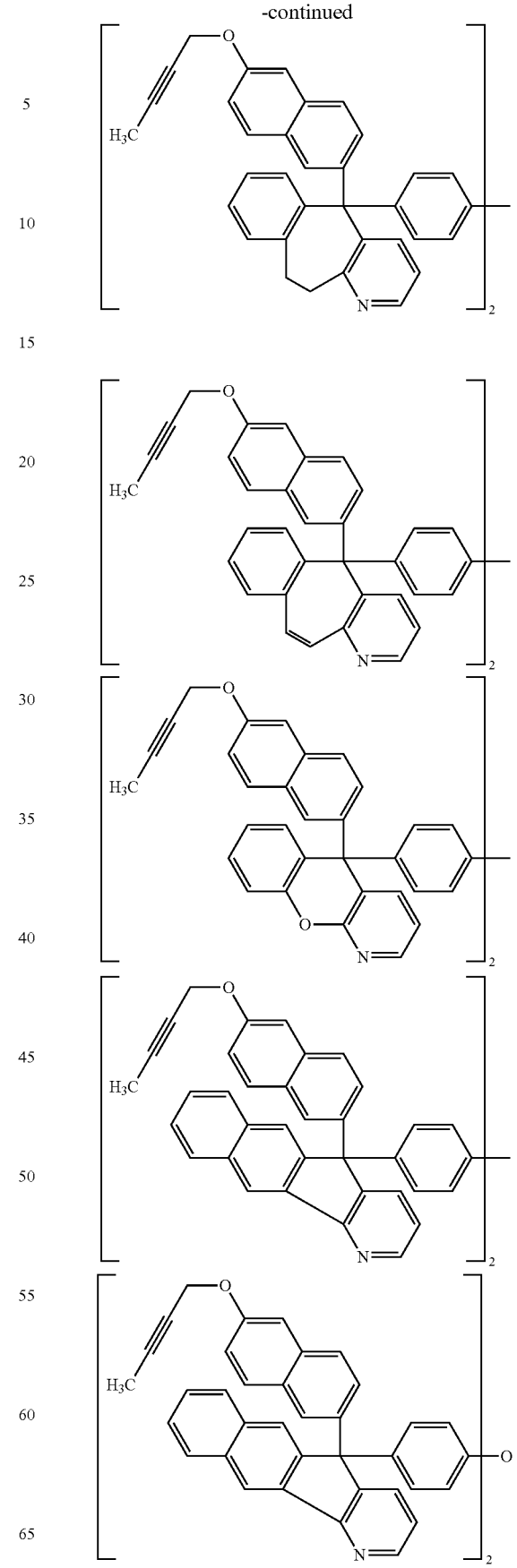

-continued
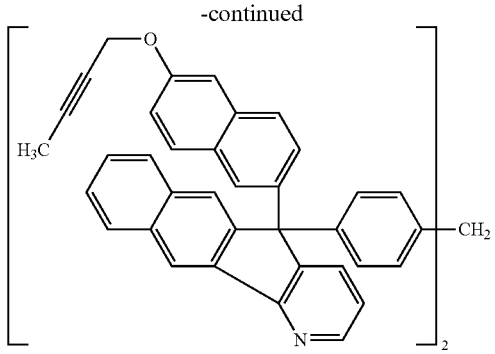
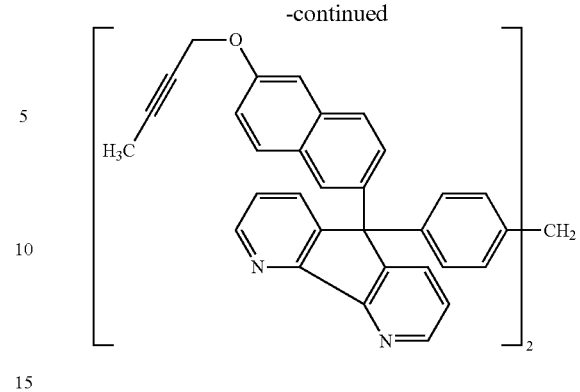
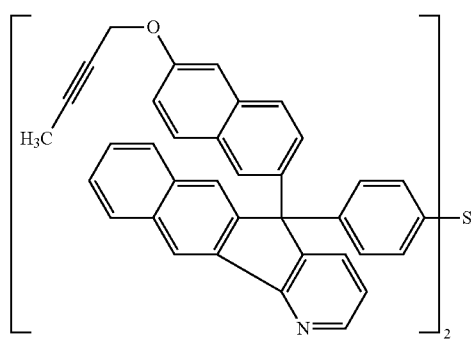
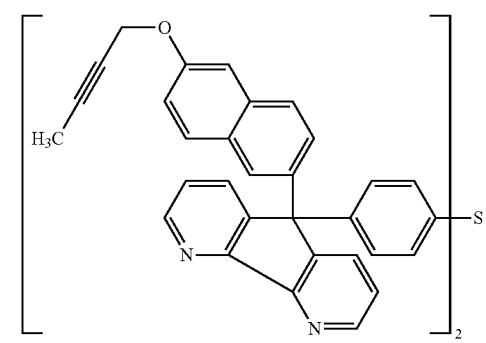
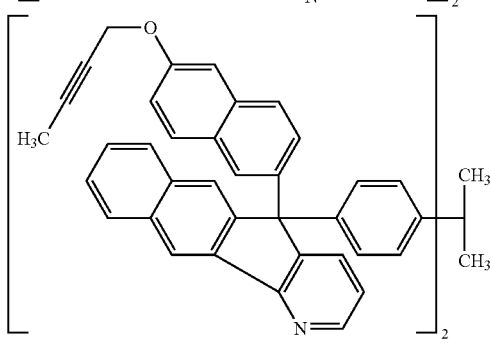
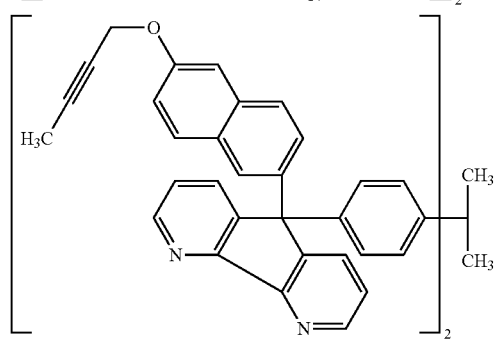
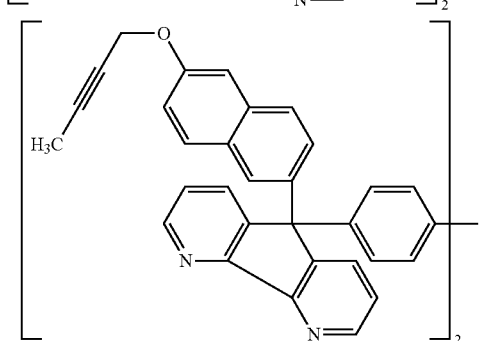
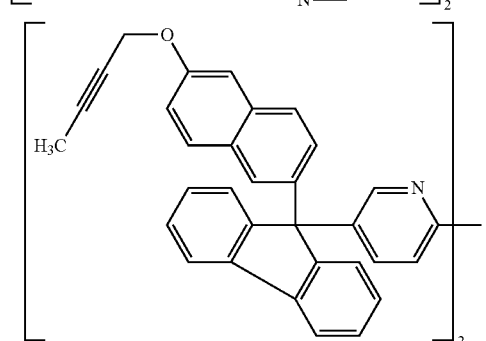
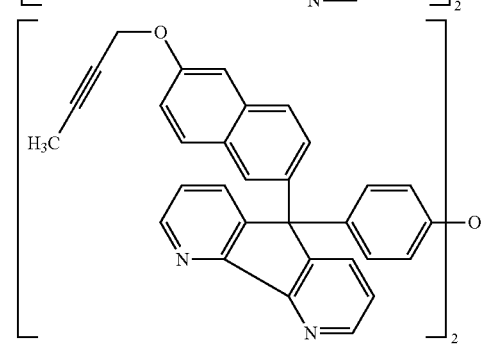
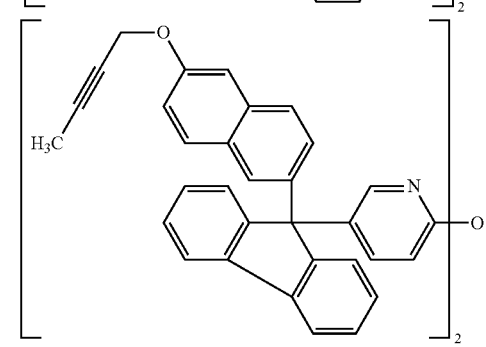

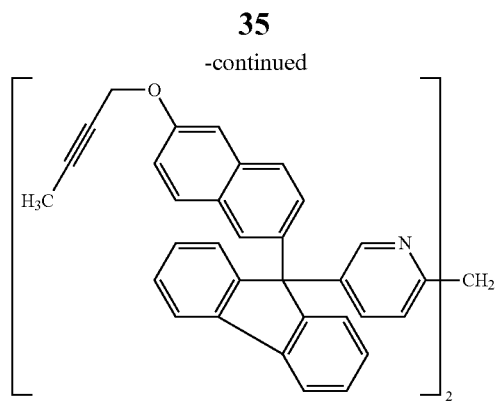
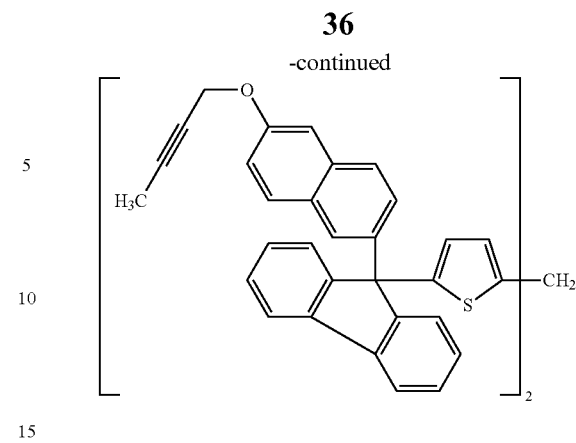
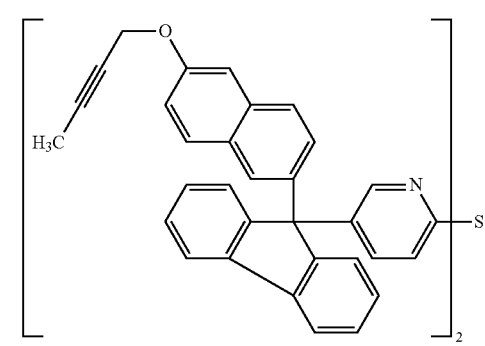
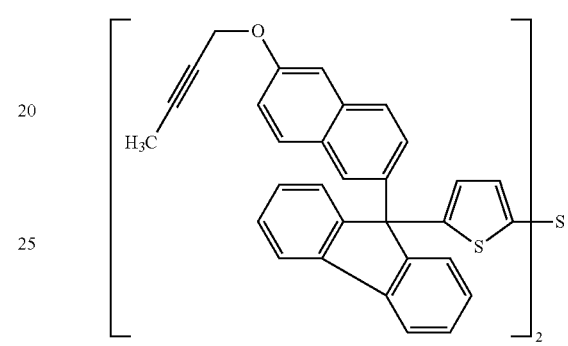
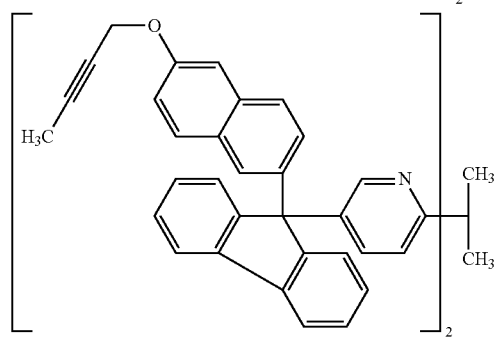
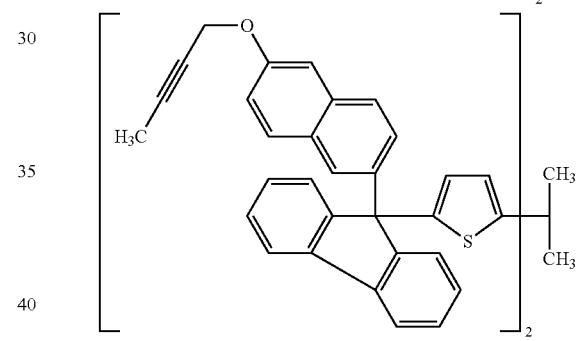
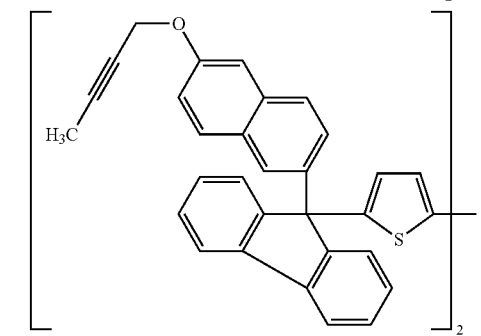
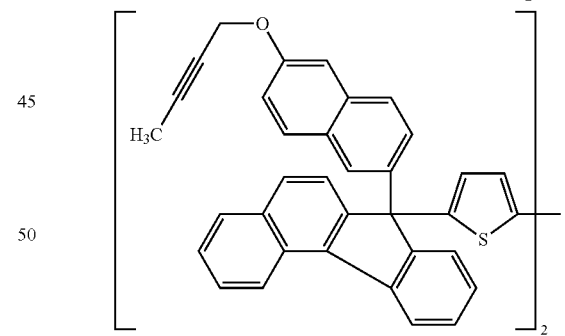
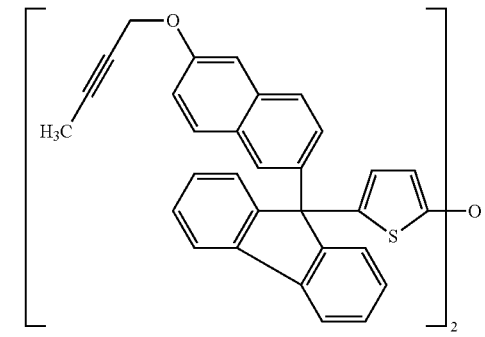
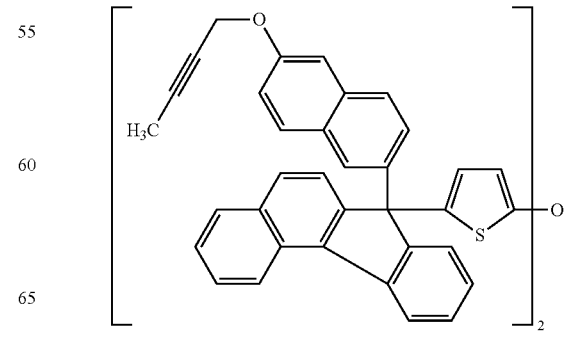

37
-continued
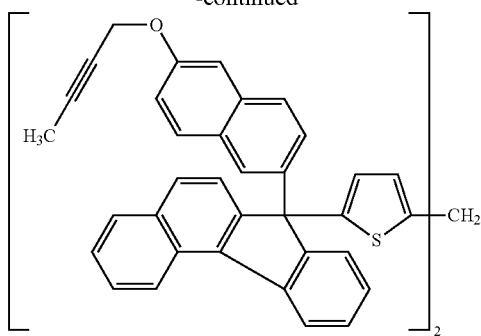
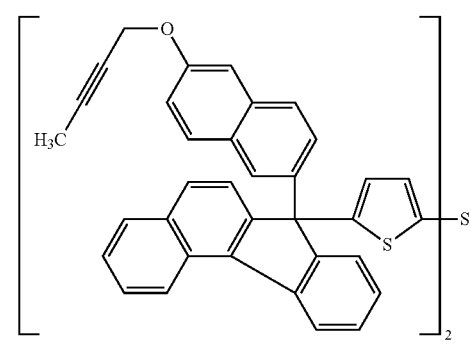
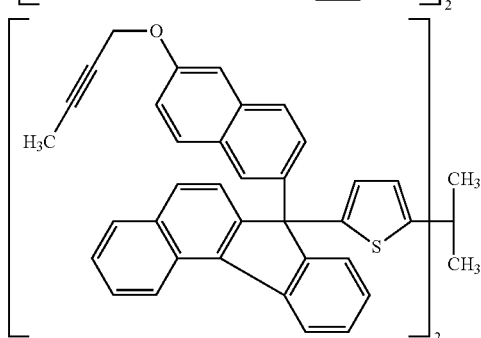
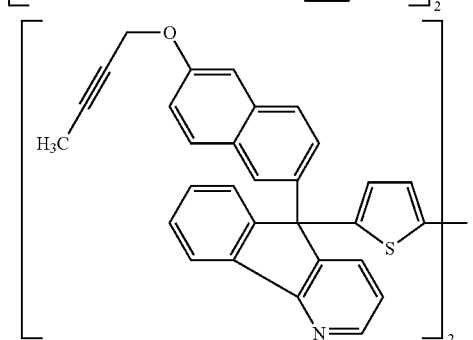
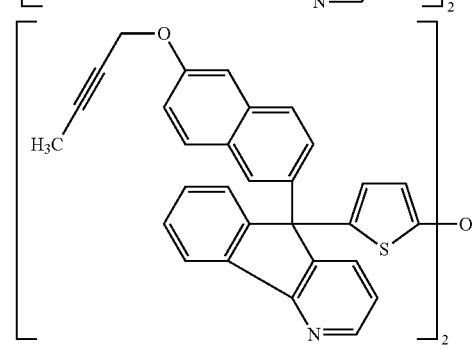
38
-continued
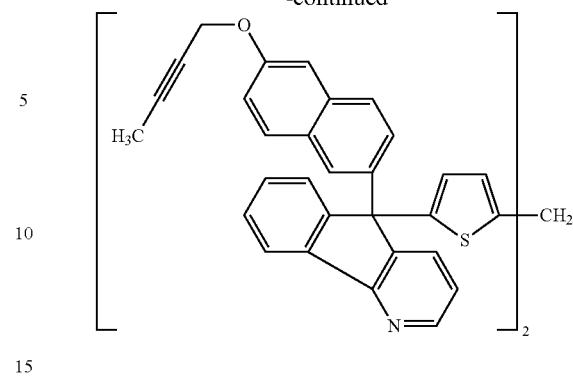
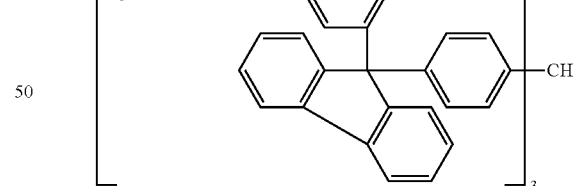
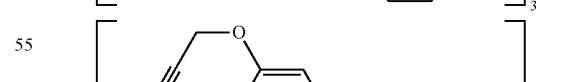
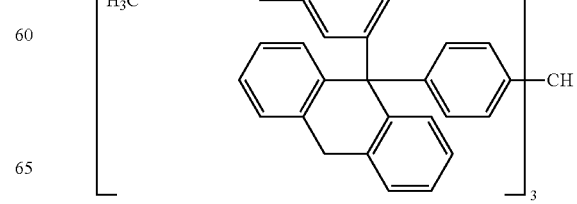
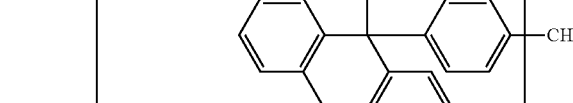
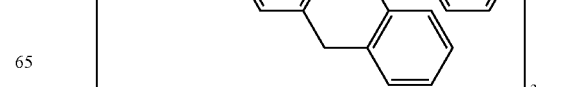

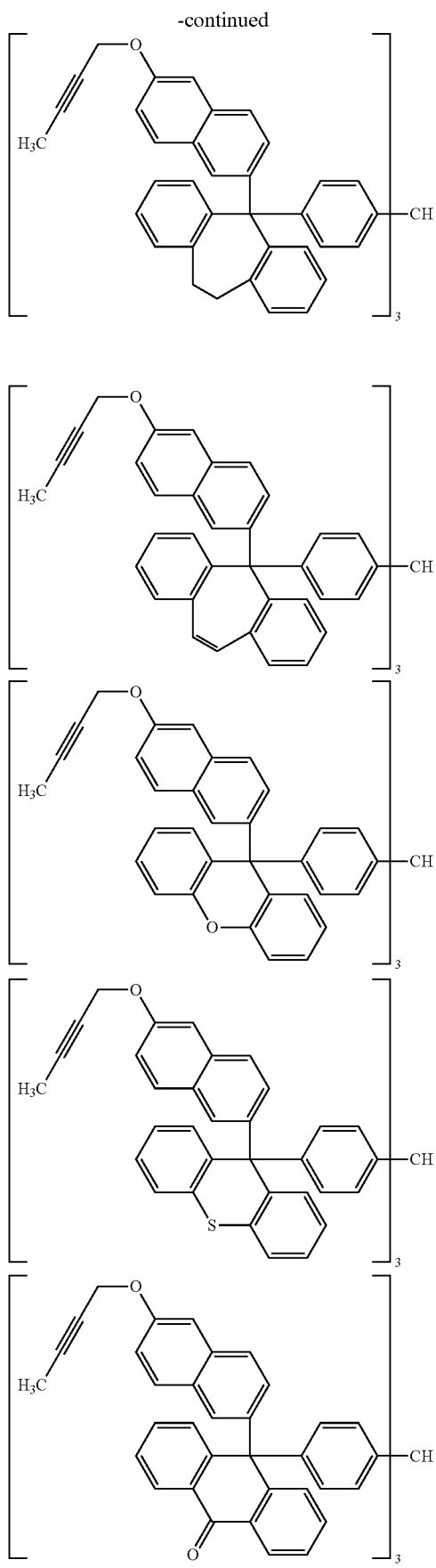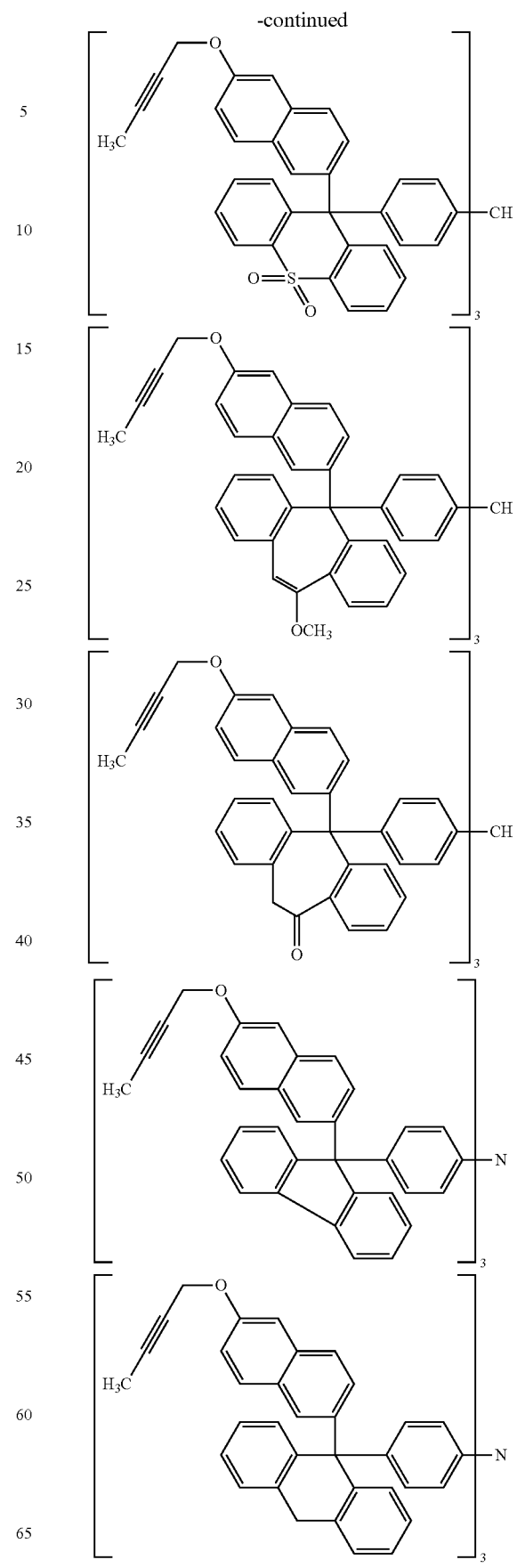

-continued
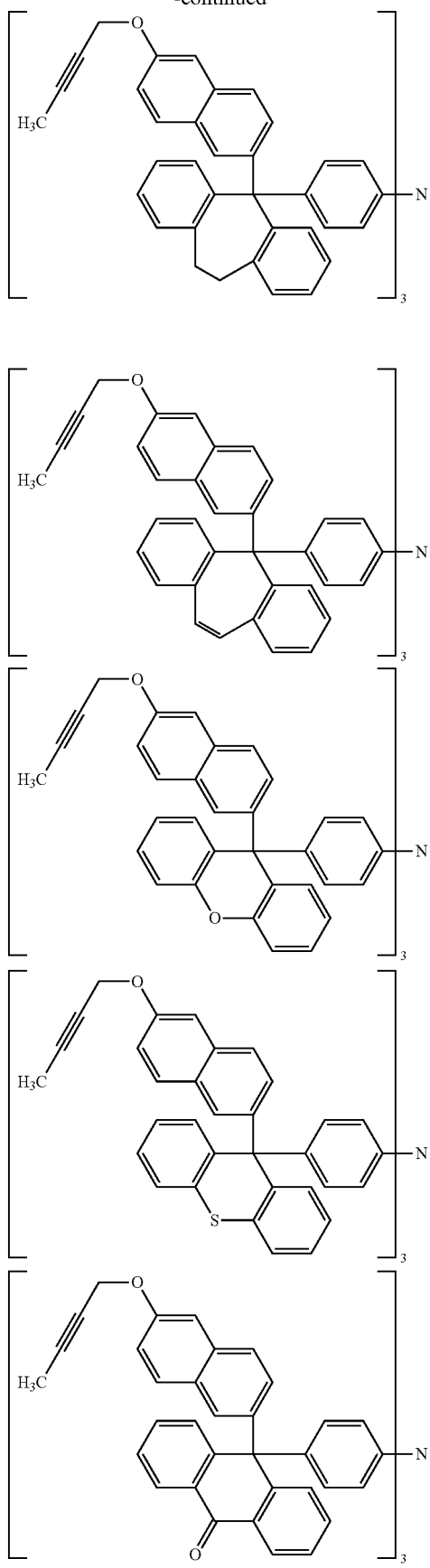
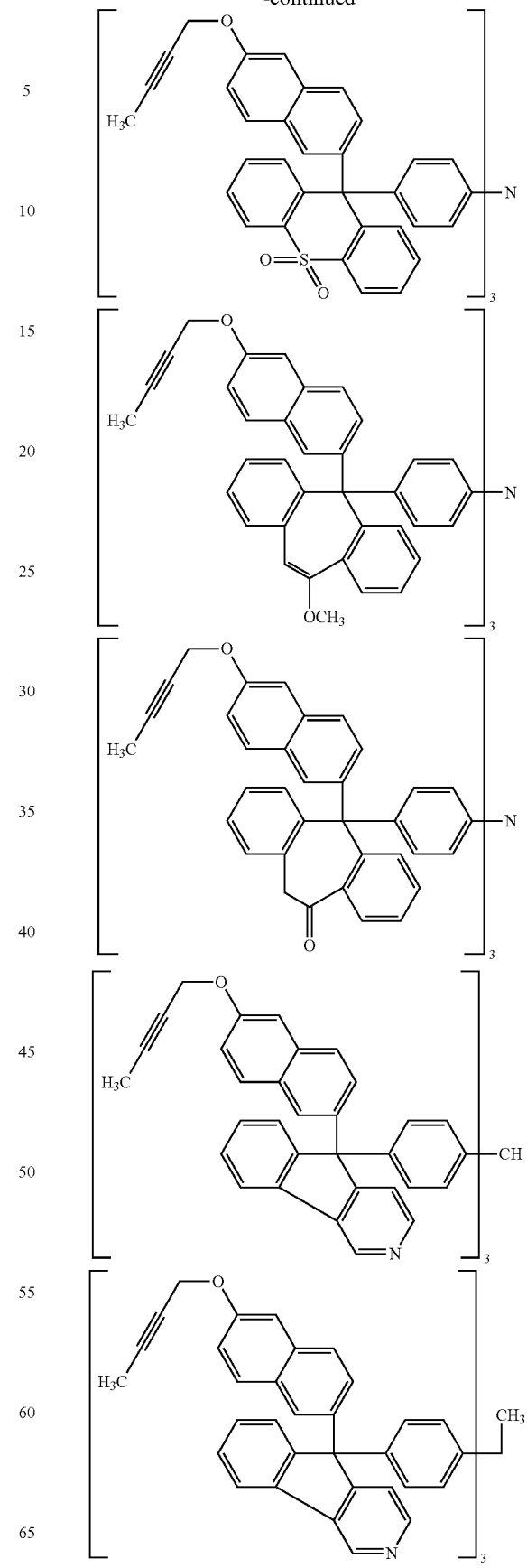

43
-continued
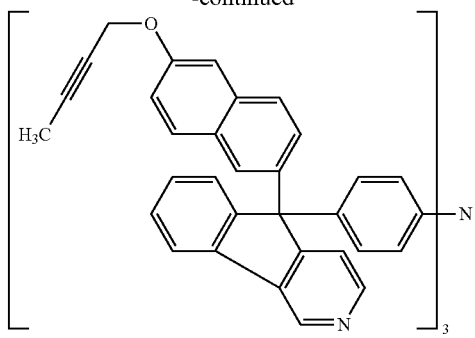
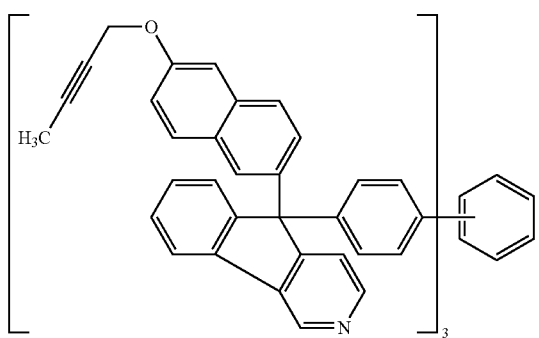
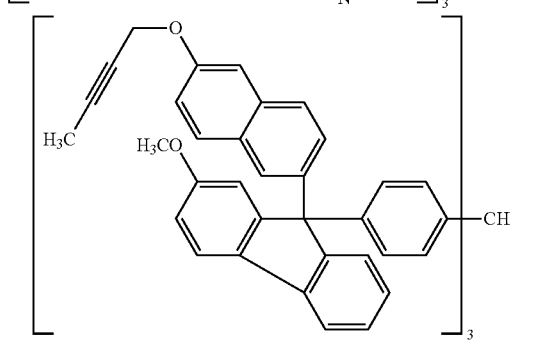
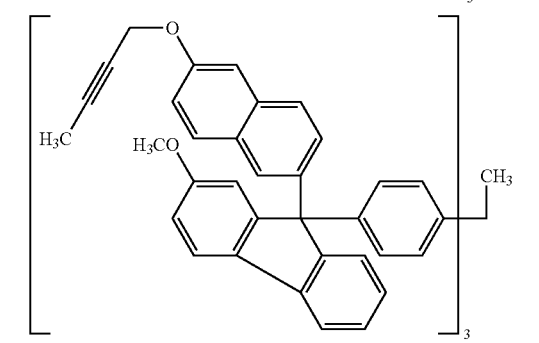
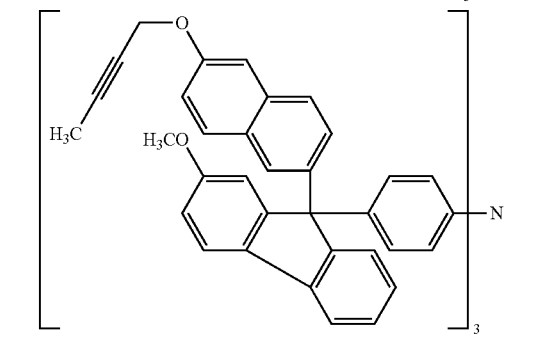
44
-continued
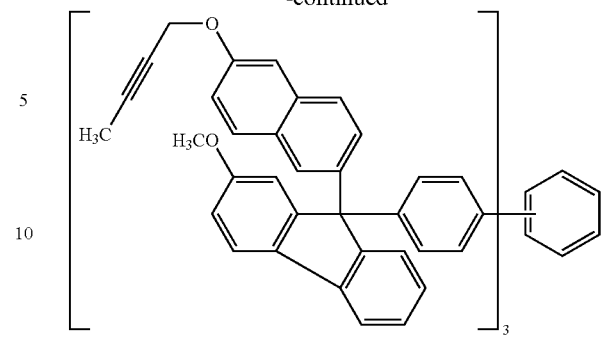
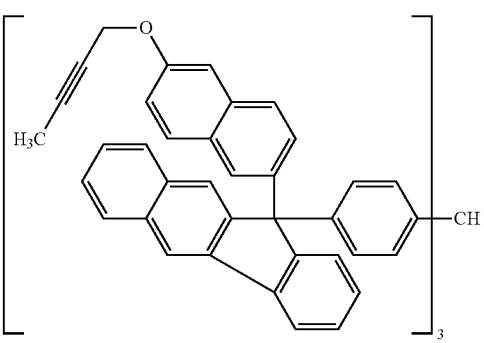
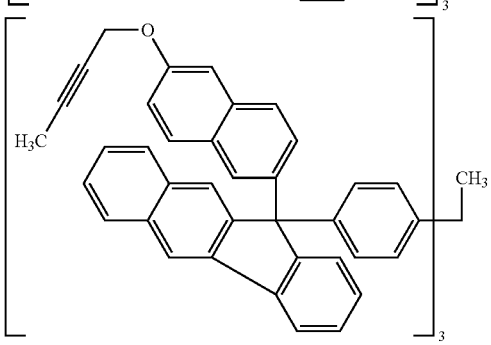
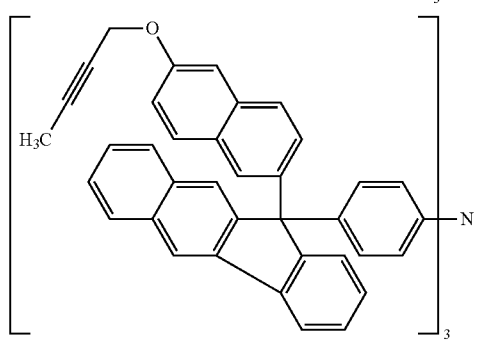
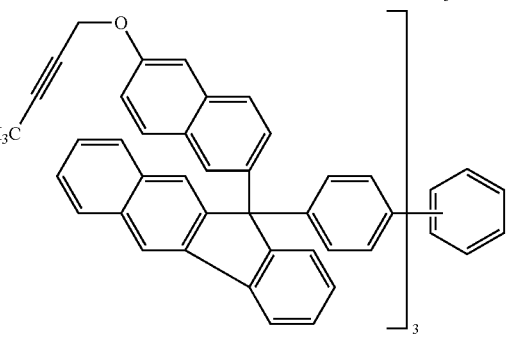

-continued
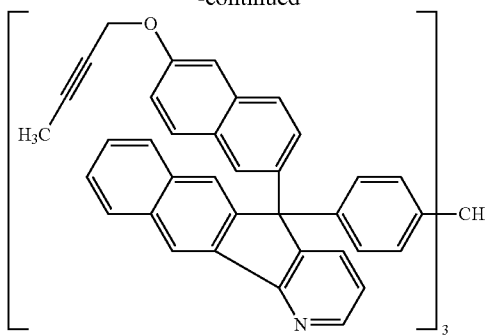
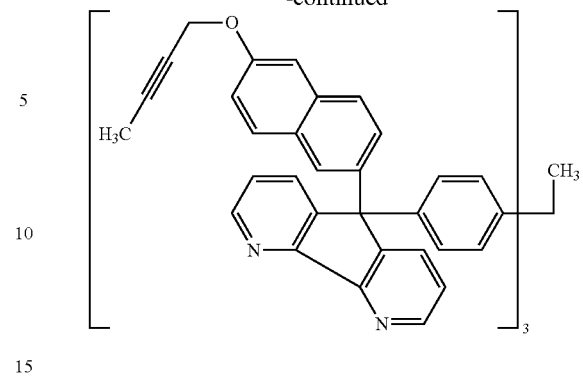
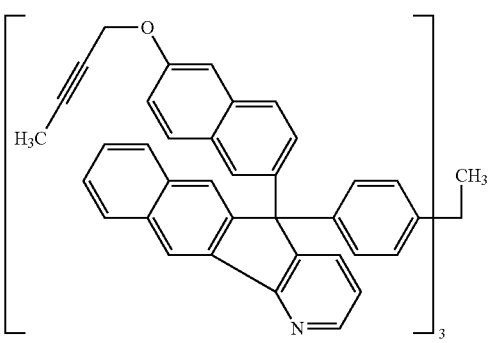
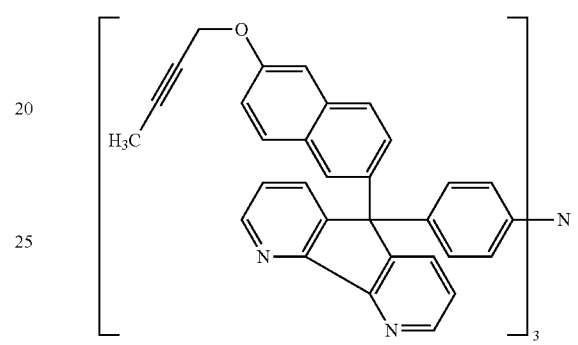
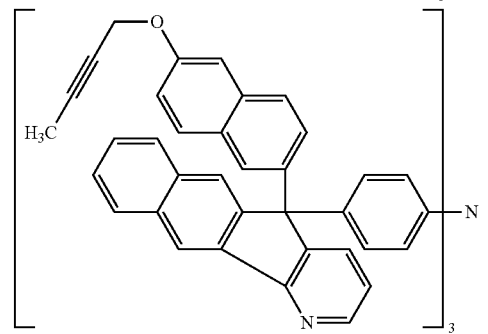
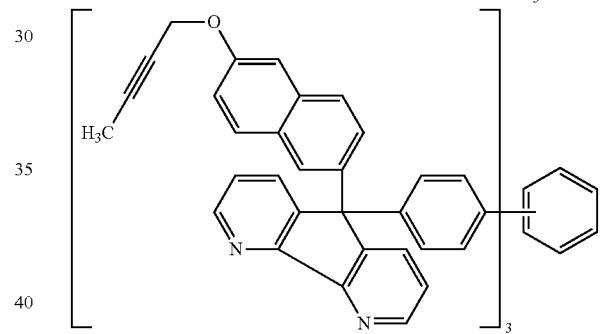
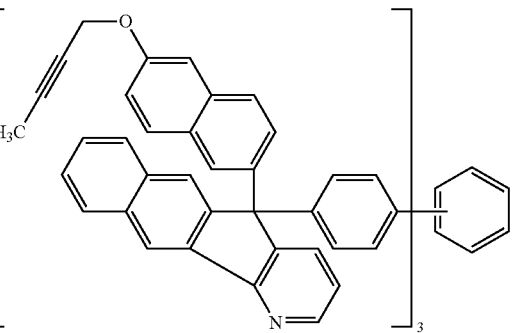
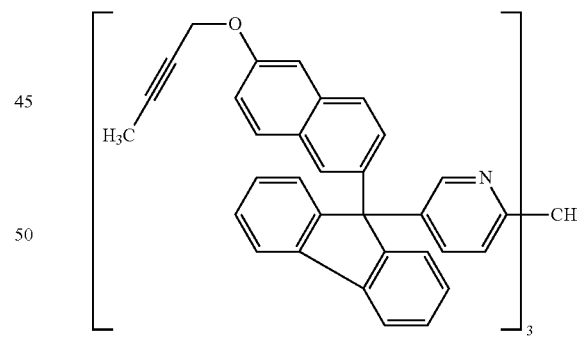
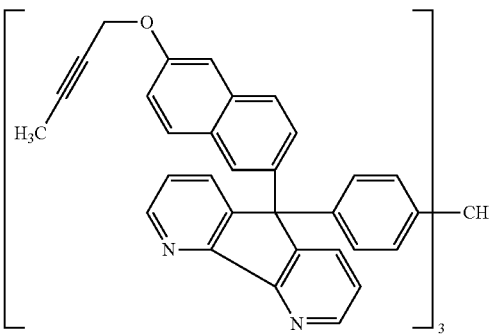
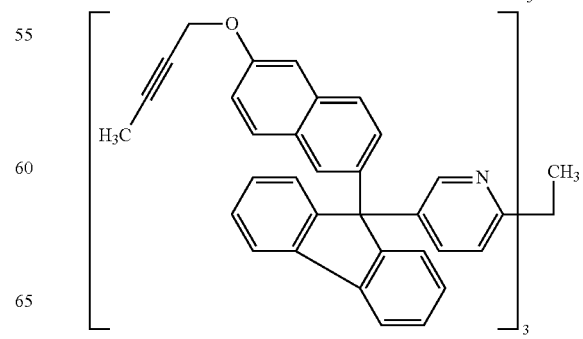

-continued
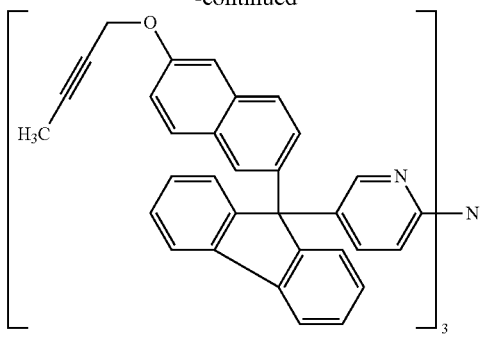 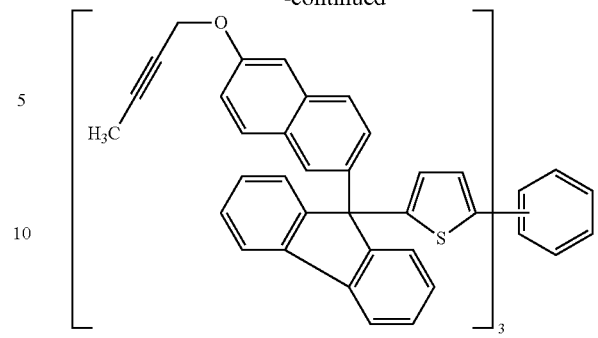
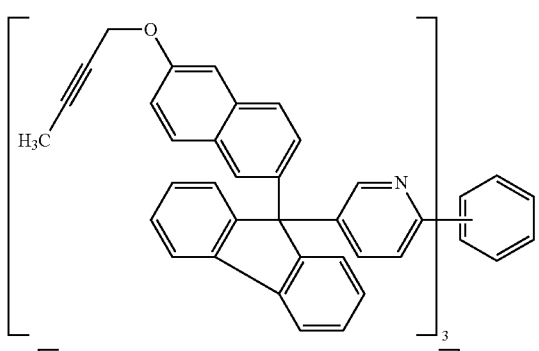 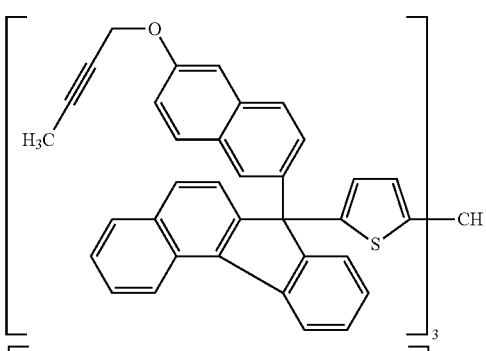
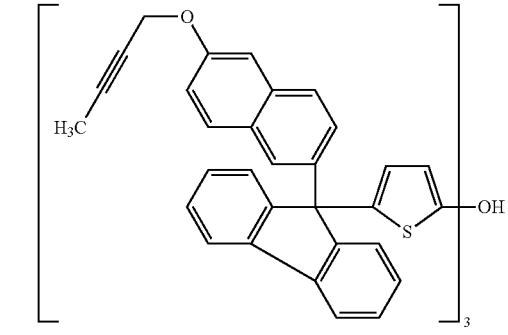 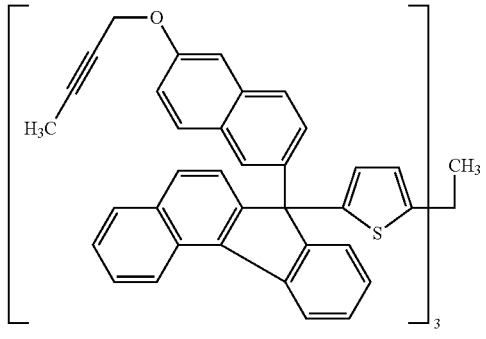
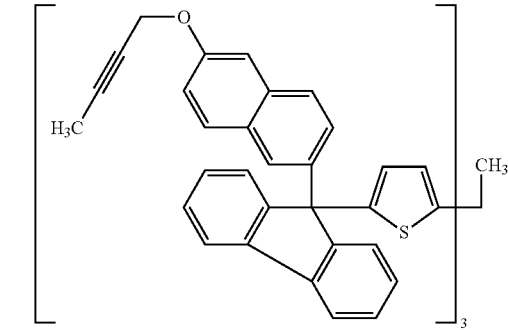 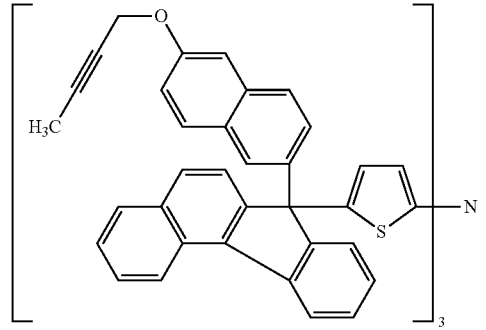
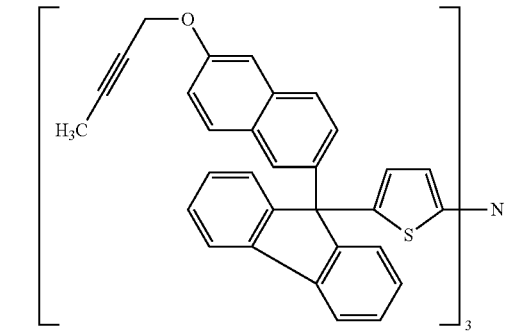 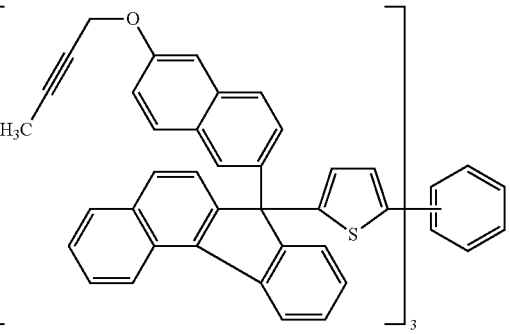

-continued
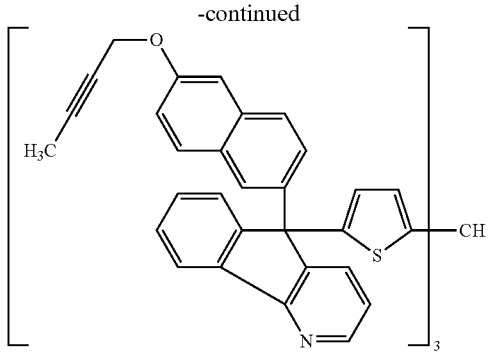
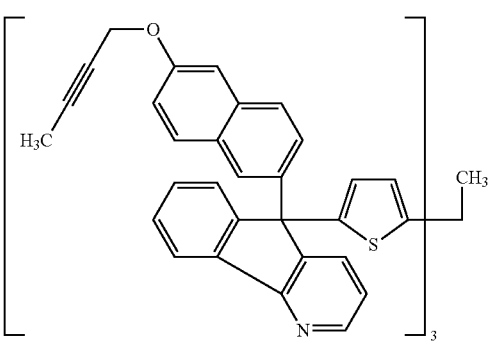
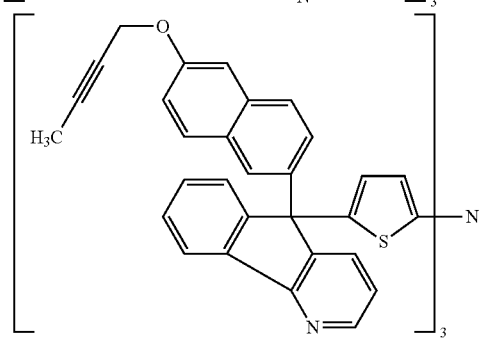
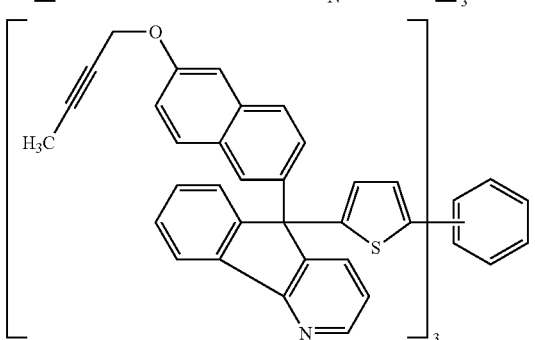
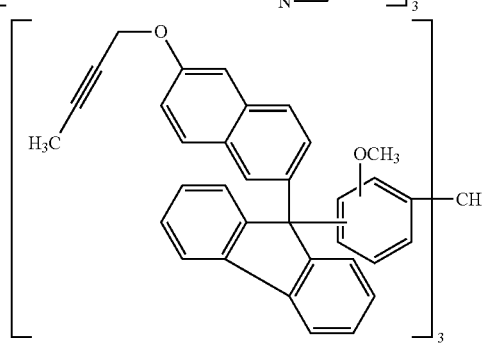
-continued
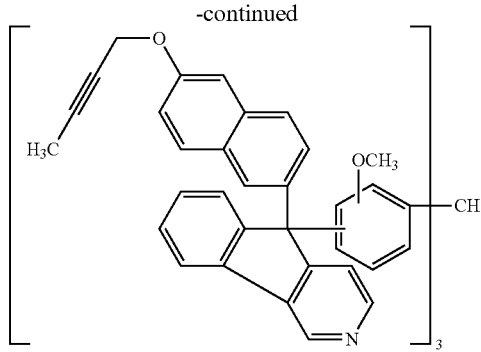
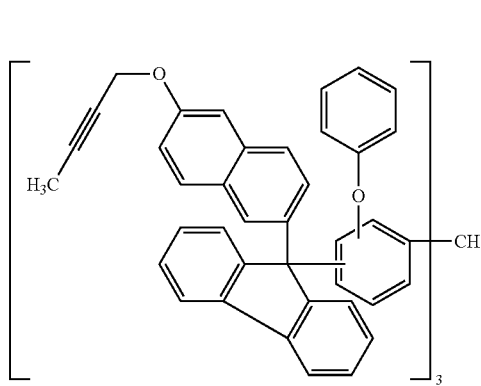
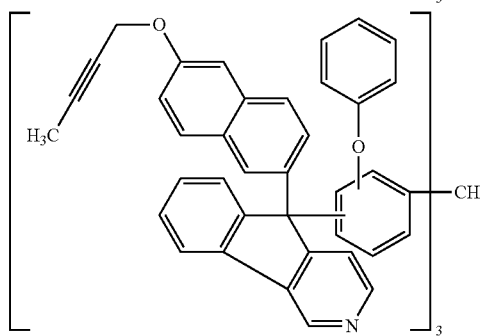
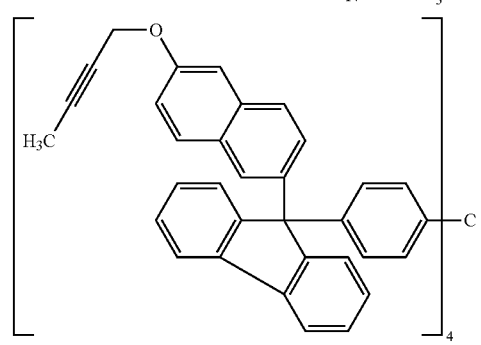
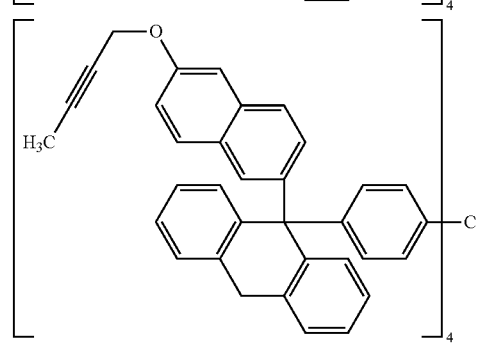

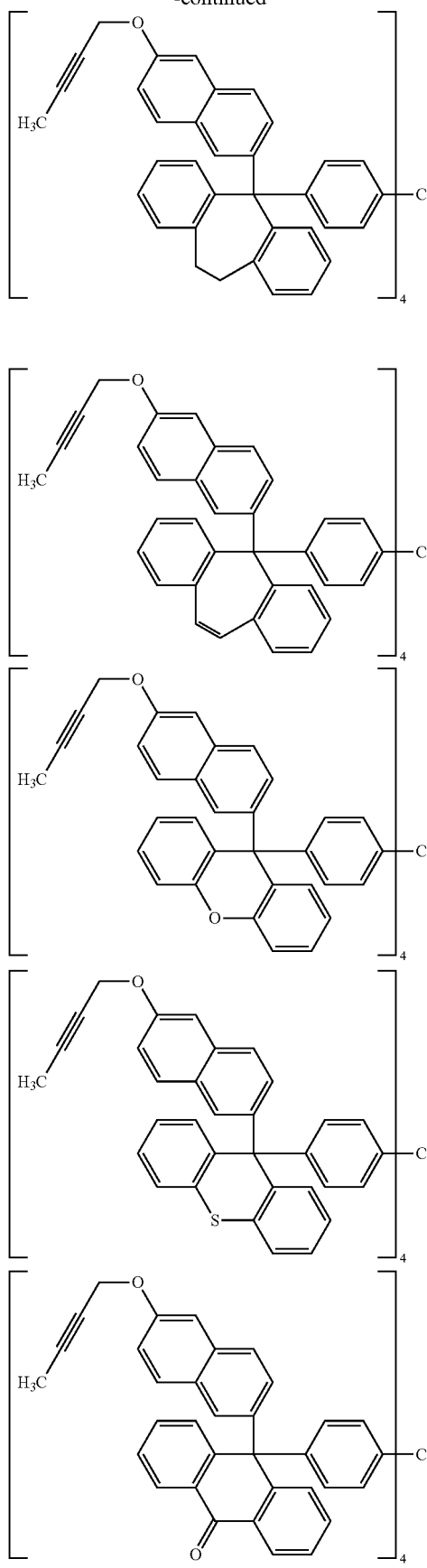
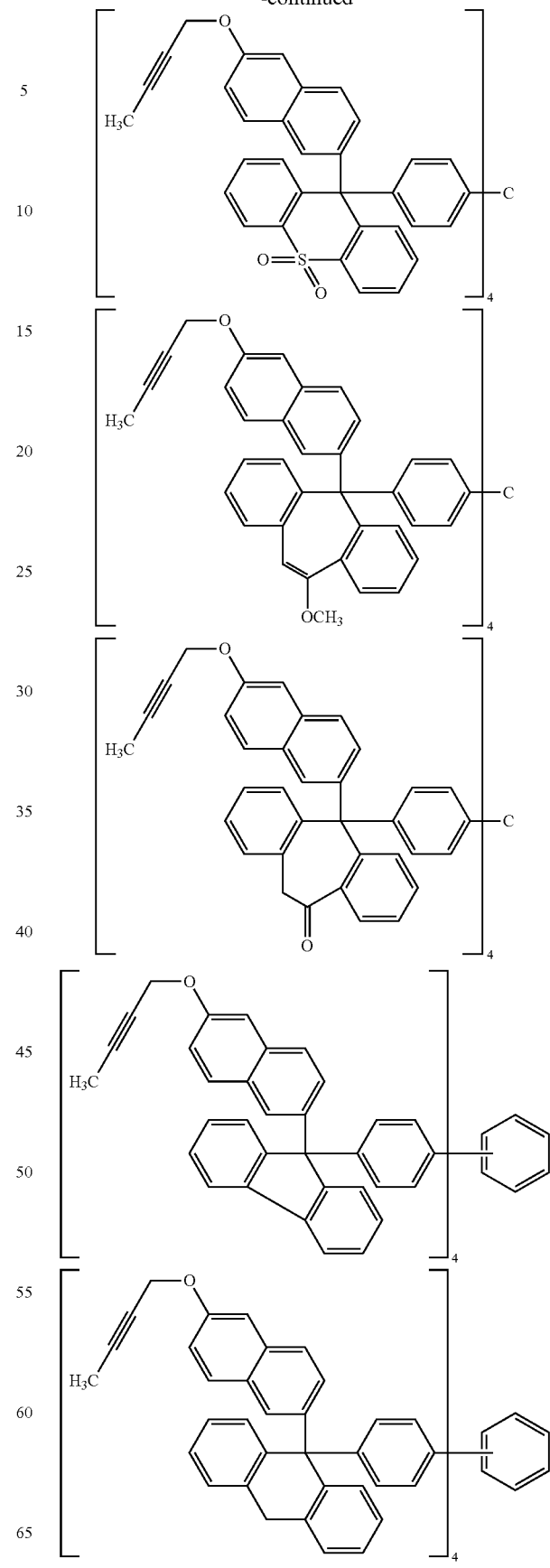

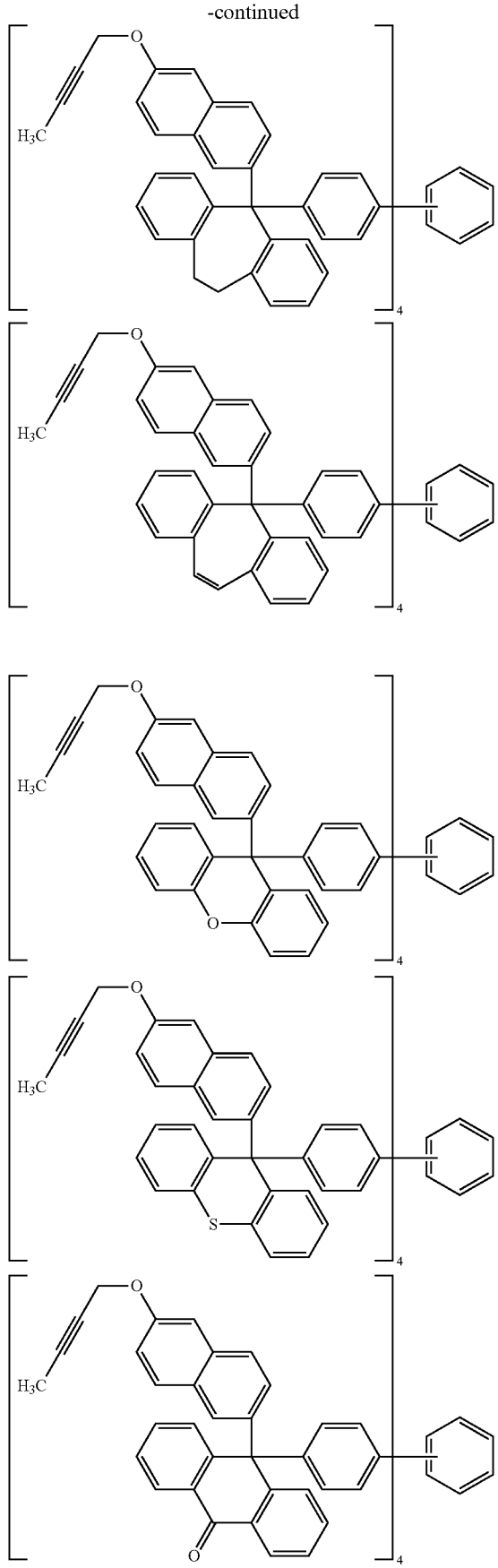
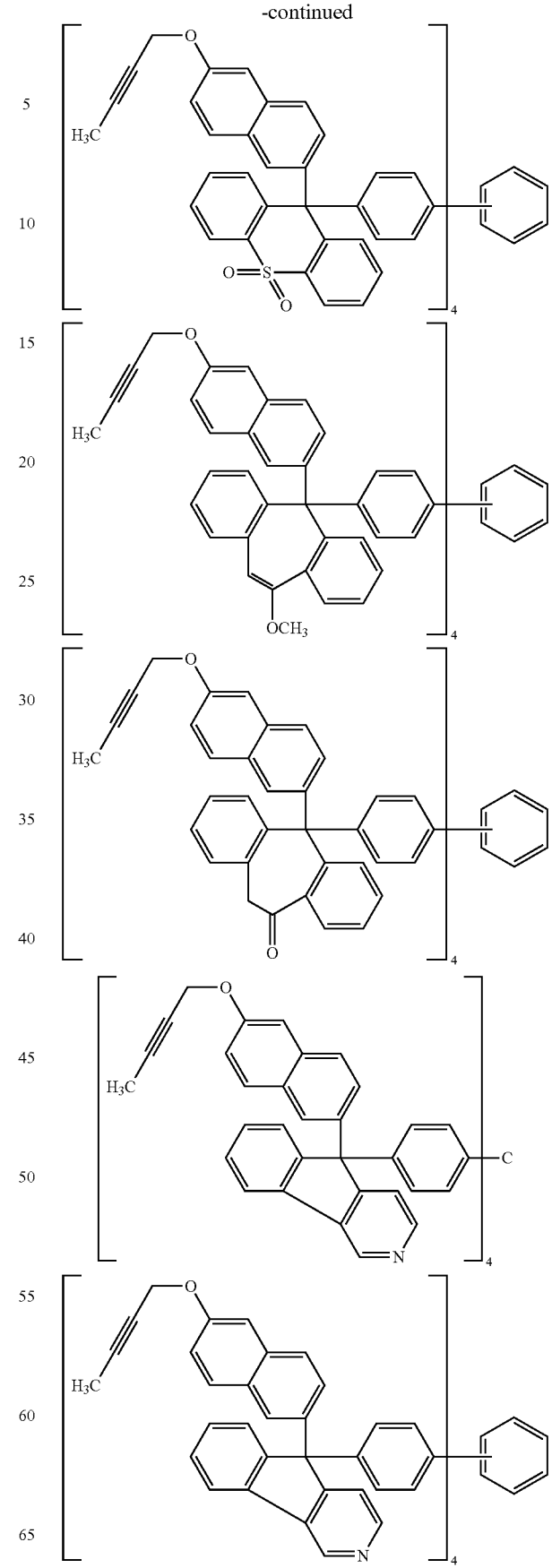

55
-continued
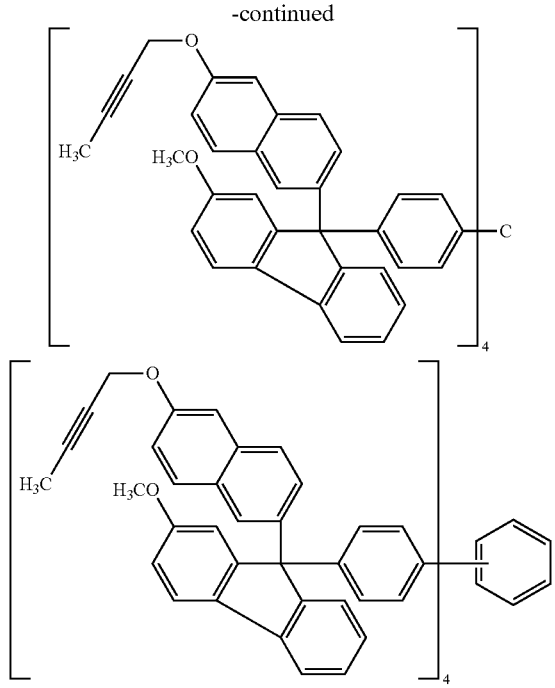
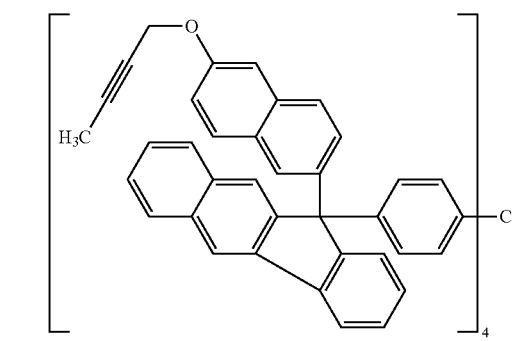
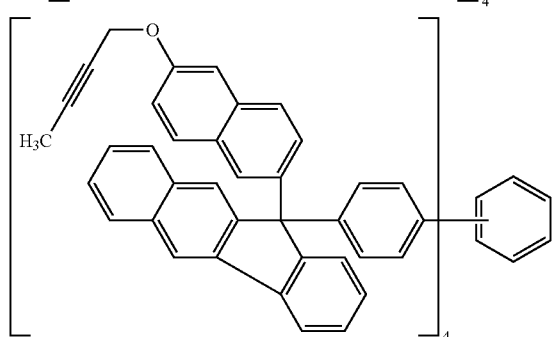
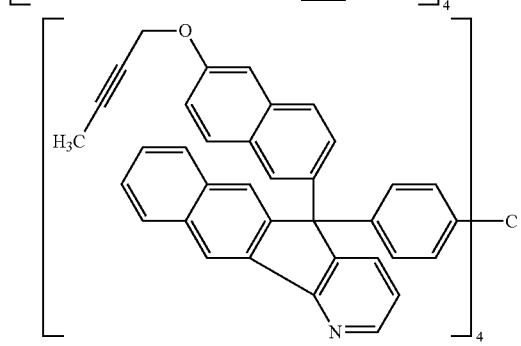
56
-continued
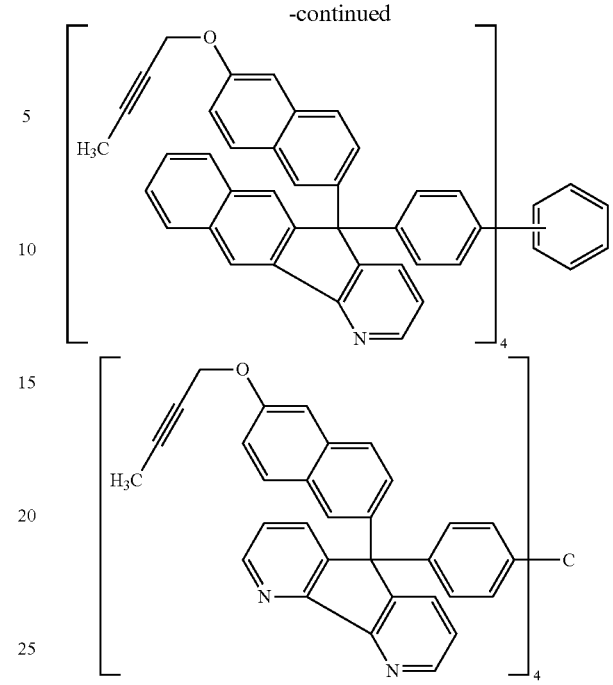
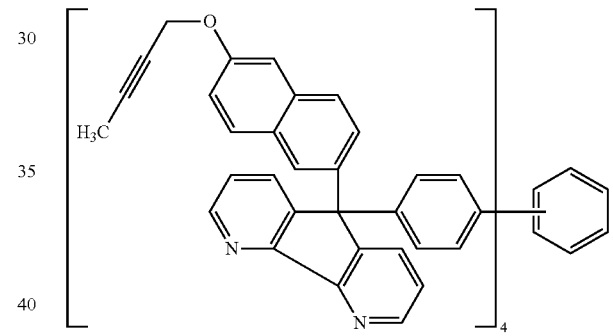
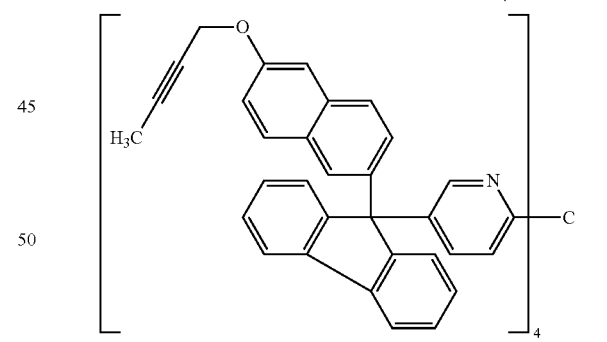
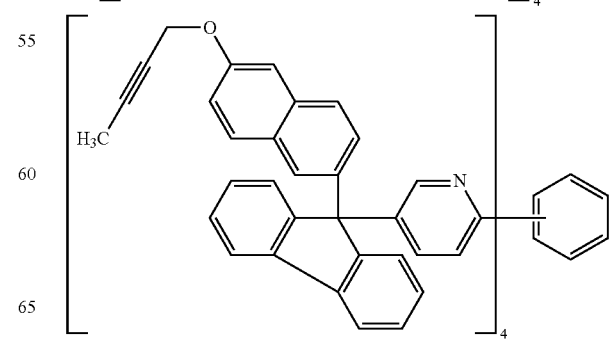

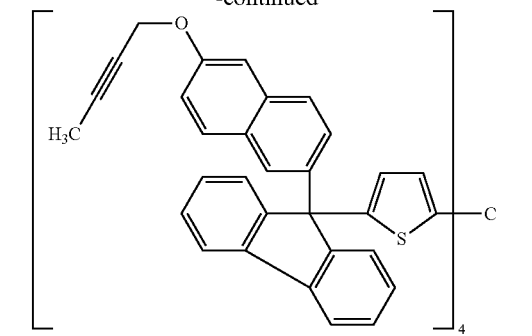
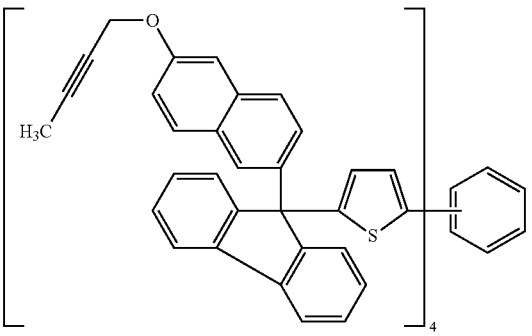
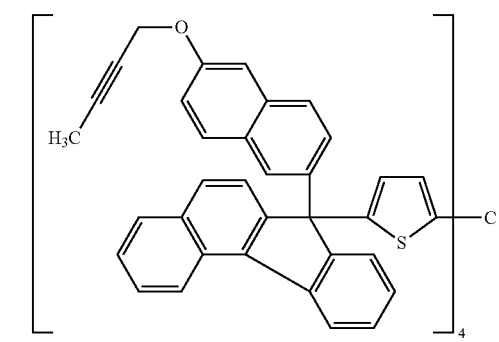
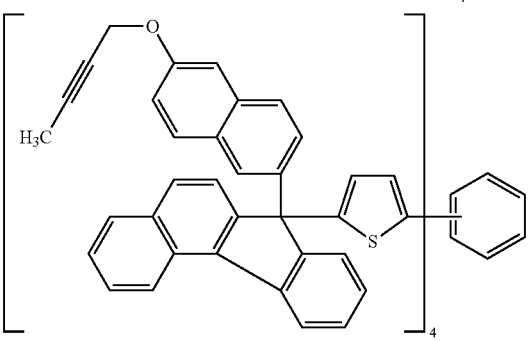
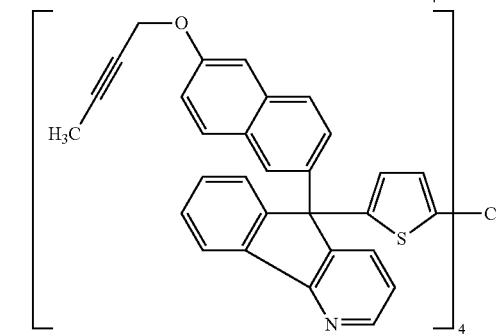
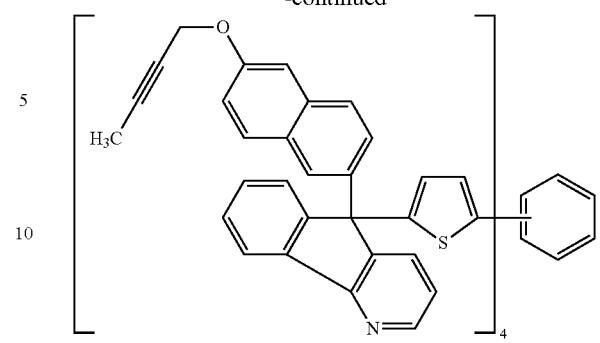
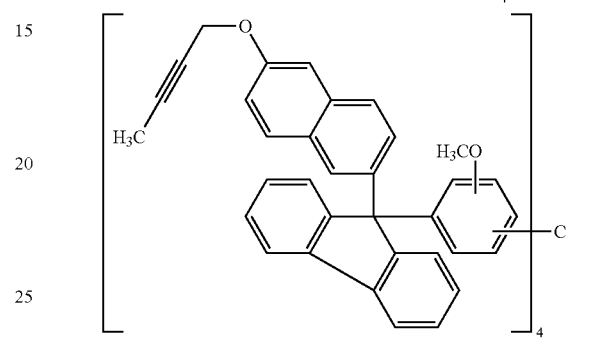
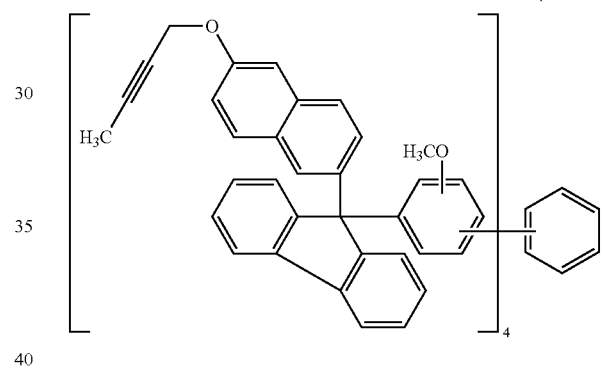
The Compound (3) shown by the following general formula (1-3) is also in a preferable structure. Illustrative examples of the Compound (3) includes the following, but are not limited thereto.
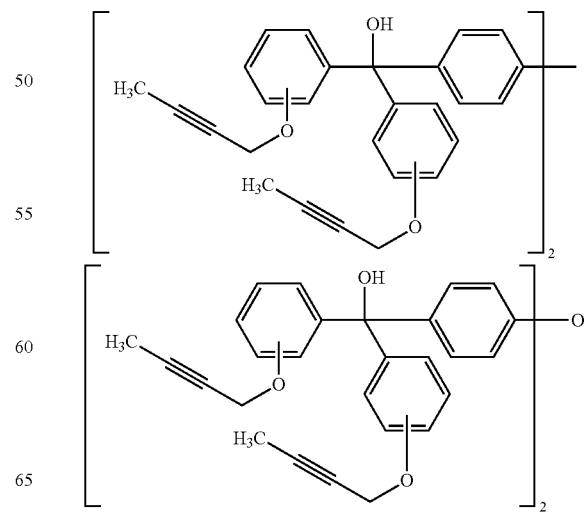

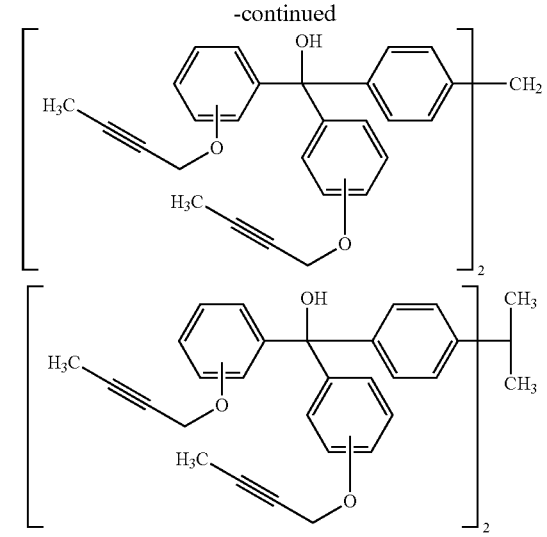
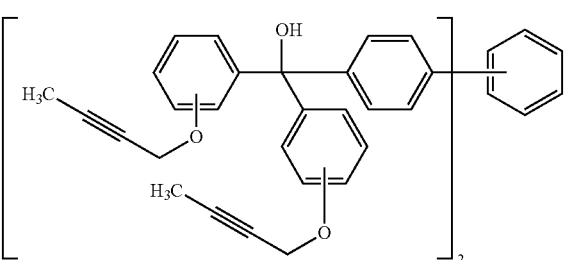
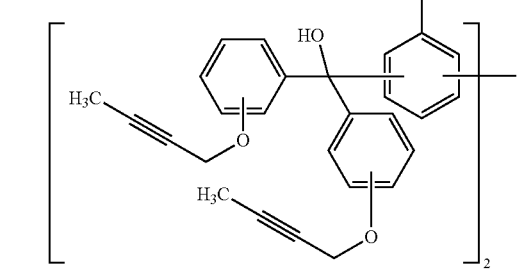
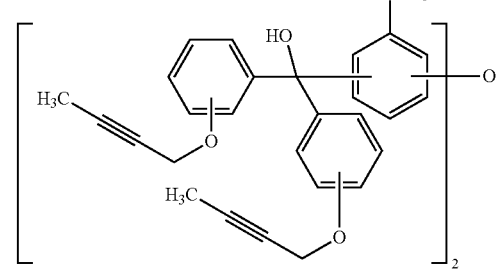
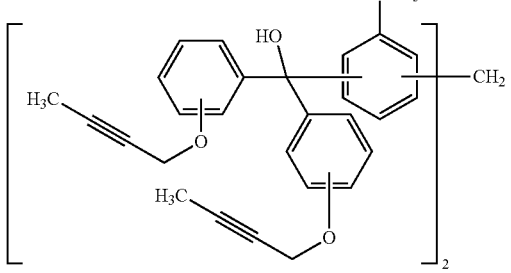
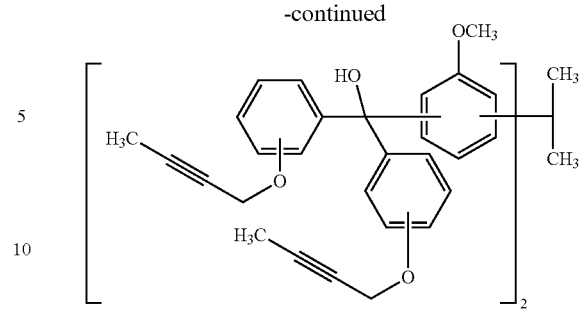
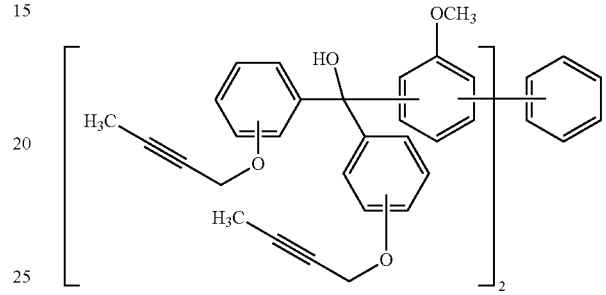
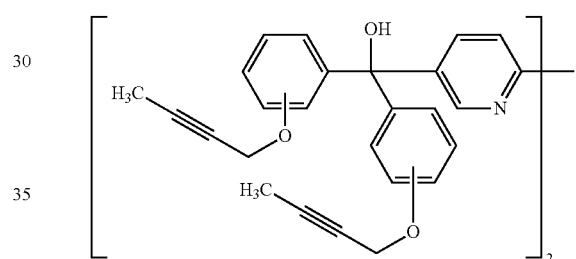
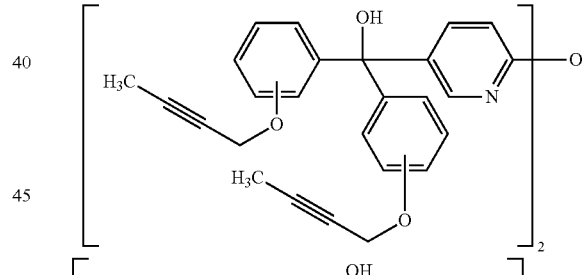
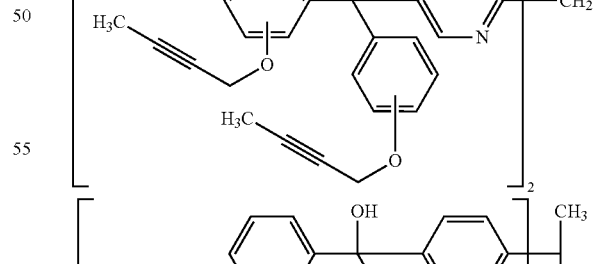
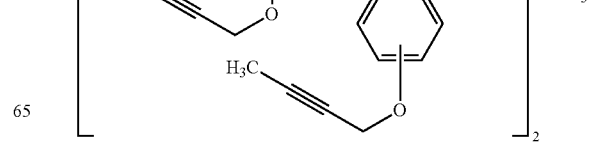

61
-continued
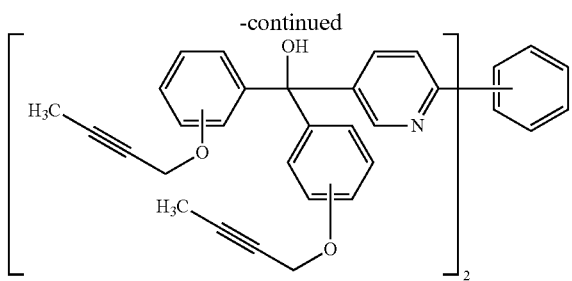
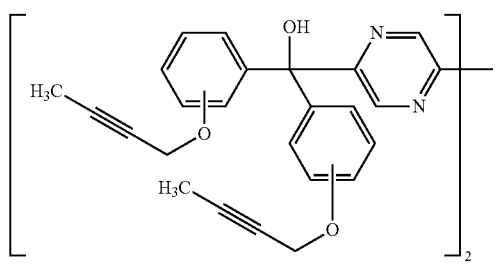
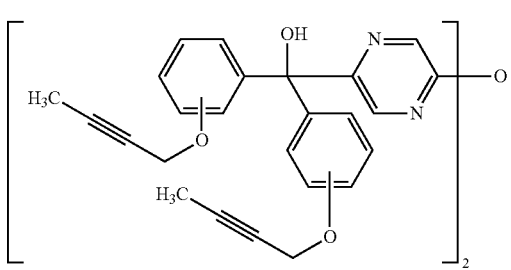
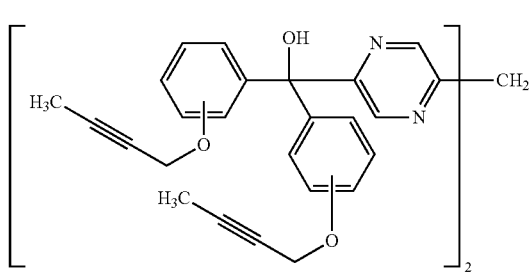
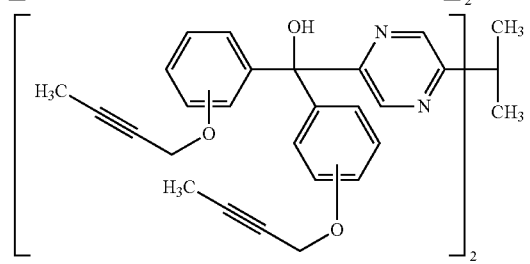
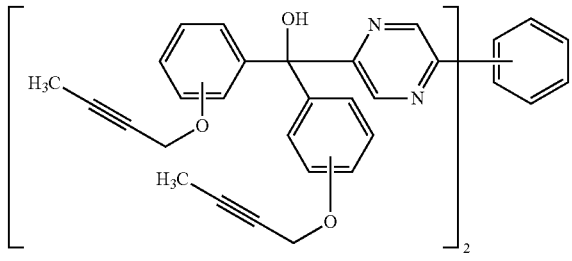
62
-continued
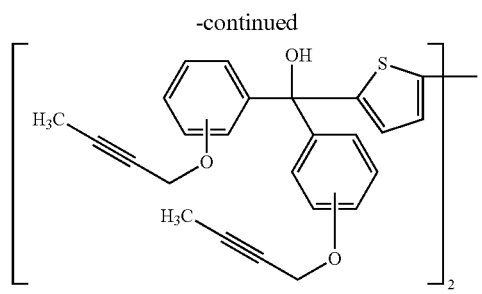
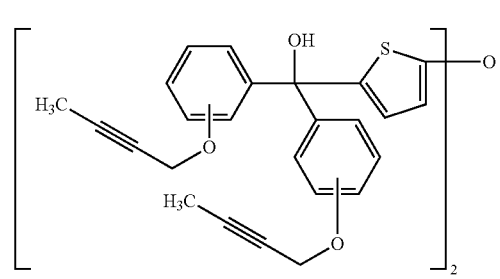
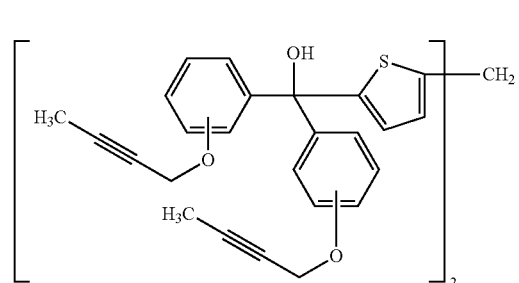
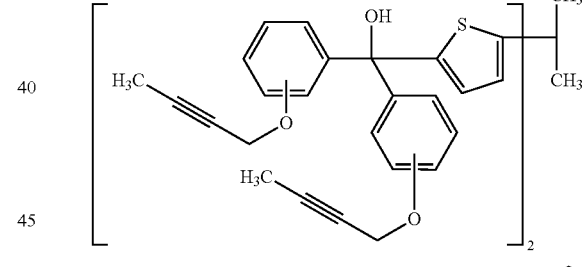
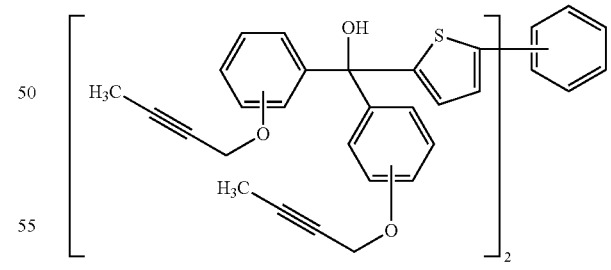
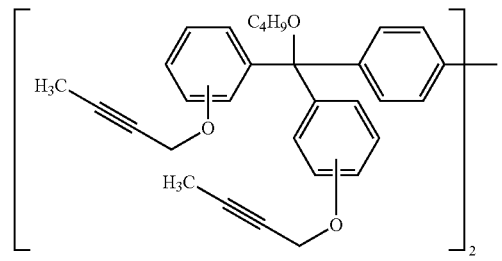

-continued
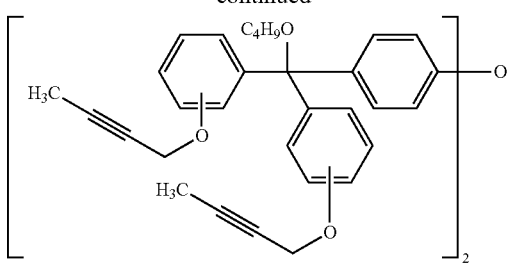
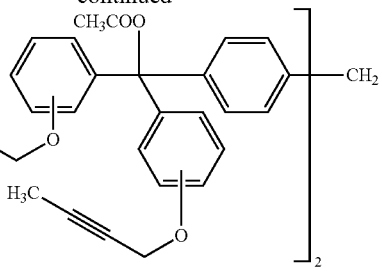
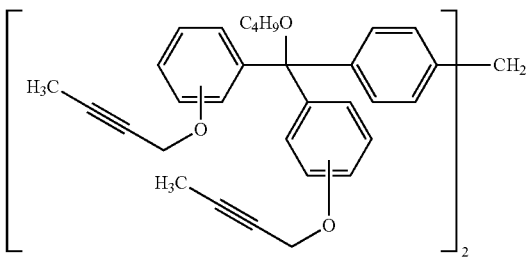
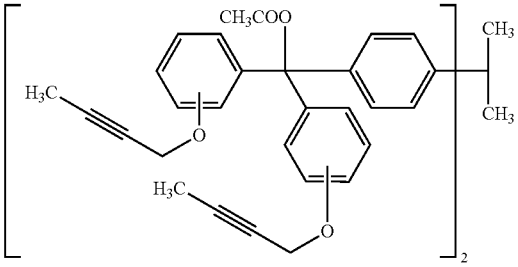
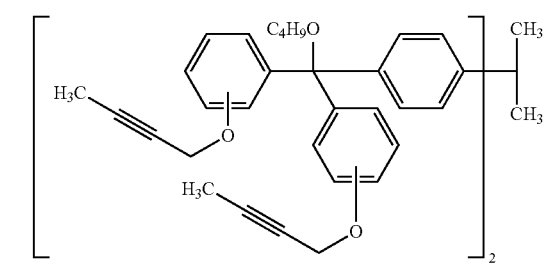
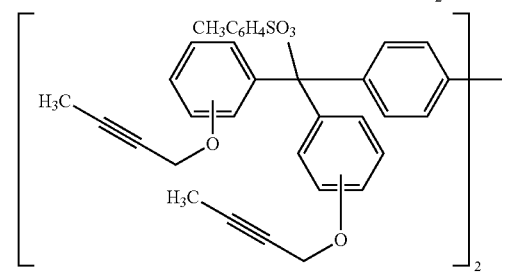
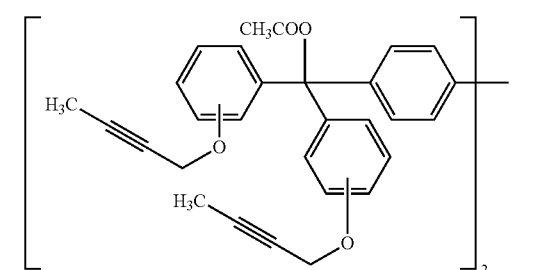
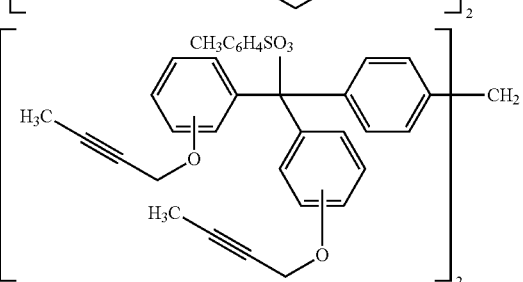

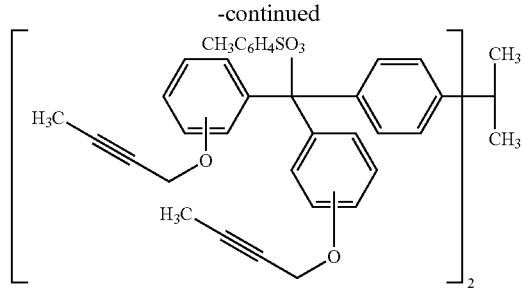
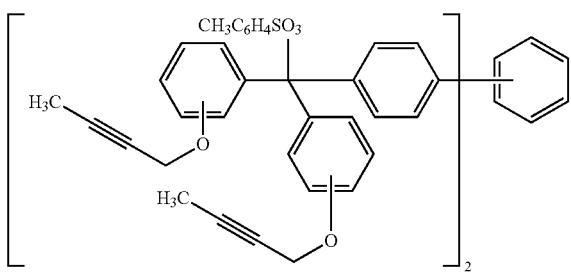
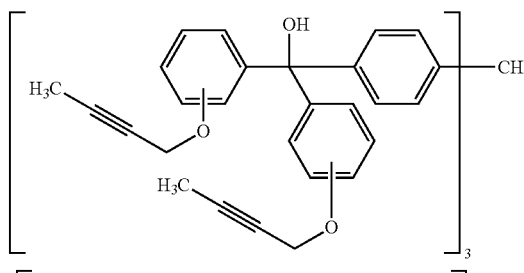
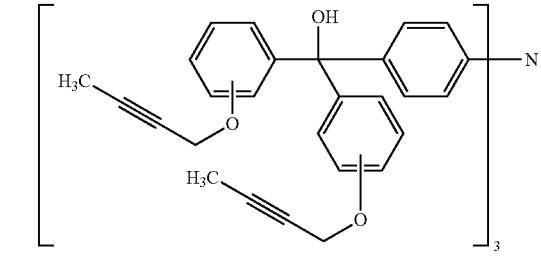
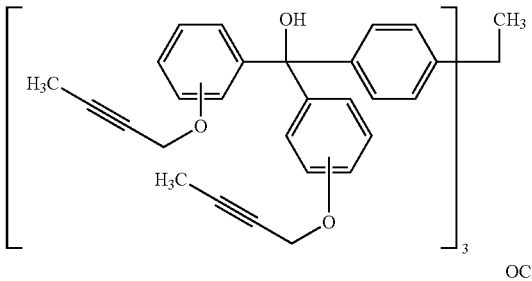
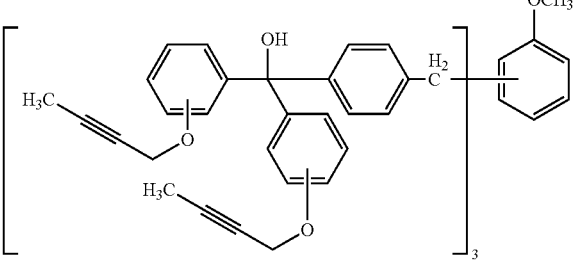
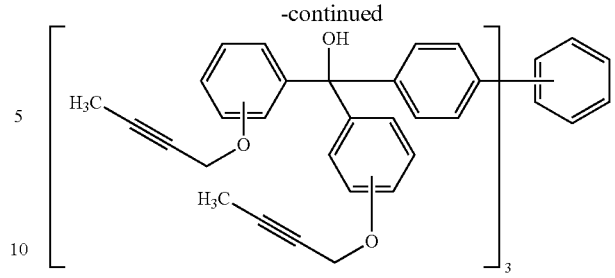
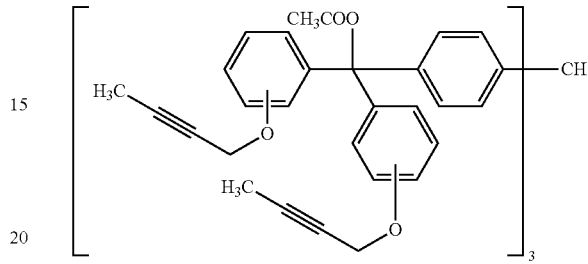
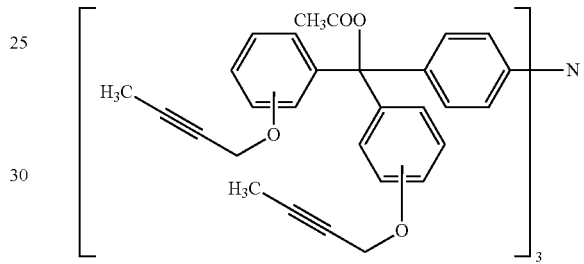
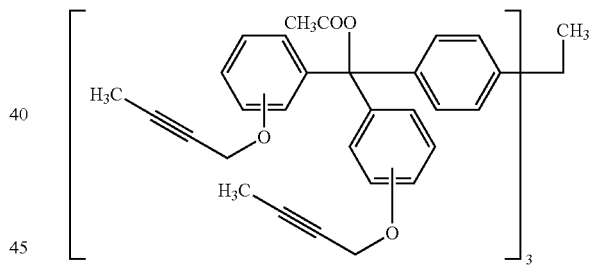
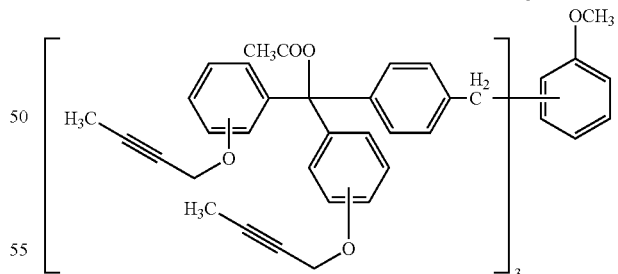
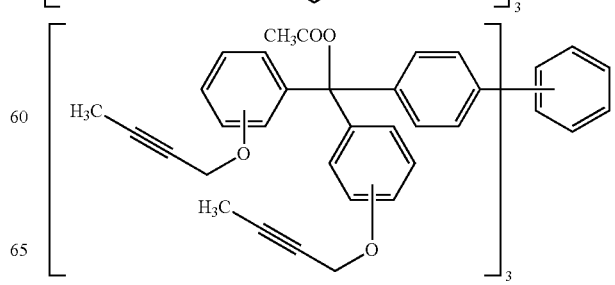

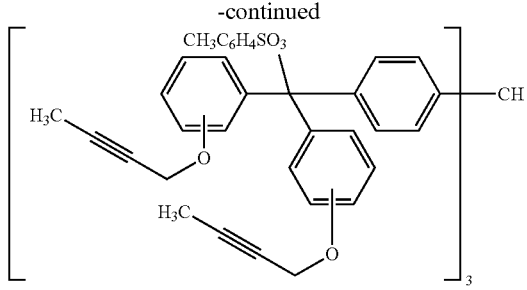
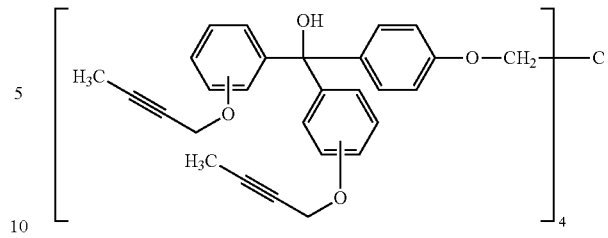
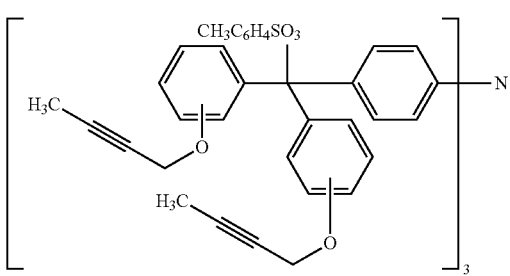
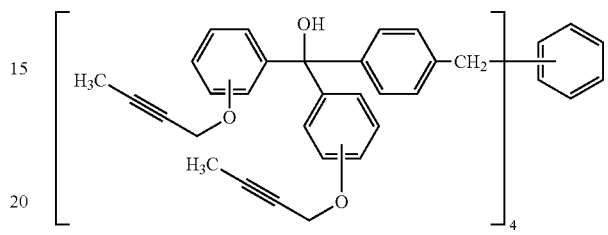
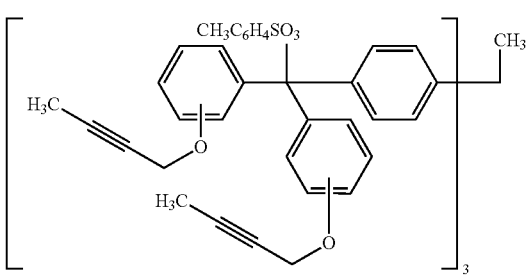
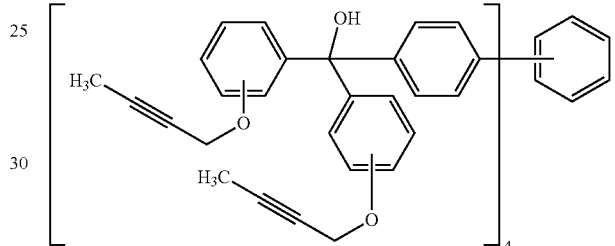
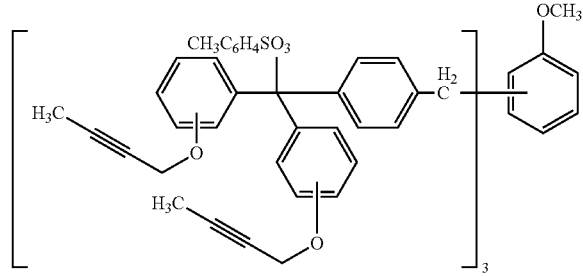
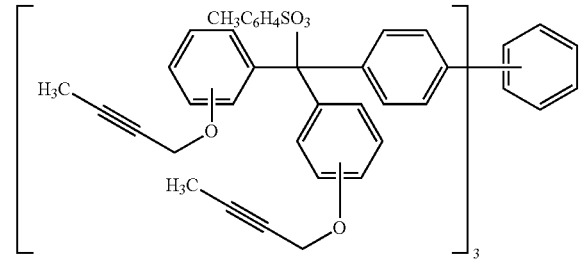
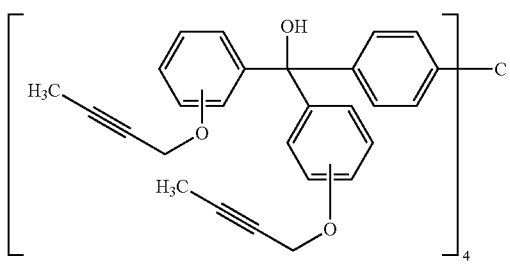

The present invention also provides Compound (4) shown by the following general formula (1-4) and Compound (5) shown by the following general formula (1-5) as useful intermediates to synthesize the Compound (2).

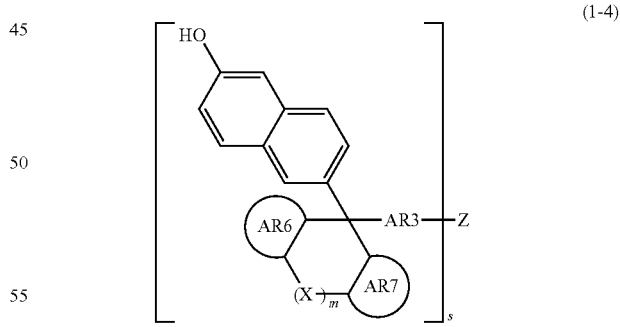

(1-4)

wherein AR3 represents a benzene ring, a naphthalene ring, a thiophene ring, a pyridine ring, or a diazine ring optionally having a substituent; AR6 and AR7 each represent a benzene ring, a naphthalene ring, a thiophene ring, or a pyridine ring optionally having a substituent; "m" is 0 or 1; when m=0, AR6 and AR7 do not form a bridged structure, when m=1, AR6 and AR7 form a bridged structure through X; X represents a single bond or any of groups shown by the following formulae (1-2-1);

(1-2-1)

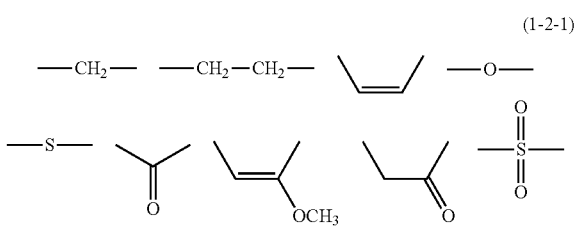

when AR6 and AR7 are bonded through a single bond, at least one of AR6 and AR7 is not a benzene ring; "s" is 2 to 4; when s=2, Z represents a single bond, a divalent atom, or a divalent organic group, and when s=3 or 4, Z represents a trivalent or quadrivalent atom or organic group.

(1-5)

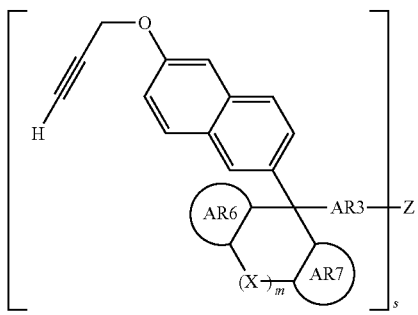

wherein AR3 represents a benzene ring, a naphthalene ring, a thiophene ring, a pyridine ring, or a diazine ring optionally having a substituent; AR6 and AR7 each represent a benzene ring, a naphthalene ring, a thiophene ring, or a pyridine ring optionally having a substituent; "m" is 0 or 1; when m=0, AR6 and AR7 do not form a bridged structure, when m=1, AR6 and AR7 form a bridged structure through X; X represents a single bond or any of groups shown by the following formulae (1-2-1); when AR6 and AR7 are bonded through a single bond, at least one of AR6 and AR7 is not a benzene ring; "s" is 2 to 4; when s=2, Z represents a single bond, a divalent atom, or a divalent organic group; and when s=3 or 4, Z represents a trivalent or quadrivalent atom or organic group.

(1-2-1)

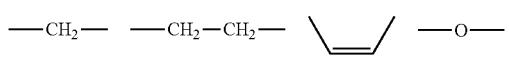

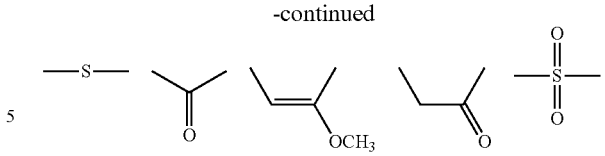

Specific examples of the Compound (4) can contain a structure in which the methylpropargyloxy group of the Compound (2) is changed to a hydroxyl group (provided that when AR4 and AR5 in the general formula (1-2) are bonded through a single bond, at least one of AR4 and AR5 is not a benzene ring), but are not limited thereto. These compounds are useful intermediates for synthesizing the Compound (2) as will be described later. It is also possible to use these compounds themselves for a composition for forming an organic film.

Specific examples of the Compound (5) can contain a structure in which the methylpropargyloxy group of the Compound (2) is changed to a propargyloxy group (provided that when AR4 and AR5 in the general formula (1-2) are bonded through a single bond, at least one of AR4 and AR5 is not a benzene ring), but are not limited thereto. These compounds are useful intermediates for synthesizing the Compound (2) as will be described later. It is also possible to use these compounds themselves for a composition for forming an organic film.

[Production Method of Compound]

The following shows an example of a production method of the inventive compound (2), that is, the compound shown by the general formula (1-2). The production method of the compound (2) is, however, not limited thereto.

The first pathway involves addition reaction of the following ketone compound (i) and the organometallic reagent (ii) to give compound (iii), followed by reaction of the compound (iii) and naphthol to give compound (iv), particularly Compound (4) shown by the general formula (1-4) as an intermediate. Additionally, this intermediate (iv) is subjected to reaction with 3-halogenated propyne (halogenated propargyl) to give compound (v), particularly a compound shown by the general formula (1-5) as the subsequent intermediate, which is methylated to give a compound shown by the following general formula (1-2). It is also possible to obtain a compound shown by the following general formula (1-2) by the reaction of the compound (iv) as an intermediate, particularly a compound shown by the general formula (1-4) and 1-halogenated 2-butyne (halogenated methylpropargyl).

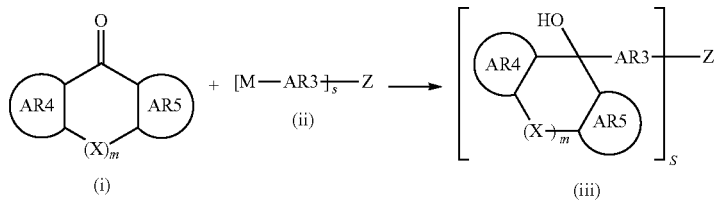

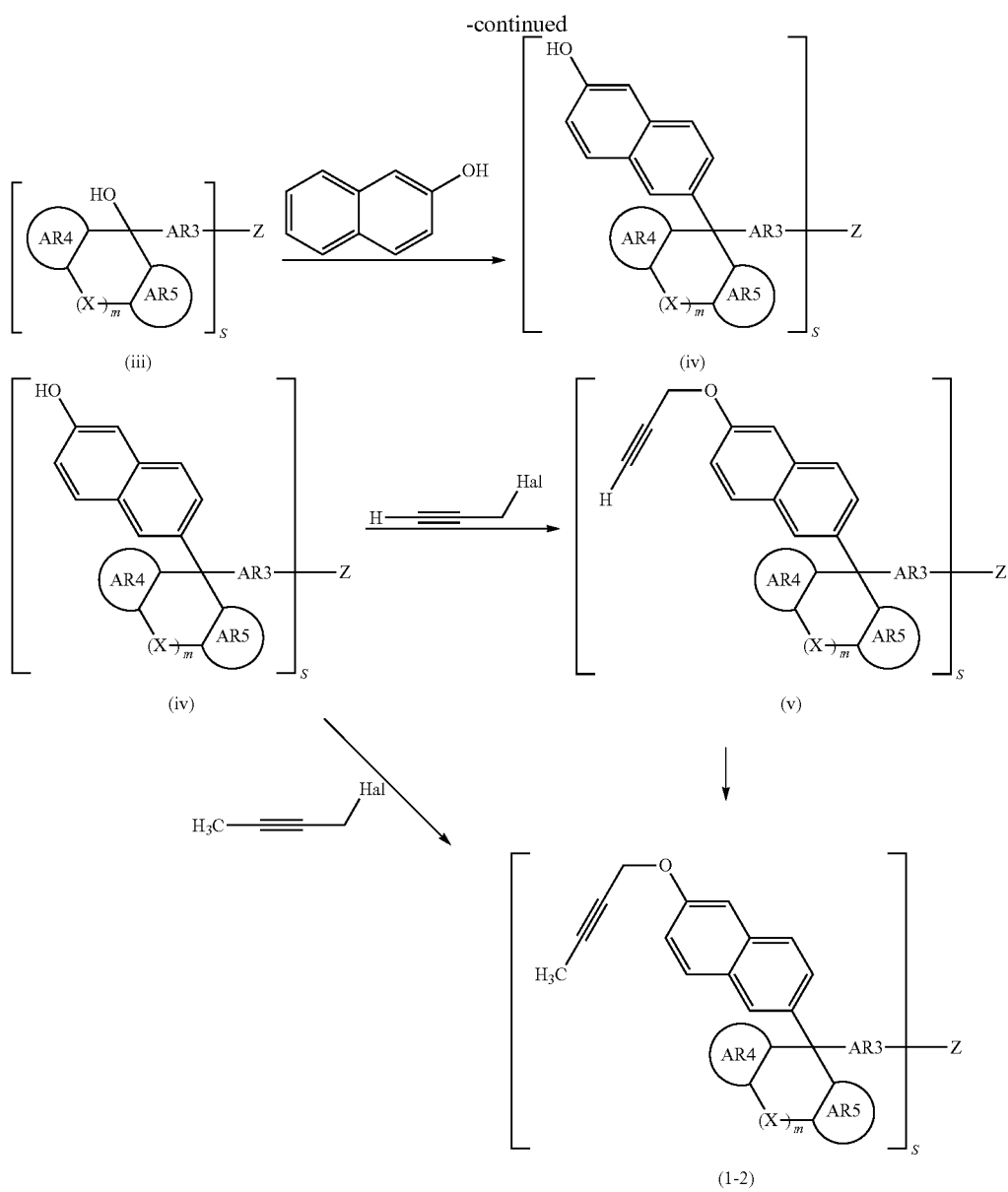

In these formulae, AR3, AR4, AR5, "m", X, "s", and Z have the same meanings as defined above; M represents Li or Mg-Hal, and Hal represents a halogen atom.

In this case, it is preferable to use the organometallic reagent (ii) in an amount of 0.2/s to 40/s mol, particularly 0.5/s to 2/s mol relative to 1 mol of the ketone compound (i) of the above formula.

As the organometallic reagent (ii), Grignard reagents, organolithium reagents, organozinc reagents, and organotitanium reagents are exemplified, and Grignard reagents and organolithium reagents are particularly preferred. The Grignard reagent and the organolithium reagent may be prepared by direct metallation of a corresponding halide and metal magnesium or metal lithium, or may be formed by a metal-halogen exchange reaction with an aliphatic organometallic compound such as an isopropyl magnesium halide, methyl lithium, and butyl lithium. Also, the organozinc reagent or the organotitanium reagent can be prepared from a corresponding Grignard reagent or organolithium reagent by the reaction with a zinc halide, a titanium(IV) halide, or a titanium(IV) alkoxide.

In the preparation of these organometallic reagent (ii) and/or in the reaction between these organometallic reagent and the ketone compound (i), a metal salt compound may be co-presented. As the metal salt compound, a cyanide, a halide, and a perhalogenic acid salt are exemplified, and particularly lithium salts such as lithium chloride, lithium bromide, lithium iodide, and lithium perchlorate, and copper salts such as copper(I) cyanide, copper(II) cyanide, copper (I) chloride, copper(II) chloride, and dilithium tetrachlorocuprate are preferably exemplified. These metal salts are capable of increasing the solubility of the organometallic reagent to facilitate the preparation thereof and controlling the nucleophilicity or Lewis acidity of the reagent when the metal salt compound is added in an amount of 0.01 to 5.0 equivalents, preferably 0.2 to 2.0 equivalents based on an amount of the organometallic reagent, for example.

The solvent to be used for preparing the organometallic reagent (ii) and in the reaction with the ketone compound (i) may be exemplified ethers such as diethyl ether, dibutyl ether, tetrahydrofuran, 1,4-dioxane, cyclopentyl methyl ether, and t-butyl methyl ether; hydrocarbons such as benzene, toluene, xylene, mesitylene, hexane, heptane, octane and isooctane; an aprotic polar solvent such as N,N,N',N'-tetramethylethylenediamine, hexamethylphosphoric triamide, and N,N-dimethylformamide, which can be used singly or by mixture. The reaction temperature may vary depending on a kind of the ketone compound (i) and the organometallic reagent (ii) as well as the reaction conditions, but is preferably −70 to 150° C. The temperature can be selected in many ways such as −70 to 10° C. in case of using an organolithium reagent as the compound (ii) and from room temperature to the boiling point of the solvent (under reflux) in case of using a Grignard reagent as (ii). The reaction is desirably completed by tracing the reaction using chromatography to determine the reaction time, but may be performed for 30 minutes to 48 hours normally.

The dehydration condensation reaction of the compound (iii) and naphthol is usually performed by using acid or base as a catalyst in the absence of a solvent or in a solvent at room temperature or under the conditions of cooling or heating in accordance with needs. Illustrative examples of the solvent to be used include alcohols such as methanol, ethanol, isopropyl alcohol, butanol, ethylene glycol, propylene glycol, diethylene glycol, and glycerol; ethers such as ethylene glycol monomethyl ether, propylene glycol monomethyl ether, diethyl ether, dibutyl ether, diethylene glycol diethyl ether, diethylene glycol dimethyl ether, tetrahydrofuran, and 1,4-dioxane; chlorinated solvent such as methylene chloride, chloroform, dichloroethane, and trichloroethylene; hydrocarbons such as hexane, heptane, benzene, toluene, xylene, and cumene; nitriles such as acetonitrile; ketones such as acetone, ethyl methyl ketone, and isobutyl methyl ketone; esters such as ethyl acetate, n-butyl acetate, and propylene glycol methyl ether acetate; and an aprotic polar solvent such as dimethylsulfoxide, N,N-dimethylformamide, and hexamethyl-phosphoric triamide, which can be used singly or in admixture of two or more kinds. Illustrative examples of the acid catalyst used therein include inorganic acids such as hydrochloric acid, hydrobromic acid, sulfuric acid, nitric acid, phosphoric acid, and heteropoly acid; organic acids such as oxalic acid, trifluoroacetic acid, methanesulfonic acid, benzenesulfonic acid, p-toluenesulfonic acid, and trifluoromethanesulfonic acid; and Lewis acids such as aluminum trichloride, aluminum ethoxide, aluminum isopropoxide, boron trifluoride, boron trichloride, boron tribromide, tin tetrachloride, tin tetrabromide, dibutyltin dichloride, dibutyltin dimethoxide, dibutyltin oxide, titanium tetrachloride, titanium tetrabromide, titanium(IV) methoxide, titanium(IV) ethoxide, titanium(IV) isopropoxide, and titanium(IV) oxide. Illustrative examples of the base catalyst used therein include inorganic bases such as sodium hydroxide, potassium hydroxide, barium hydroxide, sodium carbonate, sodium hydrogen carbonate, potassium carbonate, lithium hydride, sodium hydride, potassium hydride, and calcium hydride; alkyl metals such as methyl lithium, n-butyl lithium, methylmagnesium chloride, and ethylmagnesium bromide; alkoxides such as sodium methoxide, sodium ethoxide, and potassium t-butoxide; and organic bases such as triethylamine, diisopropylethylamine, N,N-dimethylaniline, pyridine, and 4-dimethylaminopyridine. The reaction temperature is preferably from −50° C. to the boiling point of the solvent, more preferably room temperature to 100° C.

As the reaction between the compound (iv) (particularly, the compound shown by the general formula (1-4)) and 3-halogenated propyne (halogenated propargyl) or 1-halogeneted 2-butyne (halogenated methylpropargyl), substitution reaction using base and coupling reaction using a transition metal catalyst can be illustrated. Illustrative examples of the base used for the substitution reaction include inorganic base compounds such as sodium hydrogen carbonate, sodium carbonate, potassium carbonate, calcium carbonate, cesium carbonate, sodium hydroxide, potassium hydroxide, sodium hydride, potassium phosphate; alkoxides such as sodium methoxide, sodium ethoxide, and potassium t-butoxide; organic amine compounds such as triethylamine, pyridine, and N-methylmorpholine; Grignard reagents, organolithium reagents, and metals such as Li and Na, which can be used singly or in admixture of two or more kinds. In case of using a transition metal catalyst, illustrative examples of usable catalyst include copper catalysts such as copper powder, copper chloride, copper bromide, copper iodide, copper acetate, copper hydroxide, and copper nitrate; tris(dibenzylideneacetone)dipalladium, tetrakis(triphenylphosphine)palladium, which can also be combined with the base described above.

Illustrative examples of the reaction method include a method in which the compound (iv) (particularly, the compound shown by the general formula (1-4)), halide, and base are charged at once; a method in which the compound (iv) and halide are dispersed or dissolved, followed by collective addition of the base or dropwise addition of the base diluted with solvent; and a method in which the base is dispersed or dissolved, followed by collective addition of the compound (iv) and the halide or dropwise addition thereof diluted with solvent. A preferable method is, however, a method that involves reaction between the compound (iv) and the base to form an anion, followed by charging the halide.

The solvent used for this step is not particularly limited so long as the solvent is inactive in the above reaction, and illustrative examples thereof include ethers such as diethyl ether, tetrahydrofuran, and dioxane; aromatic solvents such as benzene, toluene, and xylene; aprotic polar solvents such as acetonitrile, dimethylsulfoxide, N,N-dimethylformamide, and N-methylpyrrolidone; and water, which can be used singly or in admixture of two or more kinds. The reaction temperature is preferably about −50° C. to the boiling point of the solvent, more preferably room temperature to 100° C. The reaction is desirably completed by tracing the reaction using chromatography to determine the reaction time, but may be performed for 30 minutes to 48 hours normally.

After a completion of the reaction, the reactant can be diluted with organic solvent and be recycled by subsequent separation and washing with water in order to eliminate the unreacted raw materials, the acid catalyst, etc. remained in the system.

The organic solvent used for the separation and washing is not particularly limited so long as it is capable of dissolving the compound and is separated to form two layers when it is mixed with water, and illustrative examples thereof include hydrocarbons such as hexane, heptane, benzene, toluene, and xylene; esters such as ethyl acetate, n-butyl acetate, and propylene glycol methyl ether acetate; ketones such as methyl ethyl ketone, methyl amyl ketone, cyclohexanone, and methyl isobutyl ketone; ethers such as diethyl ether, diisopropyl ether, methyl tert-butyl ether, and cyclopentyl methyl ether; chlorinated solvents such as methylene chloride, chloroform, dichloroethane, and trichloroethylene; and mixtures thereof.

In the separation and washing, the reactant may be washed with aqueous basic solution in order to eliminate the unreacted raw materials or the acidic components in the system. Specific examples of the base contained in the aqueous basic solution include hydroxides of alkaline metals, carbonates of alkaline metals, hydroxides of alkaline earth metals, carbonates of alkaline earth metals, ammonia, and organic ammonium salts.

Additionally, in the separation and washing, the reactant may be washed with aqueous acidic solution in order to eliminate the unreacted raw materials, metal impurities, or the basic components in the system. Specific examples of the acid contained in the aqueous acid solution include inorganic acids such as hydrochloric acid, hydrobromic acid, sulfuric acid, nitric acid, phosphoric acid, and heteropoly acid; and organic acids such as oxalic acid, trifluoroacetic acid, methanesulfonic acid, benzenesulfonic acid, p-toluenesulfonic acid, and trifluoromethanesulfonic acid.

In the separation and washing with an aqueous basic solution or an aqueous acidic solution, it is possible to perform either one of them or the both of them. The separation and washing is preferably performed in the order of an aqueous basic solution and an aqueous acidic solution in view of eliminating metal impurities.

The separation and washing with an aqueous basic solution and/or an aqueous acidic solution may be followed by washing with neutral water. The washing may be performed in one time, but preferably about one to five times. As the neutral water, deionized water or ultrapure water may be used. One or more times of this washing sufficiently eliminate the basic components and acidic components, and is preferable thereby. This washing provides enough cleaning effect by performing for ten times, and is preferably performed about one to five times.

Additionally, the reaction product after separation and washing can be subjected to concentration and drying by evaporating the solvent under reduced pressure or atmospheric pressure or precipitation to be collected as powder. It is also possible to leave the reactant in a solution state with appropriate concentration in order to improve the usability in preparing a composition for forming an organic film. The concentration at this time is preferably 0.1 to 50% by mass, more preferably 0.5 to 30% by mass. In such a concentration, the viscosity hardly increases, and the usability is not deteriorated. Additionally, such a concentration is economical since excess amount of the solvent is needless.

The solvent used for this process is not particularly limited so long as it is capable of dissolving the polymer, and illustrative examples thereof include ketones such as cyclohexanone and methyl 2-amyl ketone; alcohols such as 3-methoxybutanol, 3-methyl-3-methoxybutanol, 1-methoxy-2-propanol, and 1-ethoxy-2-propanol; ethers such as propylene glycol monomethyl ether, ethylene glycol monomethyl ether, propylene glycol monoethyl ether, ethylene glycol monoethyl ether, propylene glycol dimethyl ether, diethylene glycol dimethyl ether; and esters such as propylene glycol monomethyl ether acetate, propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, propylene glycol mono-tert-butyl ether acetate, which can be used singly or in admixture of two or more kinds.

As the reaction to obtain the compound shown by the general formula (1-2) from the compound (v) (particularly, the compound shown by the general formula (1-5)), substitution reaction with methyl iodide or dimethyl sulfate by using base is exemplified. Illustrative examples of the base used for the substitution reaction include inorganic bases such as sodium hydrogen carbonate, sodium carbonate, potassium carbonate, calcium carbonate, cesium carbonate, sodium hydroxide, potassium hydroxide, sodium hydride, and potassium phosphate; alkoxides such as sodium methoxide, sodium ethoxide, and potassium t-butoxide; an organic amine compounds such as triethylamine, pyridine, and N-methylmorpholine; Grignard reagents, organolithium reagents, and metals such as Li and Na, which can be used singly or in admixture of two or more kinds. Illustrative examples of the solvent used in this step include ethers such as diethyl ether, dibutyl ether, tetrahydrofuran, 1,4-dioxane, cyclopentyl methyl ether, t-butyl methyl ether; hydrocarbons such as benzene, toluene, xylene, mesitylene, hexane, heptane, octane, and isooctane; aprotic polar solvents such as N,N,N',N'-tetramethylethylenediamine, hexamethylphosphoric triamide, and N,N-dimethylformamide, which can be used singly or in admixture of two or more kinds. The reaction temperature may vary depending on a kind of the compound shown by the general formula (1-5) and base as well as the reaction conditions, but is preferably −70 to 150° C. The temperature can be selected in many ways such as −70 to 10° C. in case of using an organolithium reagent as the base and from room temperature to the boiling point of the solvent (under reflux) in case of using a Grignard reagent as the base.

The following describes a design of the inventive compound shown by the general formula (1-2).

The inventive compound shown by the general formula (1-2) has a triple bond(s), which makes the compound curable under non-oxygen conditions, and has a plurality of aromatic rings that are disposed efficiently, which realizes higher heat resistance. Accordingly, this compound is suitable for an organic under layer film for lithography, which is demanded for curing and film forming in an inert gas without forming byproducts. Additionally, the inventive compound having a methylpropargyl group(s) tends to occur thermal flow in heating of film forming since the thermal fluidity of the material is improved and the compound starts heat curing at higher temperature compared to compounds having a propargyl group(s), which has the same triple bond. This feature contributes to improve the characteristics of gap filling and planarization of a pattern formed on a substrate.

As described above, the inventive compound is capable of curing even in an inert gas, and provides a composition for forming an organic film that has heat resistance at a temperature of 400° C. or more and improved gap filling/planarizing characteristics.

It is to be noted that in the present invention, the planarizing characteristics means a property to make the surface of a substrate planar. With the composition that contains a compound shown by the general formula (1-1) of the present invention, it is possible to decrease a step of 100 nm in a substrate 1 to 30 nm or less by applying a composition 3' for forming an organic film onto the substrate 1, followed by heating to form an organic film 3 as shown in FIG. 1, for example. Incidentally, the stepped profile shown in FIG. 1 represents a typical example of the stepped profiles in substrates for semiconductor device production, and the stepped profile of a substrate that can be planarized by the composition that contains a compound shown by the general formula (1-1) of the present invention is not limited thereto.

<Composition for Forming Organic Film>

The present invention also provides a composition for forming an organic film that contains (A) a compound shown by the general formula (1-1) of the present invention and (B) an organic solvent. Incidentally, the inventive compound shown by the general formula (1-1) can be used singly or in combination of two or more kinds in the inventive composition for forming an organic film.

The organic solvent (B) that can be used for the inventive composition for forming an organic film is not particularly limited so long as it dissolves the base polymer (the compound), the acid generator, the crosslinking agent, and other additives described above. Specifically, it is possible to use solvents having a boiling point less than 180° C. such as solvents described in paragraphs [0091]-[0092] of Japanese Patent Laid-Open Publication No. 2007-199653. Among these, propylene glycol monomethyl ether acetate, propylene glycol monomethyl ether, 2-heptanone, cyclopentanone, cyclohexanone, and a mixture of two or more kinds of these compositions are preferably used.

The composition like this can be applied by spin coating to bring excellent dry etching durability as well as heat resistance at a temperature of 400° C. or more and improved gap filling/planarizing characteristics since the composition contains the inventive compound (A) described above.

As the organic solvent of the inventive composition for forming an organic film, it is possible to add a high boiling point solvent having a boiling point of 180° C. or more to the solvent having a boiling point less than 180° C. (it is possible to use admixture of a solvent having a boiling point of 180° C. or more and a solvent having a boiling point less than 180° C.) As the high boiling point solvent, it is possible to use any solvent including hydrocarbons, alcohols, ketones, esters, ethers, chlorinated solvents, etc. so long as it can dissolve the compound for forming an organic film. Specific examples thereof include 1-octanol, 2-ethylhexanol, 1-nonanol, 1-decanol, 1-undecanol, ethylene glycol, 1,2-propylene glycol, 1,3-butylene glycol, 2,4-pentanediol, 2-methyl-2,4-pentanediol, 2,5-hexanediol, 2,4-heptanediol, 2-ethyl-1,3-hexanediol, diethylene glycol, dipropylene glycol, triethylene glycol, tripropylene glycol, glycerin, n-nonyl acetate, ethylene glycol monohexyl ether, ethylene glycol mono-2-ethylhexyl ether, ethylene glycol monophenyl ether, ethylene glycol monobenzyl ether, diethylene glycol monoethyl ether, diethylene glycol monoisopropyl ether, diethylene glycol mono-n-butyl ether, diethylene glycol monoisobutyl ether, diethylene glycol monohexyl ether, diethylene glycol monopheyl ether, diethylene glycol monobenzyl ether, diethylene glycol diethyl ether, diethylene glycol dibutyl ether, diethylene glycol butyl methyl ether, triethylene glycol dimethyl ether, triethylene glycol monomethyl ether, triethylene glycol n-butyl ether, triethylene glycol butyl methyl ether, triethylene glycol diacetate, tetraethylene glycol dimethyl ether, dipropylene glycol monomethyl ether, dipropylene glycol mono-n-propyl ether, dipropylene glycol mono-n-butyl ether, tripropylene glycol dimethyl ether, tripropylene glycol monomethyl ether, tripropylene glycol mono-n-propyl ether, tripropylene glycol mono-n-butyl ether, ethylene glycol monoethyl ether acetate, ethylene glycol monobutyl ether acetate, diethylene glycol monomethyl ether acetate, diethylene glycol monoethyl ether acetate, diethylene glycol monobutyl ether acetate, triacetin, propylene glycol diacetate, dipropylene glycol monomethyl ether acetate, dipropylene glycol methyl n-propyl ether, dipropylene glycol methyl ether acetate, 1,4-butanediol diacetate, 1,3-butylene glycol diacetate, 1,6-hexanediol diacetate, triethylene glycol diacetate, γ-butyrolactone, dihexyl malonate, diethyl succinate, dipropyl succinate, dibutyl succinate, dihexyl succinate, dimethyl adipate, diethyl adipate, and dibutyl adipate, which can be used singly or in admixture of two or more kinds.

The high boiling point solvent may be appropriately selected such that the boiling point is adjusted to a temperature of heat treatment of the composition for forming an organic film. The high boiling point solvent to be added preferably has a boiling point of 180 to 300° C., more preferably 200 to 300° C. With such a boiling point, sufficient thermal fluidity can be obtained since the baking (heat treatment) can be performed without a risk that the solvent evaporates instantly due to the boiling point being too low. With such a boiling point, the film after baking does not contain the remained solvent that has failed to evaporate, and the film properties such as etching durability are not affected.

When the high boiling point solvent is used, the blending amount of the high boiling point solvent is preferably 1 to 30 parts by mass relative to 100 parts by mass of the solvent having a boiling point less than 180° C. Such a blending amount does not cause risks that sufficient thermal fluidity cannot be obtained in baking due to too small blending amount, or the solvent remains in the film to degrade the film properties such as etching durability due to a blending amount that is too large.

The composition for forming an organic film like this, with the inventive compound (A) being additionally provided with thermal fluidity by adding a high boiling point solvent, becomes a composition for forming an organic film having improved gap filling/planarizing characteristics.

Into the inventive composition for forming an organic film, (C) acid generator can be added to promote the curing reaction further. As the acid generator, any type can be added including acid generators that generate acid by heat decomposition and acid generators that generate acid by light irradiation. Specific examples of the acid generator that can be added include materials described in paragraphs [0061]-[0085] of JP 2007-199653A, but is not limited thereto.

The above acid generator can be used singly or in admixture of two or more kinds. When the acid generator is added, the blending amount is preferably 0.05 to 50 parts by mass, more preferably 0.1 to 10 parts by mass relative to 100 parts by mass of the compound (A).

Into the inventive composition for forming an organic film, (D) a surfactant can be added to improve coatability in spin coating. The surfactant can be used those described in paragraphs [0142]-[0147] of JP 2009-269953A.

Into the inventive composition for forming an organic film, a (E) crosslinking agent can be added to improve the curability and to prevent intermixing with the upper layer film. The crosslinking agent is not particularly limited, and it is possible to use wide variety of known crosslinking agents in various types. Illustrative examples thereof include melamine crosslinking agents, glycoluril crosslinking agents, benzoguanamine crosslinking agents, urea crosslinking agents, β-hydroxyalkylamide crosslinking agents, isocyanurate crosslinking agents, aziridine crosslinking agents, oxazoline crosslinking agents, and epoxy crosslinking agents.

Illustrative examples of the melamine crosslinking agent include hexamethoxymethylated melamine, hexabutoxymethylated melamine, alkoxy and/or hydroxy substituents thereof, and partial self-condensates thereof. Illustrative examples of the glycoluril crosslinking agent include tetramethoxymethylated glycoluril, tetrabutoxymethylated glycoluril, alkoxy and/or hydroxy substituents thereof, and partial self-condensates thereof. Illustrative examples of the benzoguanamine crosslinking agent include tetramethoxymethylated benzoguanamine, tetrabutoxymethylated benzoguanamine, alkoxy and/or hydroxy substituents thereof, and partial self-condensates thereof. Illustrative examples of the urea crosslinking agent include dimethoxymethylated dimethoxyethyleneurea, alkoxy and/or hydroxy substituents thereof, and partial self-condensates thereof. Illustrative examples of the β-hydroxyalkylamide crosslinking agent include N,N,N',N'-tetra(2-hydroxyethyl)adipate amide. Illustrative examples of the isocyanurate crosslinking agent include triglycidylisocyanurate and triallylisocyanurate. Illustrative examples of the aziridine crosslinking agent include 4,4'-bis(ethyleneiminocarbonylamino)diphenylmethane and 2,2-bishydroxymethylbutanol-tris[3-(1-aziridinyl)propionate]. Illustrative examples of the oxazoline crosslinking agent include 2,2'-isopropylidene-bis(4-benzyl-2-oxazoline), 2,2'-isopropylidene-bis(4-phenyl-2-oxazoline), 2,2'-methylene-bis(4,5-diphenyl-2-oxazoline), 2,2'-methylene-bis(4-phenyl-2-oxazoline), 2,2'-methylene-bis(4-tert-butyl-2-oxazoline), 2,2'-bis(2-oxazoline), 1,3-phenylene-bis(2-oxazoline), 1,4-phenylene-bis(2-oxazoline), and copolymers of 2-isopropenyloxazoline. Illustrative examples of the epoxy crosslinking agent include diglycidyl ether, ethylene glycol diglycidyl ether, 1,4-butanediol diglycidyl ether, 1,4-cyclohexanedimethanol diglycidyl ether, poly(glycidyl methacrylate), trimethylolethane triglycidyl ether, trimethyloipropane triglycidyl ether, and pentaerythritol tetraglycidyl ether.

Into the inventive composition for forming an organic film, (F) a plasticizer can be added to improve the gap filling/planarizing characteristics. The plasticizer is not particularly limited, and it is possible to use wide variety of known plasticizers of various types. Illustrative examples thereof include low molecular weight compounds such as phthalate esters, adipate esters, phosphate esters, trimellitate esters, and citrate esters; polymers such as polyethers, polyesters, and polyacetal polymers described in JP 2013-253227A.

As an additive to bring the inventive composition for forming an organic film to have further gap filling/planarizing characteristics that is same as in the case of plasticizer, the following examples are preferably used: a liquid state additive having a polyethylene glycol or polypropylene glycol structure, or heat decomposable polymer having a weight loss ratio between 30° C. and 250° C. of 40% by mass or more and a weight average molecular weight of 300 to 200,000. This heat decomposable polymer preferably contains a repeating unit having an acetal structure shown by the following general formula (DP1) or (DP1a).

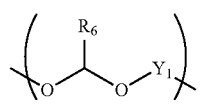
(DP1)

In the formula, $R_6$ represents a hydrogen atom or a saturated or unsaturated monovalent organic group having 1 to 30 carbon atoms which may be substituted; and $Y_1$ represents a saturated or unsaturated divalent organic group having 2 to 30 carbon atoms.

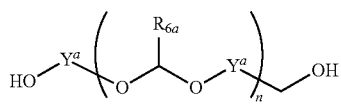
(DP1a)

In the formula, $R_{6a}$ represents an alkyl group having 1 to 4 carbon atoms; $Y^a$ represents a saturated or unsaturated divalent hydrocarbon group having 4 to 10 carbon atoms, which may have an ether bond; and "n" represents an average repeating unit number and is 3 to 500.

As described above, the inventive composition for forming an organic film forms an organic film that has excellent dry etching durability as well as heat resistance at a temperature of 400° C. or more and improved gap filling/planarizing characteristics. Accordingly, it is very useful for an organic under layer film material used for multilayer resist processes such as a two-layer resist process, a three-layer resist process using a silicon-containing resist middle layer film or a silicon-containing inorganic hard mask, and a four-layer resist process using a silicon-containing resist middle layer film or a silicon-containing inorganic hard mask and an organic bottom antireflective coating. The inventive composition for forming an organic film has excellent gap filling/planarizing characteristics without forming byproducts even in film forming in an inert gas, and is favorably used as a planarization material in a production step of a semiconductor device other than the multilayer resist processes.

<Method for forming Organic Film>

The heating step of film forming for forming an organic film can employ one-stage baking, two-stage baking, or multi-stage baking with three or more stages, but one-stage baking or two-stage baking is economical and preferable. The film forming by one-stage baking is preferably performed at a temperature of 100° C. or more and 600° C. or less for 5 to 3600 seconds, particularly at a temperature of 150° C. or more and 500° C. or less for 10 to 7200 seconds. The heat treatment under these conditions makes it possible to promote the planarization by thermal fluidity, and the crosslinking reaction. Onto this obtained film, a coating-type silicon middle layer film or a CVD hard mask is optionally formed in multilayer resist processes. When the coating-type silicon middle layer film is applied, the organic under layer film is preferably formed at a temperature higher than the temperature to form the silicon middle layer film. The silicon middle layer film is usually formed at a temperature of 100° C. or more and 400° C. or less, preferably 150° C. or more and 350° C. or less. When the organic under layer film is formed at a temperature higher than this temperature, it is possible to prevent the organic under layer film from being dissolved by a composition for forming the silicon middle layer film to form an organic film without intermixing. Additionally, it is possible to eliminate the risk that the organic under layer film causes heat decomposition to form byproducts during forming the silicon middle layer film.

When the CVD hard mask is applied, the organic under layer film is preferably formed at a temperature higher than the temperature to form the CVD hard mask. As the temperature to form the CVD hard mask, a temperature of 150° C. or more and 500° C. or less can be exemplified.

On the other hand, in film forming by two-stage baking, when the first-stage baking is performed in air atmosphere, this baking is performed under the conditions that the upper limit of the treatment temperature in air atmosphere is set to 300° C. or less, preferably 250° C. or less and in a range of 10 to 600 seconds if the substrate can cause corrosion due to oxygen. The second-stage in an inert gas is preferably performed by setting the baking temperature to a temperature higher than the baking temperature in the first-stage and 600° C. or less, particularly 500° C. or less for 10 to 7200 seconds.

The inventive composition for forming an organic film can be applied to a method for forming an organic film that functions as an organic under layer film used for a production process of a semiconductor device in which a substrate to be processed is subjected to heat treatment in an atmosphere with the oxygen concentration of 1% or less to form a cured film in order to prevent corrosion of the substrate to be processed.

In this method for forming an organic film, in the first step, the inventive composition for forming an organic film described above is spin coated onto a substrate to be processed. After the spin coating, in two-stage baking, first baking is performed in air atmosphere at a temperature of 300° C. or less, and then second-stage baking is performed in an atmosphere with the oxygen concentration of 1% or less. In case of one stage baking, the first air baking in two-stage baking can be skipped. Incidentally, illustrative examples of the atmosphere in baking include inert gases such as nitrogen, argon, and helium. The inventive material is capable of forming a sufficiently cured organic film without forming sublimated products even when it is heated in such an inert gas atmosphere.

The method for forming an organic film can be used for a substrate to be processed that has a structure or step with the height of 30 nm or more. As described above, the inventive composition for forming an organic film excels in gap filling/planarizing characteristics, thereby being capable of forming a planar cured film even when the substrate to be processed has a structure or a step (unevenness) with the height of 30 nm or more. That is, the inventive method for forming an organic film is particularly useful for forming a planar organic film onto such a substrate to be processed.

The thickness of an organic film to be formed is appropriately selected, but is preferably set to 30 to 20,000 nm, particularly 50 to 15,000 nm.

The above method for forming an organic film is applicable to both cases of using the inventive composition for forming an organic film that becomes an under layer film used in a multilayer resist process and for forming a planarization film.

The inventive composition is usable for forming an organic film that is capable of planarizing the surface of a patterned substrate used in a production process of a semiconductor device, and is applicable to a method for forming an organic film in which the inventive composition for forming an organic film is spin coated onto a substrate to be processed, the substrate coated with the composition for forming an organic film is subjected to heat treatment in air atmosphere at a temperature of 50° C. or more and 250° C. or less for 10 to 600 seconds, and subsequently subjected to heat treatment in an inert gas at a temperature of 250° C. or more for 10 to 7200 seconds to form a cured film.

In this method for forming an organic film, in the first step, the inventive composition for forming an organic film described above is spin coated onto a substrate to be processed. The use of a spin coating method allows to securely obtain good gap filling characteristics. After spin coating, baking (heat treatment) is performed in order to promote the planarization by thermal flow followed by crosslinking of the resulting film. It is to be noted that this baking allows the solvent in the composition to evaporate, and the crosslinked film is resistant to intermixing even when a resist upper layer film or a silicon-containing resist middle layer film is formed thereon.

<Patterning Process>
[Three-Layer Resist Process Using Silicon-Containing Resist Middle Layer Film]

The patterning process can be performed such that an organic film is formed on a substrate to be processed by using the inventive composition for forming an organic film, a silicon-containing film is formed on the organic film by using a film-forming material, a resist upper layer film is formed on the silicon-containing film by using a photoresist composition, a circuit pattern is formed on the resist upper layer film, the pattern is transferred to the silicon-containing film by etching using the patterned upper layer film, the pattern is transferred to the organic film by etching using the patterned silicon-containing film as a mask, and the pattern is transferred to the substrate to be processed by etching using the patterned organic film as a mask.

As the substrate to be processed, it is preferable to use a semiconductor device substrate or the semiconductor device substrate having any of a film selected from a metal film, a metal carbide film, a metal oxide film, a metal nitride film, a metal oxycabide film, and a metal oxynitride film formed thereon. Although it is not particularly limited, specific examples thereof include substrates of Si, α-Si, p-Si, $SiO_2$, SiN, SiON, W, TiN, and Al, for example, and these substrate having the above metal thin film formed thereon as a layer to be processed.

As the layer to be processed, various Low-k films and their stopper films can be used, including Si, $SiO_2$, SiON, SiN, p-Si, α-Si, W, W—Si, Al, Cu, and Al—Si, which can be formed to a thickness of 50 to 10,000 nm usually, and particularly 100 to 5,000 nm. It is to be noted that when a layer to be processed is formed, the substrate and the layer to be processed are made from different materials.

Incidentally, the metal to form the layer to be processed is preferably silicon, titanium, tungsten, hafnium, zirconium, chromium, germanium, copper, silver, gold, aluminum, indium, gallium, arsenic, palladium, iron, tantalum, iridium, cobalt, manganese, molybdenum, or alloy thereof.

As the substrate to be processed, a substrate to be processed that has a structure or a step with the height of 30 nm or more is preferably used.

When the substrate to be processed is subjected to forming of an organic film by using the inventive composition for forming an organic film, the above method for forming an organic film may be applied.

Subsequently, onto the organic film, a resist middle layer film (silicon-containing resist middle layer film) is formed by using a silicon-containing resist middle layer film material. This middle layer film material is preferably based on polysiloxane. The silicon-containing resist middle layer film can possess an antireflective effect. Particularly for exposure at 193 nm, k value becomes higher to increase the reflection of a substrate when the composition for forming an organic layer is a highly aromatic-containing material with high etching selectivity from a substrate. However, the reflection can be decreased to 0.5% or lower if the silicon-containing resist middle layer has appropriate absorption, k value. Since the silicon-containing resist middle layer film has an antireflective effect, it is preferable to use polysiloxane capable of crosslinking by acid or heat with a pendant structure or polysiloxane structure having a light absorbing group containing anthracene for exposure to light of 248 nm or 157 nm, and a phenyl group or a silicon-silicon bond for exposure to light of 193 nm.

Then, onto the silicon-containing resist middle layer film, a resist upper layer film is formed by a photoresist composition. The resist upper layer film material may be either positive tone or negative tone, and photoresist compositions in common use can be used. The resist upper layer film material is preferably subjected to spin coating, followed by pre-baking at a temperature of 60 to 180° C. for 10 to 300 seconds. Subsequently, this is subjected to exposure, post-exposure baking (PEB), and development in accordance with a conventional method to give a resist upper layer film pattern. Incidentally, the film thickness of the resist upper layer film is not particularly limited, but is preferably 30 to 500 nm, particularly 50 to 400 nm.

Subsequently, on the resist upper layer film, a circuit pattern (resist upper layer film pattern) is formed. In forming the circuit pattern, the circuit pattern is preferably formed by lithography using a light having a wavelength of 10 nm or more and 300 nm or less, direct writing with an electron beam, nanoimprinting, or combination thereof.

The light for exposure can be a high-energy beam having a wavelength of 300 nm or less, and specific examples thereof include deep ultraviolet rays, KrF excimer laser (248 nm), ArF excimer laser (193 nm), $F_2$ laser (157 nm), $Kr_2$ laser (146 nm), $Ar_2$ laser (126 nm), soft X-rays (EUV) of 3 to 20 nm, electron beams (EB), ion beams, and X-rays.

In forming the circuit pattern, the circuit pattern is preferably developed by aqueous alkaline development or organic solvent development.

Then, the pattern is transferred to the silicon-containing resist middle layer film by etching using the resist upper layer film having the formed circuit pattern as a mask. The etching of the silicon-containing resist middle layer film, which is performed by using the resist upper layer film pattern as a mask, is preferably performed by using a fluorocarbon base gas. In this way, a silicon-containing resist middle layer film pattern is formed.

Next, the pattern is transferred to the organic film by etching using the silicon-containing resist middle layer film having the transferred pattern as a mask. The etching of the organic film using the silicon-containing resist middle layer film pattern as a mask is preferably performed by using an etching gas mainly composed of oxygen gas or hydrogen gas since silicon-containing resist middle layer films have higher etching durability against oxygen gas or hydrogen gas compared to organic materials. In this way, the organic film pattern is successfully formed.

Subsequently, the pattern is transferred to the substrate to be processed by etching using the organic film having the transferred pattern as a mask. The subsequent etching of a substrate to be processed (layer to be processed) can be performed by a common method such as etching with fluorocarbon base gas when the substrate to be processed is a low dielectric constant insulation film of $SiO_2$, SiN, or silica, and etching with chlorine-base or bromine-base gas when the substrate to be processed is p-Si, Al, or W. When the substrate is processed by etching with fluorocarbon base gas, the silicon-containing resist middle layer pattern is delaminated at the time of substrate processing. On the other hand, when the substrate is processed by etching with chlorine-base or bromine-base gas, the substrate processing has to be followed by dry etching delamination with fluorocarbon base gas separately performed in order to delaminate the silicon-containing resist middle layer pattern.

The organic film obtained by using the inventive composition for forming an organic film is excellent in etching durability in the etching of a substrate to be processed as described above.

[Four-Layer Resist Process Using Silicon-Containing Resist Middle Layer Film and Organic Bottom Antireflective Coating]

The patterning process can also be performed such that an organic film is formed on a substrate to be processed by using the inventive composition for forming an organic film, a silicon-containing resist middle layer film is formed on the organic film by using a resist middle layer film material that contains a silicon atom, an organic bottom antireflective coating is formed on the silicon-containing resist middle layer film, a resist upper layer film is formed on the organic bottom antireflective coating by using a resist upper layer film material composed of a photoresist composition, a circuit pattern is formed on the resist upper layer film, the pattern is transferred to the organic bottom antireflective coating and the silicon-containing resist middle layer film by dry etching using the patterned resist upper layer film, the pattern is transferred to the organic film by etching using the patterned silicon-containing resist middle layer film, and the pattern is transferred to the substrate to be processed by etching using the patterned organic film.

Incidentally, this method can be performed in the same way as in the three layer resist process by using the silicon-containing resist middle layer film except that the organic bottom antireflective coating (BARC) is formed between the silicon-containing resist middle layer film and the resist upper layer film.

The organic bottom antireflective coating can be formed by spin coating using a conventional organic bottom antireflective coating material.

[Three-Layer Resist Process Using Inorganic Hard Mask]

As the patterning process by the three layer resist process using the composition for forming an organic film of the present invention, the patterning process can also be performed such that an organic film is formed on a substrate to be processed by using the inventive composition for forming an organic film, an inorganic hard mask selected from a silicon oxide film, a silicon nitride film, a silicon oxynitride film, titanium oxide film, and titanium nitride film is formed on the organic film, a resist upper layer film is formed on the inorganic hard mask by using a resist upper layer film material composed of a photoresist composition, a circuit pattern is formed on the resist upper layer film, the pattern is transferred to the inorganic hard mask by etching using the patterned resist upper layer film, the pattern is transferred to the organic film by etching using the patterned inorganic hard mask, and the pattern is transferred to the substrate to be processed by etching using the patterned organic film.

Incidentally, this method can be performed in the same way as in the three layer resist process by using the silicon-containing resist middle layer film except that an inorganic hard mask is formed on the organic film instead of the silicon-containing resist middle layer film.

The inorganic hard mask selected from a silicon oxide film, a silicon nitride film, and a silicon oxynitride film (SiON film) can be formed by a CVD method or an ALD method. The method for forming a silicon nitride film is described in, for example, JP 2002-334869A and WO2004/066377. The inorganic hard mask preferably has a film thickness of 5 to 200 nm, more preferably 10 to 100 nm. As the inorganic hard mask, the SiON film, which causes marked effect as an antireflective film, is most preferably used. The temperature of a substrate reaches to 300 to 500° C. when an SiON film is formed. Accordingly, the under layer film have to be durable at a temperature of 300 to 500° C. The organic film formed by using the inventive composition for forming an organic film has higher heat resistance and is durable at a temperature of 300 to 500° C., thereby making it possible to combine an inorganic hard mask formed by a CVD method or an ALD method and an organic film formed by a spin coating method.

[Four-Layer Resist Process Using Inorganic Hard Mask and Organic Bottom Antireflective Coating]

As the patterning process by the four layer resist process using the composition for forming an organic film of the present invention, the patterning process can also be performed such that an organic film is formed on a substrate to be processed by using the inventive composition for forming an organic film, an inorganic hard mask selected from a silicon oxide film, a silicon nitride film, and a silicon oxynitride film is formed on the organic film, an organic bottom antireflective coating is formed on the inorganic hard mask, a resist upper layer film is formed on the organic bottom antireflective coating by using a resist upper layer film material composed of a photoresist composition, a circuit pattern is formed on the resist upper layer film, the pattern is transferred to the organic bottom antireflective coating and the inorganic hard mask by etching using the resist upper layer film having the formed circuit pattern as a mask, the pattern is transferred to the organic film by etching using the inorganic hard mask having the transferred pattern as a mask, and the pattern is transferred to the substrate to be processed by etching using the organic film having the transferred pattern as a mask.

Incidentally, this method can be performed in the same way as in the three layer resist process by using the inorganic hard mask except that the bottom anti-reflective coating (BARC) is formed between the inorganic hard mask and the resist upper layer film.

In particular, when a SiON film is used as the inorganic hard mask, it is possible to decrease reflection by virtue of the two-layer antireflective films of the SiON film and the BARC film, even by a liquid immersion exposure at a higher NA exceeding 1.0. Another merit of the formation of the BARC resides in obtainment of an effect to reduce footing of a resist upper layer film pattern compared on the SiON film.

Figure 2:
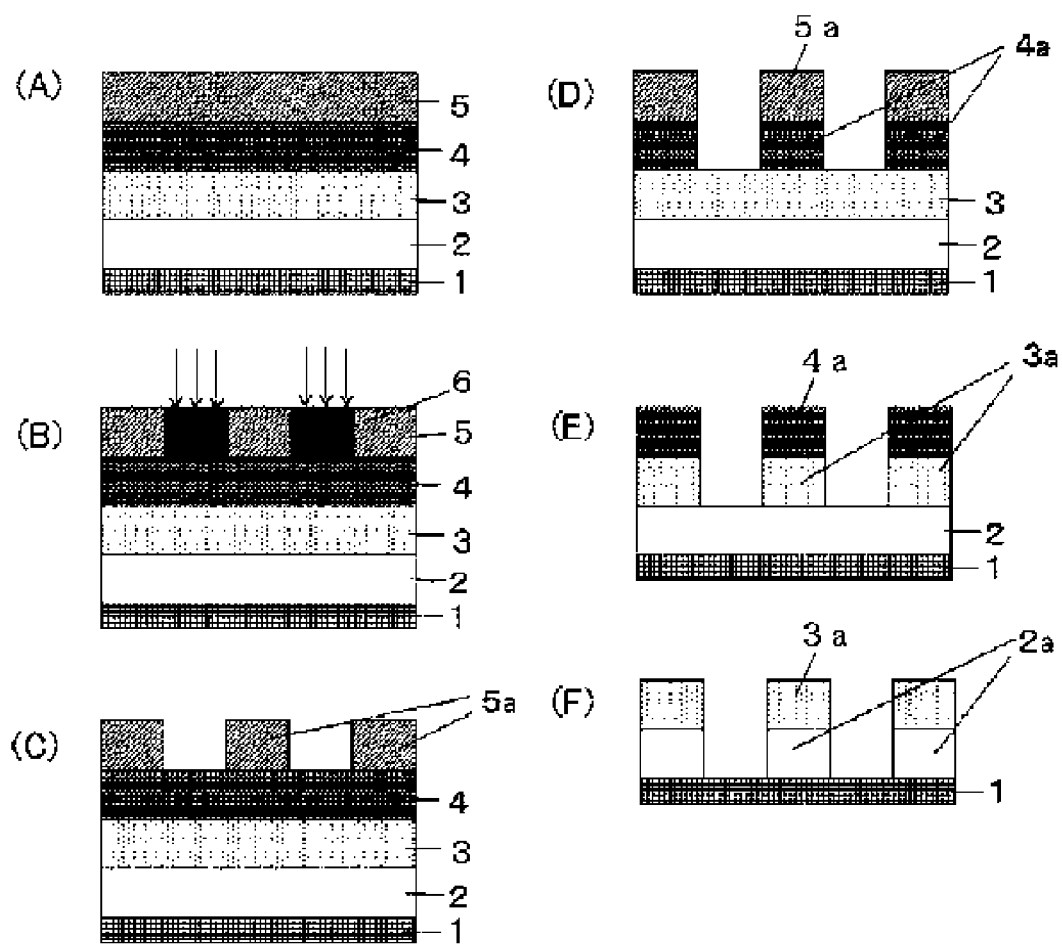
FIG. 2 is an explanatory diagram of an example of a patterning process by the three-layer resist process.

An example of the patterning process by a three layer resist process is shown in FIGS. 2(A) to (F). In the three layer resist process, as shown in FIG. 2(A), on layer to be processed 2 formed on a substrate 1, an organic film 3 is formed by using the inventive composition for forming an organic film, followed by forming a silicon-containing resist middle layer film 4, and forming a resist upper layer film 5 thereon. Then, as shown in FIG. 2(B), the exposure area 6 of the resist upper layer film 5 is exposed, followed by post-exposure baking (PEB). Subsequently, as shown in FIG. 2(C), a resist upper layer film pattern 5a is formed by development. Next, as shown in FIG. 2(D), a silicon-containing resist middle layer film pattern 4a is formed by dry etching processing of the silicon-containing resist middle layer film 4 with fluorocarbon base gas using the resist upper layer film pattern 5a as a mask. Then, as shown in FIG. 2(E), subsequent to removing the resist upper layer film pattern 5a, an organic film pattern 3a is formed by oxygen plasma etching of the organic film 3 using the silicon-containing resist middle layer film pattern 4a as a mask. Additionally, as shown in FIG. 2(F), subsequent to removing the silicon-containing resist middle layer film pattern 4a, a pattern 2a is formed by etching processing of the layer to be processed 2 using the organic film pattern 3a as a mask.

In case of forming an inorganic hard mask, the process may be performed by changing the silicon-containing resist middle layer film 4 to the inorganic hard mask; and in case of forming a BARC, the process may be performed by forming the BARC between the silicon-containing resist middle layer film 4 and the resist upper layer film 5. It is possible to continuously perform etching of the BARC prior to the etching of the silicon-containing resist middle layer film 4. It is also possible to perform etching of the BARC only, followed by etching of the silicon-containing resist middle layer film 4 after changing the etching apparatus, for example.

As described above, the inventive patterning process makes it possible to form a fine pattern on a substrate to be processed with high accuracy by a multilayer resist process.

EXAMPLES

Hereinafter, the present invention will be specifically described by showing Synthesis Examples, Comparative Synthesis Examples, Examples, and Comparative Examples, but the present invention is not limited thereto. Incidentally, as the weight average molecular weight and dispersity, weight average molecular weight (Mw) and number average molecular weight (Mn) are determined in terms of polystyrene by gel permeation chromatography (GPC) using tetrahydrofuran as an eluent, and then the dispersity (Mw/Mn) was determined.

Synthesis Examples: Synthesis of Highly Heat-Resistant Organic Compounds

[Synthesis Example 1] Synthesis of Compound (A1)

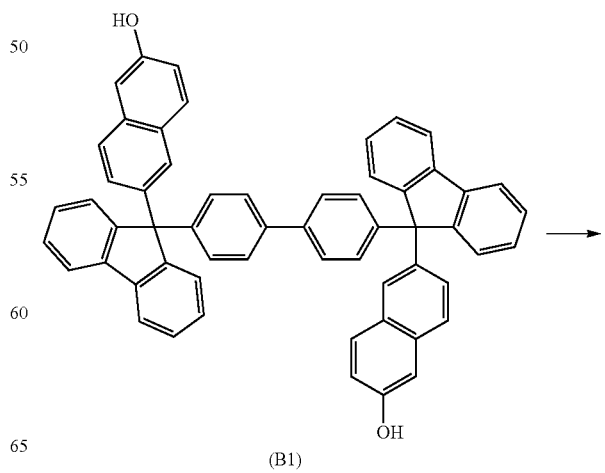

(B1)

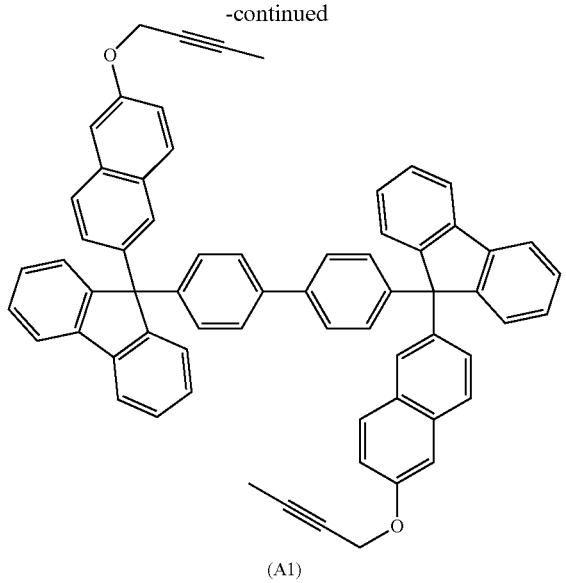

(A1)

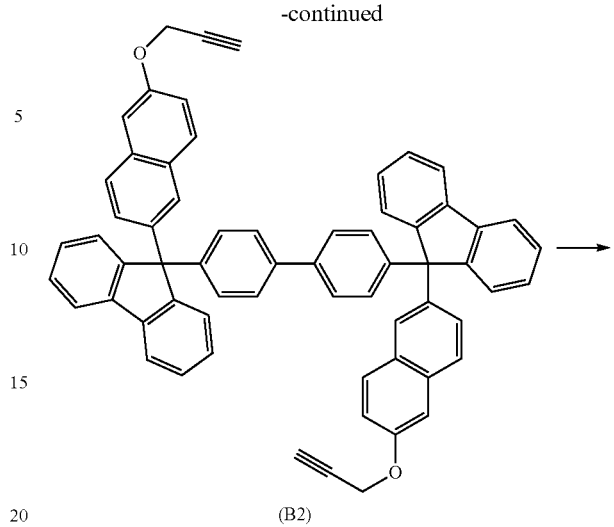

(B2)

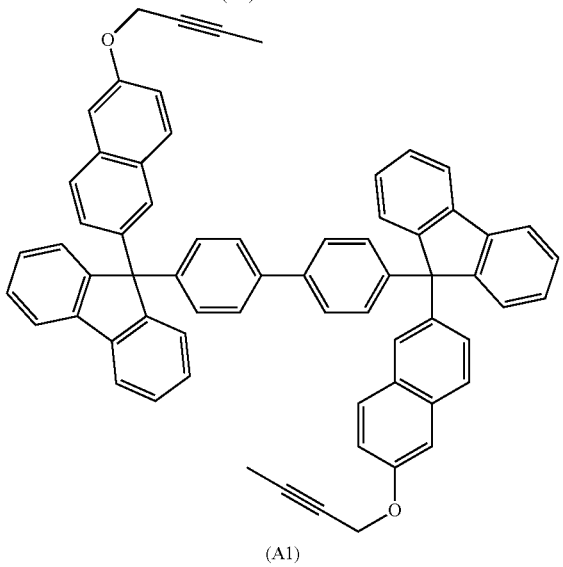

(A1)

A mixture of 7.7 g of Diol (B1), 3.0 g of potassium carbonate, and 40 g of N,N-dimethylformamide was heated to 55° C. To the mixture, 2.9 g of 1-bromo-2-butyne was slowly added dropwise, and this was stirred with heating at 55° C. for 20 hours. After cooling to room temperature, 150 g of methyl isobutyl ketone was added thereto. This was washed with water and concentrated in vacuum, and then precipitated with methanol. The yielded solid was filtered off, washed with methanol, and dried in vacuum to give 8.7 g of the object (A1). The following are analytical results of IR and $^1$H NMR for the synthesized Compound (A1).

IR (D-ATR): ν=3057, 3029, 2954, 2916, 2867, 1601, 1494, 1476, 1446, 1217, 1005, and 819 cm$^{-1}$ $^1$H NMR (600 MHz, DMSO-d$_6$) δ (ppm): 7.94 (d, J=7.3 Hz, 4H), 7.71 (d, J=9.2 Hz, 2H), 7.60 (d, J=9.2 Hz, 2H), 7.51-7.45 (m, 10H), 7.41-7.38 (m, 4H), 7.31-7.28 (m, 6H), 7.28-7.15 (m, 6H), 7.08-7.06 (m, 2H), 4.80 (d, J=2.3 Hz, 4H), 1.79 (dd, J=2.3, 2.3 Hz, 6H).

The weight average molecular weight (Mw) and dispersity (Mw/Mn) were determined by CPC, and the following results were obtained.

(A1): Mw=1000, Mw/Mn=1.23

[Synthesis Example 2] Synthesis of Compound (A1)

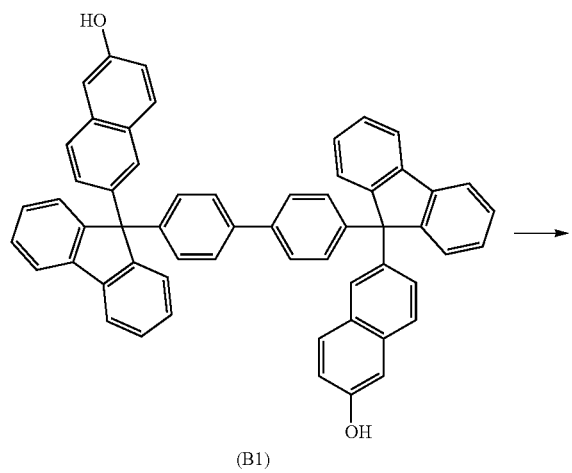

(B1)

A mixture of 7.7 g of Diol (B1), 3.0 g of potassium carbonate, and 40 g of N,N-dimethylformamide was heated to 55° C. To the mixture, 3.3 g of 80% propargyl bromide toluene solution was slowly added dropwise, and this was stirred with heating at 55° C. for 14 hours. After cooling to room temperature, 150 g of toluene was added thereto. This was washed with water and concentrated in vacuum to give 8.4 g of Propargyl derivative (52).

Then, under an N$_2$ atmosphere, to a mixture of 8.4 g of Propargyl derivative (52) and 60 mL of tetrahydrofuran cooled to −30° C., 10 mL of 2.65 M n-butyl lithium hexane solution was added, and this was stirred at −30° C. for 1 hour. To this, 4.4 g of dimethyl sulfate was added. This was allowed to gradually raise the temperature to room temperature, heated to 60° C., and stirred for 6 hours. After cooling to room temperature, dilute hydrochloric acid wad added to stop the reaction, and 100 g of methyl isobutyl ketone was added thereto. This was washed with water and concentrated in vacuum, and then, methanol was added thereto. The yielded solid was filtered off, washed with methanol, and dried in vacuum to give 8.5 g of the object (A1). The following are analytical results of IR and $^1$H NMR for the synthesized Compound (A1).

IR (D-ATR): ν=3058, 3029, 2954, 2917, 2868, 1602, 1494, 1477, 1446, 1218, 1005, and 819 cm$^{-1}$ $^1$H NMR (600 MHz, DMSO-d$_6$) δ (ppm): 7.94 (d, J=7.3 Hz, 4H), 7.71 (d, J=9.2 Hz, 2H), 7.60 (d, J=9.2 Hz, 2H), 7.51-7.45 (m, 10H), 7.41-7.38 (m, 4H), 7.31-7.28 (m, 6H), 7.28-7.15 (m, 6H), 7.08-7.06 (m, 2H), 4.80 (d, J=2.3 Hz, 4H), 1.79 (dd, J=2.3, 2.3 Hz, 6H).

The weight average molecular weight (Mw) and dispersity (Mw/Mn) were determined by GPC, and the following results were obtained.

(A1): Mw=1000, Mw/Mn=1.32

[Synthesis Example 3] Synthesis of Compound (A2)

To a mixture of 8.78 g of 4,4'-dihydroxybenzophenone and 50 mL of acetone, 17 g of potassium carbonate was added, and 7.9 mL of 1-bromo-2-butyne was added dropwise. The reaction mixture was heated and was heated to reflux overnight. After cooling to room temperature, followed by filtration, the filtrate was concentrated in vacuum. Then, mixed solvent of methanol:Chloroform=9:1 was added thereto, and yielded solid was filtered off to give 10.6 g of Intermediate (B3) shown by the following formula. The following are analytical results of $^1$H NMR for the synthesized Intermediate (B3).

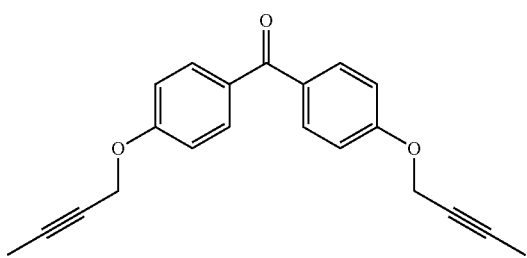
(B3)

$^1$H NMR (400 MHz, CDCl$_3$) δ (ppm): 7.81 (d, Ar—H, 4H), 7.05 (d, Ar—H, 4H), 4.75 (s, CH$_2$, 4H), 1.90 (s, CH$_3$, 6H).

Then, under an N$_2$ atmosphere, to a mixture of 5.44 g of 4,4'-dibromobiphenyl and 50 mL of tetrahydrofuran cooled to −70° C., 23.92 mL of 1.6 M n-butyl lithium hexane solution was added, and this was stirred at −40° C. for 1 hour. To this, 12.18 g of Intermediate (B3) that had been dissolved to 50 mL of tetrahydrofuran was added dropwise. This was allowed to gradually raise the temperature to room temperature, and stirred at room temperature overnight. The reaction was stopped by adding 100 mL of aqueous 14% ammonium chloride solution, and 200 mL of ethyl acetate was added thereto. This was washed with water and concentrated in vacuum. Then, mixed solvent of dichloromethane:pentane=1:3 was added thereto, and this was cooled to 0 to 5° C. The yielded solid was filtered off washed with pentane, and dried in vacuum to give 8.7 g of Compound (A2) shown by the following formula. The following are analytical results of $^1$H NMR for the synthesized Compound (A2).

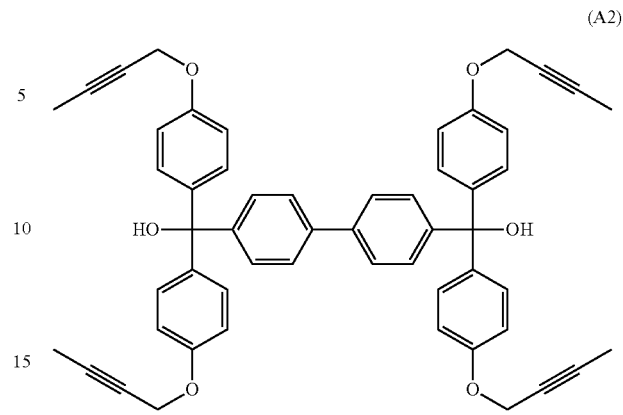
(A2)

$^1$H NMR (400 MHz, CDCl$_3$) δ (ppm): 7.55 (d, Ar—H, 4H), 7.35 (d, Ar—H, 4H), 7.23 (d, Ar—H, 8H), 6.93 (d, Ar—H, 8H), 4.66 (s, CH$_2$, 8H), 1.88 (s, CH$_3$, 12H).

[Synthesis Example 4] Synthesis of Compound (A3)

Under N$_2$ atmosphere, 25 g of ethyl 2-chloronicotinate, 21.04 g of phenylboronic acid, 3 g of tetrakis(triphenylphosphine)palladium (0), 55.1 g of potassium carbonate, and 250 mL of mixed solvent of tetrahydrofuran:water=1:1 were mixed, and the reaction mixture was heated to reflux overnight. After cooling to room temperature, 200 mL of ethyl acetate was added thereto, the water layer was removed and the remaining organic layer was washed with distilled water (2×100 mL). The obtained organic layer was dried over magnesium sulfate, and was concentrated in vacuum. The obtained oily material was filtered through silica, and was dissolved to 150 mL of methanol. To this solution, 10.8 g of sodium hydroxide was added, and this was stirred at room temperature for 6 hours. The reaction solution was concentrated in vacuum, and the obtained white solid was diluted with water. The pH was adjusted to between 4 and 5 by adding 1 M hydrochloric acid. The yielded white crystal was filtered off to give the following Compound (B4). The obtained water layer was extracted with ethyl acetate (2×100 mL). The organic layers were combined, dried over magnesium sulfate, and then, filtered and concentrated in vacuum to give the remaining Compound (B4). The total of 21.46 g of Compound (B4) was obtained. The following are analytical results of $^1$H NMR for the synthesized Compound (B4).

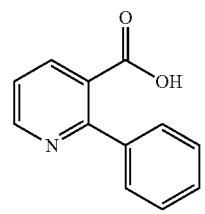
(B4)

$^1$H NMR (400 MHz, DMSO-d$_6$) δ (ppm): 13.31 (bs, COO—H, 1H), 8.76 (d, Ar—H, 1H), 8.11 (d, Ar—H, 1H), 7.58 (m, Ar—H, 3H), 7.46 (m, Ar—H, 3H).

Then, under N$_2$ atmosphere, into a three-necked flask equipped with a thermometer, polyphosphoric acid heated to 80° C. (in an amount of 25% relative to Compound (B4)) was introduced. Subsequently, 9.96 g of Compound (B4) was added dropwise, and this was stirred vigorously at 210° C. for 3 hours. After cooling the reaction solution to between 60 and 70° C., aqueous 1 M sodium hydroxide solution was added such that pH=10 to quench the reaction. The yielded solid was filtered off, washed with distilled water, and dried in vacuum to give 9.05 g of Compound (B5). The following are analytical results of $^1$H NMR for the synthesized Compound (B5).

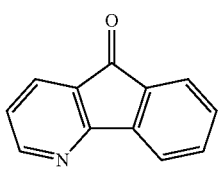
(B5)

$^1$H NMR (400 MHz, CDCl$_3$) δ (ppm): 8.64 (d, Ar—H, 1H), 7.92 (m, Ar—H, 2H), 7.76 (d, Ar—H, 1H), 7.64 (t, Ar—H, 1H), 7.47 (t, Ar—H, 1H), 7.25 (m, Ar—H, 1H).

Then, under an N$_2$ atmosphere, to a mixture of 2.38 g of 4,4'-dibromobiphenyl and 50 mL of tetrahydrofuran cooled to −70° C., 10.45 mL of 1.6 M n-butyl lithium hexane solution was added, and this was stirred at −40° C. for 1 hour. To this, 500 mg of Compound (55) was added. The temperature was gradually allowed to warm to room temperature, and stirred overnight. The reaction was stopped by adding 50 mL of aqueous 14% ammonium chloride solution. The water layer was removed, and the organic layer was concentrated in vacuum. Then, methylene chloride was added thereto, and this was cooled to 0 to 5° C. and stirred vigorously. The yielded solid was filtered off, washed with methanol, and dried in vacuum to give 2.2 g of Compound (86). The following are analytical results of $^1$H NMR and MALDI-TOF MS for the synthesized Compound (86).

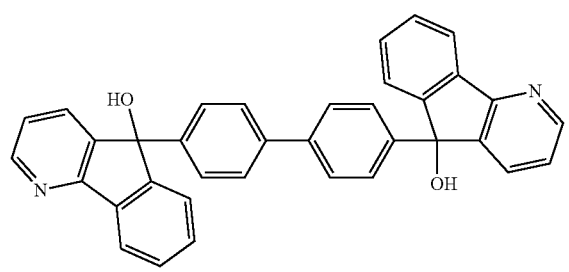
(B6)

$^1$H NMR (400 MHz, DMSO-ds) δ (ppm): 8.53 (d, Ar—H, 2H), 7.87 (d, Ar—H, 2H), 7.65 (d, Ar—H, 2H), 7.51-7.45 (m, —H, 6H), 7.42-7.38 (m, Ar—H, 4H), 7.34 (d, Ar—H, 4H), 7.26-7.23 (m, Ar—H, 2H), 6.60 (bs, OH, 2H).
MALDI-TOF MS m/z (+ve): 498 [M−OH]$^+$.

Subsequently, 500 mg of Compound (B6), 307 mg of 2-naphthol, and 18 mL of acetic acid were mixed. To this suspension, 2 mL of methansulfonic acid was added, and the reaction mixture was placed under an atmosphere of N$_2$, followed by reflux with heating for 16 hours. After cooling to room temperature, saturated aqueous sodium hydrogen carbonate solution (100 mL) was added thereto, and the mixture was subjected to extraction with ethyl acetate (2×50 mL). The organic layers were combined, washed with distilled water (2×50 mL), and dried over magnesium sulfate. This was filtered and concentrated in vacuum. Then, ethanol was added thereto, and this was stirred at 0 to 5° C. for 1 hour. The yielded solid was filtered off, washed with ethanol, and dried in vacuum to give 320 mg of Compound (87). The following are analytical results of $^1$H NMR and MALDI-TOF MS for the synthesized Compound (57).

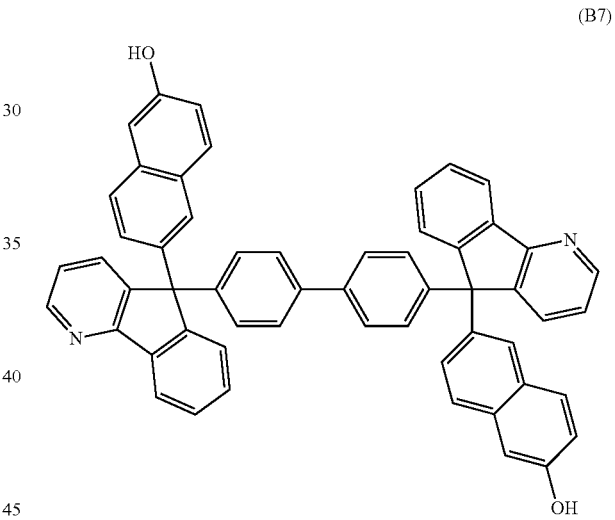
(B7)

$^1$H NMR (400 MHz, DMF-d$_7$) δ (ppm): 9.76 (bs, OH, 2H), 8.60 (s, Ar—H, 2H), 8.02 (d, Ar—H, 2H), 7.80 (m, Ar—H, 2H), 7.69-7.13 (m, Ar—H, 26H), 7.12-6.95 (m, Ar—H, 2H).
MALDI-TOF MS m/z (+ve): 768 [M−H]$^+$.

200 mg of Compound (57), 74 mg of propargyl bromide, 108 mg of potassium carbonate, and 10 mL of N,N-dimethylformamide were mixed. This was heated to 80° C., and stirred with heating for 24 hours. After cooling to room temperature, 60 mL of ethyl acetate was added thereto. This was washed with saturated aqueous sodium chloride solution (2×50 mL) and distilled water (2×50 mL). This was dried over magnesium sulfate, followed by filtration and concentration in vacuum. Then, 200 mL of hexane was added thereto, and this was cooled to 0 to 5° C. and stirred for 1 hour. The yielded solid was filtered off, washed with hexane, and dried in vacuum to give 181 mg of Compound (58). The following are analytical results of $^1$H NMR and MALDI-TOF MS for the synthesized Compound (B8).

(B8)

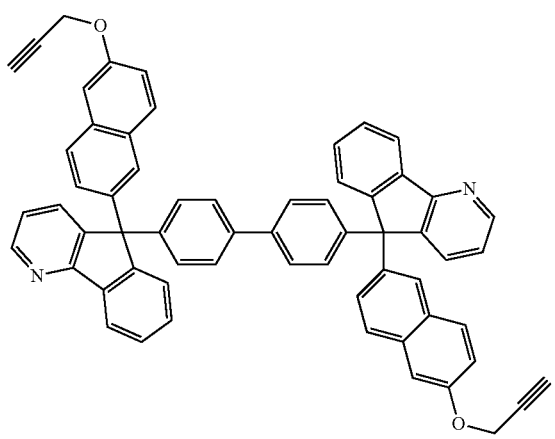

¹H NMR (400 MHz, DMSO-d₆) δ (ppm): 8.60 (s, Ar—H, 2H), 8.04 (d, Ar—H, 2H), 7.94-6.94 (m, Ar—H, 30H), 4.88 (s, CH₂, 4H), 3.58 (s, CH, 2H).
MALDI-TOF MS m/z (+ve): 845 [M–H]⁺.

Under an N₂ atmosphere, to a mixture of 100 mg of Compound (B8) and 10 mL of tetrahydrofuran cooled to −60 to −70° C., 0.162 mL of 1.6 M n-butyl lithium hexane solution was added, and this was stirred at −50 to −40° C. for 1 hour. After the reaction solution was cooled to −60 to −70° C., 0.022 mL of methyl iodide was added. The temperature was gradually allowed to warm to room temperature, and stirred overnight. After cooling, 30 mL of ethyl acetate was added thereto. The organic layer was washed with saturated aqueous sodium chloride solution (2×25 mL) and distilled water (2×25 mL). This was dried over magnesium sulfate, followed by filtration and concentration in vacuum. Then, 100 mL of hexane was added thereto, and this was cooled to 0 to 5° C. and stirred for 1 hour. The yielded solid was filtered off, washed with hexane, and dried in vacuum to give 83 mg of the object (A3). The following are analytical results of ¹H NMR and MALDI-TOF MS for the synthesized Compound (A3).

(A3)

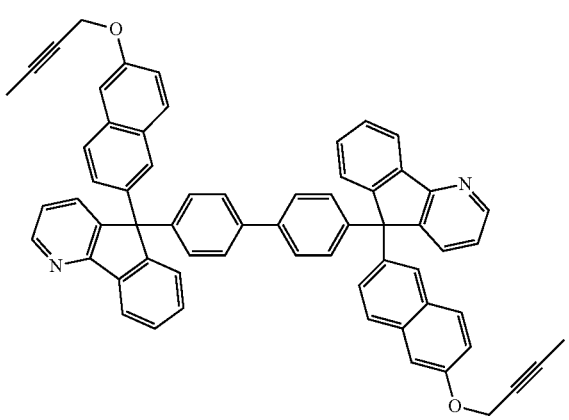

¹H NMR (400 MHz, DMSO-d₆) δ (ppm): 8.62 (s, Ar—H, 2H), 8.04 (d, Ar—H, 2H), 7.94-6.94 (m, Ar—H, 30H), 4.87 (s, CH₂, 4H), 1.77 (s, CH₃, 6H).
MALDI-TOF MS m/z (+ve): 873 [M–H]⁺.

The weight average molecular weight (Mw) and dispersity (Mw/Mn) were determined by GPC, and the following results were obtained.
(A3): Mw=500, Mw/Mn=1.14

Comparative Synthesis Examples: Synthesis of Organic Compounds

[Comparative Synthesis Example 1] Synthesis of Compound (A4)

A mixture of 7.7 g of Diol (B1), 3.0 g of potassium carbonate, and 40 g of N,N-dimethylformamide was heated to 55° C. To the mixture, 3.3 g of 80% propargyl bromide toluene solution was slowly added dropwise, and this was stirred with heating at 55° C. for 14 hours. After cooling to room temperature, 150 g of toluene was added thereto. This was washed with water and concentrated in vacuum to give 8.4 g of Propargyl derivative (A4).

(A4)

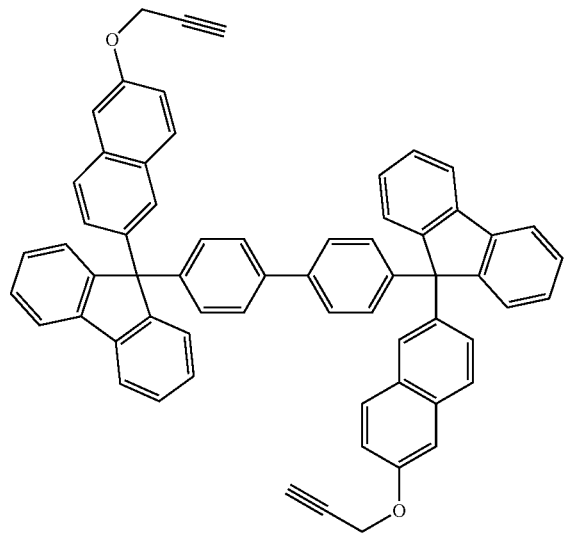

The weight average molecular weight (Mw) and dispersity (Mw/Mn) were determined by GPC, and the following results were obtained.
(A4): Mw=1000, Mw/Mn=1.09

[Comparative Synthesis Example 2] Synthesis of Compound (A5)

Under nitrogen atmosphere, 90.1 g of 9,9-fluorenylidene-bisnaphthol, 10.5 g of 37% aqueous formalin solution, and 270 g of 2-methoxy-1-propanol were mixed to a homogeneous solution at a bulk temperature of 80° C. Then, 18 g of 20% 2-methoxyl-propanol solution of pare-toluenesulfonic acid was slowly added thereto, and this was stirred at a bulk temperature of 110° C. for 8 hours. After cooling to room temperature, 600 g of methyl isobutyl ketone was added. The organic layer was washed with 200 g of pure water for five times, and then, dried in vacuum. To this residue, 400 ml of THF was added, and the polymer was reprecipitated from 2,000 ml of hexane. The precipitated polymer was separated by filtration, and dried in vacuum to give Compound (A5).

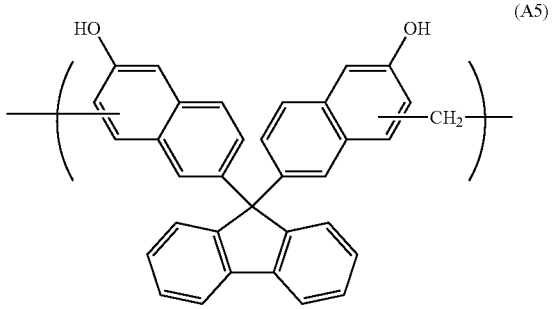

(A5)

The weight average molecular weight (Mw) and dispersity (Mw/Mn) were determined by GPC, and the following results were obtained.

(A5): Mw=3700, Mw/Mn=2.82

[Comparative Synthesis Example 3] Synthesis of Compound (A6)

Under nitrogen atmosphere, into a 5 L four-necked flask in which 26.4 g (1.09 mol) of magnesium had been weighed, the solution of 168 g (0.54 mol) of 4,4'-dibromobiphenyl and 23.0 g (0.54 mol) of lithium chloride that had been dissolved into 1,000 ml of dehydrated THF (tetrahydrofuran) was added in an amount so as to immerse the magnesium. A small amount of dibromoethene was added to start the reaction. Subsequently, the rest of the THF solution was added dropwise over 3 hours while maintaining a stable temperature. After finishing the dropwise addition, 500 ml of THF was added, and reaction mixture was refluxed for 8 hours to prepare the Grignard reagent. After cooling to the bulk temperature of 55° C., 150 g of 9-fluorenone (0.83 mol) that had been dissolved into 400 ml of THF was added dropwise for 2 hours. After the dropwise addition was finished, reaction mixture was refluxed for 5.5 hours. The flask was cooled with ice-water, and the reaction was quenched with 1,000 ml of saturated aqueous ammonium chloride solution and 1,000 ml of pure water. At this stage, a white precipitate was formed. To the reaction solution, 150 ml of methyl isobutyl ketone (MIBK) was added, and the suspension was transferred to a separating funnel. The water layer was removed, and the organic layer was washed with 500 ml of pure water, followed by concentration in vacuum. After recrystallization from diisopropyl ether, the resulting white crystals were filtered off and dried to give 109 g of Biphenyl derivative (B9) in a yield of 51.0%.

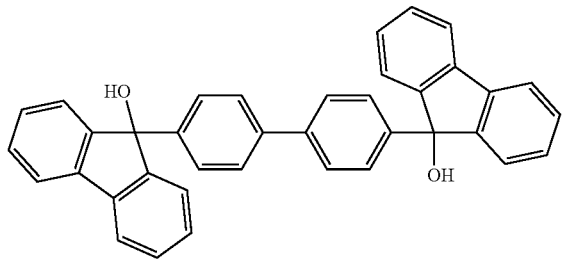

(B9)

Biphenyl derivative (B9):
IR (D-ATR): ν=3539, 3064, 3039, 1605, 1495, 1447, 1164, 1030, 909, 820, 771, 754, and 736 cm$^{-1}$.

$^1$H-NMR (600 MHz in DMSO-d$_6$): δ=6.34 (2H, —OH, s), 7.24 (4H, t), 7.27 (8H, d), 7.36 (4H, t-t), 7.45 (4H, d), and 7.81 (4H, d) ppm.
$^{13}$C-NMR (150 MHz in DMSO-d$_6$): δ=82.44, 120.10, 124.66, 125.66, 126.28, 128.07, 128.51, 138.41, 139.14, 144.19, and 151.23 ppm.

Subsequently, 40.3 g (78.4 mmol) of Biphenyl derivative (B9), 23.73 g (164.6 mmol) of 2-naphthol, and 240 ml of 1,2-dichloroethane was weighed in a 1 L three-necked flask. While this was stirred in an oil bath at 30° C., 7.3 ml of methanesulfonic acid was slowly added dropwise. After the dropwise addition, the temperature of the oil bath was increased to 50° C. to allow the mixture to react for 6 hours. After cooling to room temperature, this was diluted with 500 ml of MIBK. This was transferred to a separating funnel after filtering the insoluble components, and subjected to separation and washing for nine times with ultrapure water. The organic layer was concentrated in vacuum, and the residue was dissolved in 800 ml of added THF, and crystallized from 2,500 ml of hexane. The crystal was filtered off and dried to give 51.6 g of biphenyl derivative Compound (A6) in a yield of 85.8%.

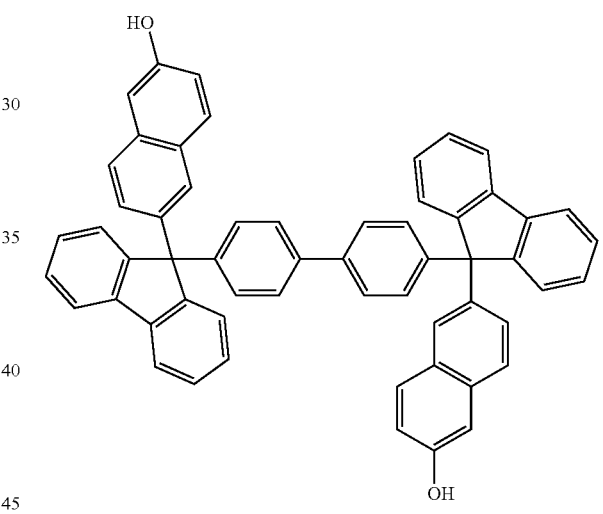

(A-6)

Compound (A6)
IR (KBr): ν=3528, 3389, 3059, 3030, 1633, 1604, 1506, 1493, 1446, 1219, 1181, 750, and 740 cm$^{-1}$.
$^1$H-NMR (600 MHz in DMSO-d$_6$): δ=6.98 (2H, d-d), 7.05 (2H, s-d), 7.17 (4H, d), 7.24 (2H, d-d), 7.29 (4H, t), 7.38 (4H, t), 7.40 (2H, s), 7.45 (4H, d), 7.50 (6H, d), 7.58 (2H, d), 7.93 (4H, d), and 9.72 (2H, —OH, s) ppm.
$^{13}$C-NMR (150 MHz in DMSO-d$_6$): δ=64.59, 108.35, 118.77, 120.58, 125.19, 126.11, 126.36, 126.62, 126.94, 127.16, 127.71, 127.88, 128.20, 129.35, 133.39, 138.14, 139.26, 139.59, 144.82, 150.56, and 155.39 ppm.

Preparation of Composition for Forming Organic Film (UDL-1 to 5, Comparative UDL-1 to 4)

Into a solvent of propylene glycol monomethyl ether acetate (PGMEA) containing 0.1% by mass of FC-4430 (manufactured by 3M Japan Limited), Compounds (A1) to (A6) described above, a crosslinking agent (CR1) and an acid generator (AGI), together with 1,6-diacetoxyhexane (b.p.: 260° C.) (S1) or tripropylene glycol monomethyl ether (b.p.: 242° C.) (S2) as a solvent as additives were dissolved in each ratio shown in Table 1. This was filtrated through 0.1

μm filter made from fluororesin to prepare each Composition for forming an organic film (UDL-1 to 5, Comparative UDL-1 to 4).

TABLE 1

| Composition for forming organic film | Compound (parts by mass) | Additive (1) (parts by mass) | Additive (2) (parts by mass) | Additive (3) (parts by mass) | PGMEA (parts by mass) |
|---|---|---|---|---|---|
| UDL-1 | A1 (5) | — | — | — | 100 |
| UDL-2 | A2 (5) | — | — | — | 100 |
| UDL-3 | A3 (5) | — | — | — | 100 |
| UDL-4 | A1 (5) | — | — | S1 (10) | 90 |
| UDL-5 | A1 (5) | — | — | S2 (10) | 90 |
| Comparative UDL-1 | A4 (5) | — | — | — | 100 |
| Comparative UDL-2 | A5 (5) | — | — | — | 100 |
| Comparative UDL-3 | A6 (5) | — | — | — | 100 |
| Comparative UDL-4 | A6 (5) | CR1 (2) | AG1 (0.5) | — | 100 |

The following are Crosslinking agent (CR1) and the Acid generator (AG1) used herein.

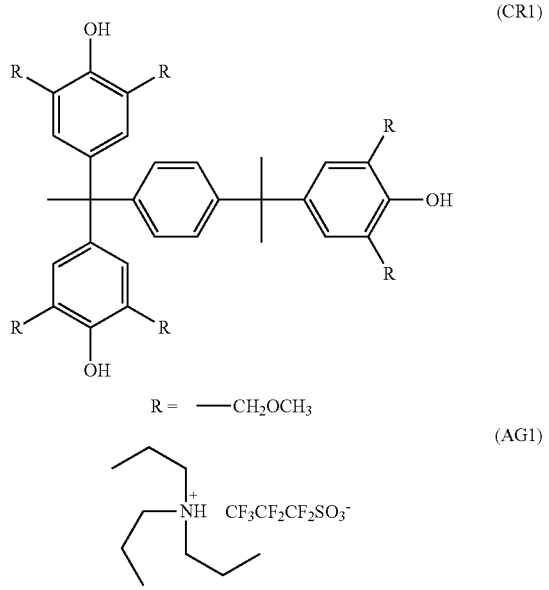

Example 1 Measurement of Solvent Resistance after Baking in Nitrogen Atmosphere (Examples 1-1 to 1-5, Comparative Examples 1-1 to 1-4)

Each Composition for forming an organic film (UDL-1 to 5, Comparative UDL-1 to 4) prepared in the above was applied onto a silicon substrate, and was baked at 400° C. for 60 seconds in a flow of nitrogen in which the oxygen concentration had been controlled to 0.2% or less. Then, the film thickness was measured. PGMEA solvent was dispensed thereonto and allowed to stand for 30 seconds, followed by spin drying and baking at 100° C. for 60 seconds to evaporate the PGMEA. The film thickness was measured, and the difference of film thickness before and after the PGMEA treatment was determined. The results are shown in Table 2.

TABLE 2

| | Composition for forming organic film | Film thickness after forming film: a (Å) | Film thickness after PGMEA treatment: b (Å) | b/a × 100 (%) |
|---|---|---|---|---|
| Example 1-1 | UDL-1 | 1154 | 1154 | 100.0 |
| Example 1-2 | UDL-2 | 1156 | 1155 | 99.9 |
| Example 1-3 | UDL-3 | 1152 | 1150 | 99.8 |
| Example 1-4 | UDL-4 | 1158 | 1157 | 99.9 |
| Example 1-5 | UDL-5 | 1160 | 1158 | 99.8 |
| Comparative Example 1-1 | Comparative UDL-1 | 1148 | 1144 | 99.7 |
| Comparative Example 1-2 | Comparative UDL-2 | 1151 | 528 | 45.9 |
| Comparative Example 1-3 | Comparative UDL-3 | 1151 | 355 | 30.8 |
| Comparative Example 1-4 | Comparative UDL-4 | 1144 | 1142 | 99.8 |

As shown in Table 2, with the inventive composition for forming an organic film (Examples 1-1 to 1-5), each film remaining rate after the PGMEA treatment was 99% or more, showing that the crosslinking reaction occurred in nitrogen atmosphere to attain sufficient solvent resistance. On the other hand, in Comparative Examples 1-2 and 1-3, without adding a crosslinking agent and a thermal acid generator, sufficient solvent resistance was not attained such that the film remaining rate after the PGMEA treatment were less than 50%. The addition of a crosslinking agent and a thermal acid generator was necessary to attain sufficient solvent resistance. These results reveal that the partial structure shown by (A-carbon-carbon triple bond —Y) in the general formula (1-1) generates heat curing reaction in nitrogen atmosphere to attain solvent resistance.

Example 2 Measurement of Solvent Resistance after Baking in the Atmosphere (Examples 2-1 to 2-5, Comparative Examples 2-1 to 2-4)

Each Composition for forming an organic film (UDL-1 to 5, Comparative UDL-1 to 4) prepared in the above was applied onto a silicon substrate, and was baked at 350° C. for 60 seconds in the atmosphere. Then, the film thickness was measured. PGMEA solvent was dispensed thereonto and allowed to stand for 30 seconds, followed by spin drying and baking at 100° C. for 60 seconds to evaporate the PGMEA. The film thickness was measured, and the difference of film thickness before and after the PGMEA treatment was determined. The results are shown in Table 3.

TABLE 3

| | Composition for forming organic film | Film thickness after forming film: a (Å) | Film thickness after PGMEA treatment: b (Å) | b/a × 100 (%) |
|---|---|---|---|---|
| Example 2-1 | UDL-1 | 1154 | 1154 | 100.0 |
| Example 2-2 | UDL-2 | 1142 | 1141 | 99.9 |
| Example 2-3 | UDL-3 | 1142 | 1141 | 99.9 |
| Example 2-4 | UDL-4 | 1157 | 1154 | 99.7 |
| Example 2-5 | UDL-5 | 1157 | 1155 | 99.8 |
| Comparative Example 2-1 | Comparative UDL-1 | 1143 | 1141 | 99.8 |
| Comparative Example 2-2 | Comparative UDL-2 | 1158 | 1156 | 99.8 |
| Comparative Example 2-3 | Comparative UDL-3 | 1147 | 295 | 25.7 |
| Comparative Example 2-4 | Comparative UDL-4 | 1143 | 1135 | 99.3 |

As shown in Table 3, with the inventive composition for forming an organic film (Examples 2-1 to 2-5), each film remaining rate was 99% or more, showing that the crosslinking reaction also occurred in the atmosphere to attain sufficient solvent resistance. On the other hand, in Comparative Example 2-3, without adding a crosslinking agent and a thermal acid generator, sufficient solvent resistance was not attained such that the film remaining rates were less than 50%. The addition of a crosslinking agent and an thermal acid generator was necessary to attain sufficient solvent resistance. These results show that the partial structure shown by (A-carbon-carbon triple bond —Y) in the general formula (1-1) also generates heat curing reaction in the atmosphere to attain solvent resistance.

Example 3 Evaluation of Gap Filling Characteristics (Examples 3-1 to 3-5, Comparative Examples 3-1 to 3-4)

Figure 3:
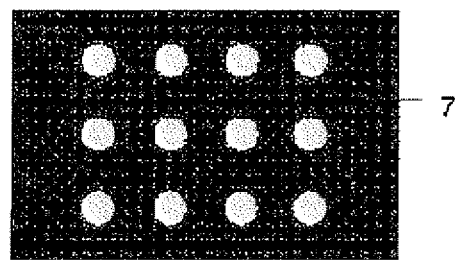
FIG. 3 is an explanatory diagram of a method for evaluating the filing characteristics in Examples.
Figure 3:
Figure 3:
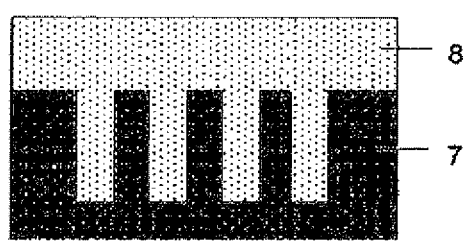

Each Composition for forming an organic film (UDL-1 to 5, Comparative UDL-1 to 4) prepared in the above was applied onto an SiO$_2$ wafer substrate having a dense hole pattern as shown in FIG. 3 (hole diameter: 0.16 μm, hole depth: 0.50 μm, the distance between the centers of two adjacent holes: 0.32 μm). This was baked at 400° C. for 60 seconds by using a hot plate in a flow of nitrogen in which the oxygen concentration had been controlled to 0.2% or less to form an organic film 8. The substrate used in this Example was a basis substrate 7 (SiO$_2$ wafer substrate) having a dense hole pattern shown in FIGS. 3(G) (bird's-eye view) and (H) (cross sectional view). Each cross sectional profile of the obtained wafer substrates were observed through scanning electron microscope (SEM) to determine whether the holes were filled with the organic film without having void therein. The results are shown in Table 4. In case of using a composition for forming an organic film with inferior gap filling characteristics, voids are supposed to form in the holes in this evaluation. In case of using a composition for forming an organic film with good gap filling characteristics, the holes will be filled with the organic film without forming a void in this evaluation as shown in FIG. 3(I). The results are shown in Table 4.

TABLE 4

|  | Composition for forming organic film | Void |
| --- | --- | --- |
| Example 3-1 | UDL-1 | Non |
| Example 3-2 | UDL-2 | Non |
| Example 3-3 | UDL-3 | Non |
| Example 3-4 | UDL-4 | Non |
| Example 3-5 | UDL-5 | Non |
| Comparative Example 3-1 | Comparative UDL-1 | Non |
| Comparative Example 3-2 | Comparative UDL-2 | Exist |
| Comparative Example 3-3 | Comparative UDL-3 | Exist |
| Comparative Example 3-4 | Comparative UDL-4 | Exist |

As shown in Table 4, it was found that the inventive composition for forming an organic film (Examples 3-1 to 3-5) brought excellent gap filling characteristics such that the hole pattern was successfully filled without forming a void. On the other hand, it was confirmed that the gap filling characteristics were unsatisfactory in Comparative Examples 3-2 to 3-4 to form voids. These results show that the inventive composition for forming an organic film provided fluidity to improve the gap filling characteristics due to the partial structure shown by (A-carbon-carbon triple bond —Y) in the general formula (1-1).

Example 4 Evaluation of Planarizing Characteristics (Examples 4-1 to 4-5, Comparative Examples 4-1 to 4-4)

Figure 4:
FIG. 4 is an explanatory diagram of a method for evaluating the planarizing characteristics in Examples.
Figure 4:
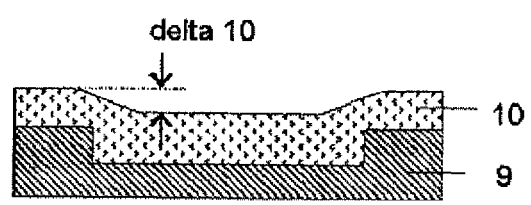

Each Composition for forming an organic film (UDL-1 to 5, Comparative UDL-1 to 4) was applied onto a basis substrate 9 (SiO$_2$ wafer substrate) having a large isolated trench pattern shown in FIG. 4 (FIG. 4(J), trench width: 10 μm, trench depth: 0.10 μm). This was baked at 400° C. for 60 seconds in a flow of nitrogen in which the oxygen concentration had been controlled to 0.2% or less. The step 10 between the trench portion and non-trench portion (delta 10 in FIG. 4(K)) was observed by using NX10 Atomic Force Microscope (AFM) manufactured by Park Systems. The results are shown in Table 5. In this evaluation, smaller step means better planarizing characteristics. Incidentally, this evaluation adopted severe conditions to evaluate planarizing characteristics such that a trench pattern with the depth of 0.10 μm was planarized by using the composition for forming an organic film with the ordinal film thickness of 0.2 μm. The results are shown in Table 5.

TABLE 5

|  | Composition for forming organic film | Step (nm) |
| --- | --- | --- |
| Example 4-1 | UDL-1 | 40 |
| Example 4-2 | UDL-2 | 45 |
| Example 4-3 | UDL-3 | 40 |
| Example 4-4 | UDL-4 | 30 |
| Example 4-5 | UDL-5 | 35 |
| Comparative Example 4-1 | Comparative UDL-1 | 90 |
| Comparative Example 4-2 | Comparative UDL-2 | 90 |
| Comparative Example 4-3 | Comparative UDL-3 | 70 |
| Comparative Example 4-4 | Comparative UDL-4 | 95 |

As shown in Table 5, it was confirmed that the inventive composition for forming an organic film (Examples 4-1 to 4-5) excelled in planarizing characteristics such that each organic film had a smaller step between the trench portion and non-trench portion compared to those of Comparative Examples 4-1 to 4-4. Among the compositions for forming an organic film of Comparative Examples, the one containing a crosslinking agent showed particularly poor planarization characteristics. It was found that superior planarizing characteristics was attained due to the partial structure shown by (A-carbon-carbon triple bond —Y) in the general formula (1-1). In comparison between Examples 4-4 to 4-5, which contained high boiling point solvent, and Example 4-1 without containing the same, it was found that the planarizing characteristics was improved by the addition of high boiling point solvent.

Example 5 Evaluation of Heat Resistance (Examples 5-1 to 5-5, Comparative Examples 5-1 to 5-4)

Each Composition for forming an organic film (UDL-1 to 5, Comparative UDL-1 to 4) described above was applied onto a silicon substrate, and was baked at 180° C. in the atmosphere to form a coated film with a target thickness of 115 nm. The film thickness was measured. The substrate was additionally baked at 400° C. in a flow of nitrogen in which the oxygen concentration had been controlled to 0.2% or less, and the film thickness was measured (Examples 5-1 to 5-5, Comparative Examples 5-1 to 5-4). These results are shown in Table 6.

TABLE 6

| | Composition for forming organic film | Film thickness baked at 180° C.: A (Å) | Film thickness baked at 400° C.: B (Å) | (B/A) × 100 (%) |
|---|---|---|---|---|
| Example 5-1 | UDL-1 | 1150 | 1143 | 99.4 |
| Example 5-2 | UDL-2 | 1143 | 1137 | 99.5 |
| Example 5-3 | UDL-3 | 1157 | 1148 | 99.2 |
| Example 5-4 | UDL-4 | 1157 | 1151 | 99.5 |
| Example 5-5 | UDL-5 | 1150 | 1141 | 99.2 |
| Comparative Example 5-1 | Comparative UDL-1 | 1151 | 1144 | 99.4 |
| Comparative Example 5-2 | Comparative UDL-2 | 1155 | 925 | 80.1 |
| Comparative Example 5-3 | Comparative UDL-3 | 1157 | 582 | 50.3 |
| Comparative Example 5-4 | Comparative UDL-4 | 1150 | 859 | 74.7 |

As shown in Table 6, it was found that each organic film formed from the inventive composition for forming an organic film had high heat resistance such that the decrease of the film thickness was less than 1% even after baking at 400° C. in the inventive composition for forming an organic film (Examples 5-1 to 5-5). On the other hand, in Comparative Examples 5-2 to 5-4, the film thicknesses were decreased largely compared to the inventive composition for forming an organic film. Even in Comparative Example 5-4, cured with an added crosslinking agent, the film thickness was decreased by more than 10%.

Example 6 Patterning Test (Examples 6-1 to 6-5, Comparative Examples 6-1 to 6-4)

Each Composition for forming an organic film (UDL-1 to 5, Comparative UDL-1 to 4) described above was applied onto a silicon wafer substrate having an $SiO_2$ film with the thickness of 300 nm formed thereon. This was baked at 400° C. for 60 seconds in a flow of nitrogen in which the oxygen concentration had been controlled to 0.2% or less to form an organic film (resist under layer film). A CVD-SiON hard mask was formed thereon. Additionally, an organic bottom antireflective coating material (ARC-29A, manufactured by NISSAN CHEMICAL INDUSTRIES, LTD.) was applied and baked at 210° C. for 60 seconds to form an organic bottom antireflective coating with the film thickness of 80 nm. A single layer resist for ArF of a resist upper layer film material was applied thereonto, and baked at 105° C. for 60 seconds to form a photoresist film with the film thickness of 100 nm. A liquid immersion top coat composition (TC-1) was applied on the photoresist film, and baked at 90° C. for 60 seconds to form a top coat with the film thickness of 50 nm.

The resist upper layer film material (single layer resist for ArF) was prepared by dissolving Polymer (RP1), an acid generator (PAG1), and a basic compound (Amine1) in each ratio shown in Table 7 into a solvent containing 0.1% by mass of FC-4430 (manufactured by 3M Japan Limited), followed by filtration through 0.1 μm filter made from fluororesin.

TABLE 7

| | Polymer (parts by mass) | Acid generator (parts by mass) | Basic compound (parts by mass) | Solvent (parts by mass) |
|---|---|---|---|---|
| single layer resist for ArF | PR1 (100) | PAG1 (6.6) | Amine1 (0.8) | PEGMEA (2500) |

The following shows the polymer (RP1), the acid generator (PAG1), and the basic compound (Amine1) used herein.

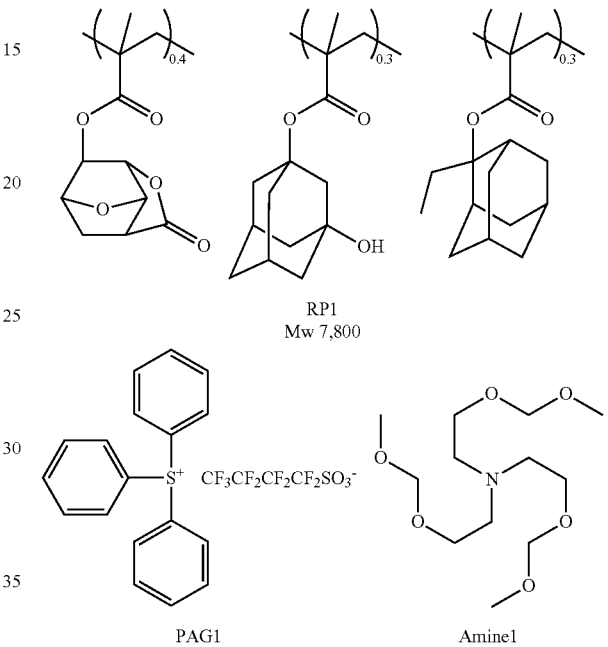

RP1
Mw 7,800

PAG1

Amine1

The liquid immersion top coat composition (TC-1) was prepared by dissolving the top coat polymer (PP1) into an organic solvent in a ratio described in Table 8, followed by filtration through 0.1 μm filter made from fluororesin.

TABLE 8

| | Polymer (parts by mass) | Organic solvent (parts by mass) |
|---|---|---|
| TC-1 | PP1 (100) | diisoamyl ether (2700) 2-methyl-1-butanol (270) |

The following is the polymer (PP1) used herein.

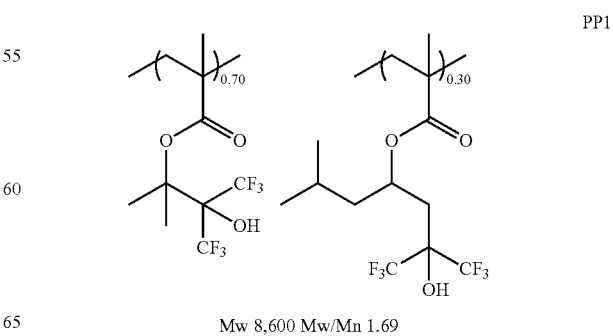

PP1

Mw 8,600 Mw/Mn 1.69

Then, the composition was exposed by using ArF liquid immersion exposure apparatus (NSR-S610C manufactured by Nikon Corporation, NA: 1.30, σ: 0.98/0.65, 35° dipole s polarizing illumination, 6% half-tone phase shift mask), baked at 100° C. for 60 seconds (PEB), and developed with 2.38% by mass aqueous tetramethylammonium hydroxide (TMAH) solution for 30 seconds to obtain 55 nm 1:1 positive-type line-and-space pattern.

Subsequently, etching processing was performed by using an etching apparatus Telius manufactured by Tokyo Electron Limited such that the organic bottom antireflective coating and the CVD-SiON hard mask were subjected to dry etching using the resist pattern as a mask to form a hard mask pattern, the organic film was subjected to etching using the hard mask pattern as a mask to form an organic film pattern, and the $SiO_2$ film was subjected to etching processing by using the obtained organic film pattern as a mask. The etching conditions are as shown below.

Transcription conditions of the resist pattern to the SiON hard mask.

| Chamber pressure | 10.0 Pa |
| --- | --- |
| RF power | 1,500 W |
| $CF_4$ gas flow rate | 75 sccm |
| $O_2$ gas flow rate | 15 sccm |
| Time | 15 sec |

Transcription conditions of the hard mask pattern to the organic film.

| Chamber pressure | 2.0 Pa |
| --- | --- |
| RF power | 500 W |
| Ar gas flow rate | 75 sccm |
| $O_2$ gas flow rate | 45 sccm |
| Time | 120 sec |

Transcription conditions of the organic film pattern to the $SiO_2$ film.

| Chamber pressure | 2.0 Pa |
| --- | --- |
| RF power | 2,200 W |
| $C_5F_{12}$ gas flow rate | 20 sccm |
| $C_2F_6$ gas flow rate | 10 sccm |
| Ar gas flow rate | 300 sccm |
| $O_2$ gas flow rate | 60 sccm |
| Time | 90 sec |

Each pattern cross-section was observed by an electron microscope (S-4700) manufactured by Hitachi, Ltd., and the results are shown in Table 9.

TABLE 9

| | Composition for forming organic film | Pattern profile after substrate transcription etching |
| --- | --- | --- |
| Example 6-1 | UDL-1 | Perpendicular |
| Example 6-2 | UDL-2 | Perpendicular |
| Example 6-3 | UDL-3 | Perpendicular |
| Example 6-4 | UDL-4 | Perpendicular |
| Example 6-5 | UDL-5 | Perpendicular |
| Comparative Example 6-1 | Comparative UDL-1 | Perpendicular |
| Comparative Example 6-2 | Comparative UDL-2 | Pattern collapse |
| Comparative Example 6-3 | Comparative UDL-3 | Pattern collapse |
| Comparative Example 6-4 | Comparative UDL-4 | Perpendicular |

As shown in Table 9, it was confirmed that the inventive composition for forming an organic film was favorably used for fine processing by a multilayer resist process such that each of the resist upper layer film patterns was finally transferred to the substrate favorably in the results of the inventive composition for forming an organic film (Examples 6-1 to 6-5). On the other hand, Comparative Examples 6-2 to 6-3 failed to obtain a good pattern such that pattern collapse was caused in the patterning process since the heat resistance was insufficient and the curing was insufficient in a nitrogen atmosphere as shown in Comparative Examples 1-2 to 1-3. In Comparative Example 6-4, a pattern could be formed, but the heat resistance was insufficient.

Example 7 Patterning Test (Examples 7-1 to 7-5, Comparative Examples 7-1 to 7-4)

By the same method as in Example 6, forming of a laminate, patterning, and dry etching were performed except that each Composition for forming an organic film (UDL-1 to 5, Comparative UDL-1 to 4) was applied onto an $SiO_2$ wafer substrate having a trench pattern shown (trench width: 10 μm, trench depth: 0.10 μm), and was baked at 400° C. for 60 seconds in a flow of nitrogen in which the oxygen concentration had been controlled to 0.2% or less. Each obtained pattern profile was observed. The results are shown in Table 10.

TABLE 10

| | Composition for forming organic film | Pattern profile after substrate transcription etching |
| --- | --- | --- |
| Example 7-1 | UDL-1 | Perpendicular |
| Example 7-2 | UDL-2 | Perpendicular |
| Example 7-3 | UDL-3 | Perpendicular |
| Example 7-4 | UDL-4 | Perpendicular |
| Example 7-5 | UDL-5 | Perpendicular |
| Comparative Example 7-1 | Comparative UDL-1 | Perpendicular |
| Comparative Example 7-2 | Comparative UDL-2 | Pattern collapse |
| Comparative Example 7-3 | Comparative UDL-3 | Pattern collapse |
| Comparative Example 7-4 | Comparative UDL-4 | Pattern collapse |

As shown in Table 10, it was confirmed that the inventive composition for forming an organic film was favorably used for fine processing by a multilayer resist process such that each of the resist upper layer film patterns was favorably transferred to the substrate finally in the results of the inventive composition for forming an organic film (Examples 7-1 to 7-5). On the other hand, Comparative Examples 7-2 to 7-3 failed to obtain a good pattern such that pattern collapse was caused in the patterning process since the heat resistance was insufficient, the curing was insufficient in a nitrogen atmosphere as shown in Comparative Examples 1-2 to 1-3, and the pattern was not filled sufficiently. In Comparative Example 7-4, a cured film was formed to give solvent resistance, but pattern collapse occurred in the patterning process due to the ill gap filling of pattern, and accordingly, a favorable pattern could not be obtained finally.

As described above, it has become obvious that the inventive composition for forming an organic film containing the inventive compound shown by the general formula (1-1) brings excellent dry etching durability as well as heat resistance at a temperature of 400° C. or more and improved gap filling/planarizing characteristics even in an inert gas that does not contain oxygen, and accordingly, is very useful for composition for forming an organic film used for a multilayer resist process, and the patterning process using the same is capable of forming a fine pattern with highly accuracy even when the substrate to be processed is a patterned substrate.

It is to be noted that the present invention is not restricted to the foregoing embodiment. The embodiment is just an exemplification, and any examples that have substantially the same feature and demonstrate the same functions and effects as those in the technical concept described in claims of the present invention are included in the technical scope of the present invention.

The invention claimed is:

1. A compound having one of the structures shown by the following general formula (1-4),

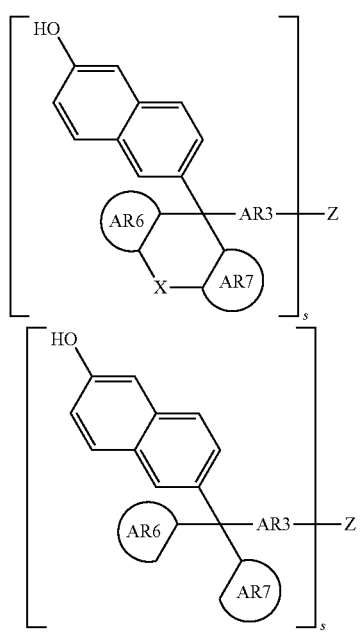

(1-4)

wherein:
AR3 represents a benzene ring, a thiophene ring, a pyridine ring, or a diazine ring optionally having a substituent;
AR6 and AR7 each represent a benzene ring, a thiophene ring, or a pyridine ring optionally having a substituent;
X represents a single bond or any of groups shown by the following formula (1-2-1');

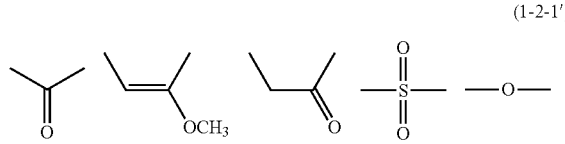

(1-2-1')

when X is a single bond, at least one of AR6 and AR7 is not a benzene ring;

"s" is 2 to 4; when s=2, Z represents a single bond, a divalent atom, or a divalent organic group, and when s=3 or 4, Z represents a trivalent or quadrivalent atom or organic group.

2. The compound according to claim 1, wherein when X is a single bond, at least one of AR6 and AR7 is a pyridine ring optionally having a substituent.

3. A compound having one of the structures shown by the following general formula (1-5),

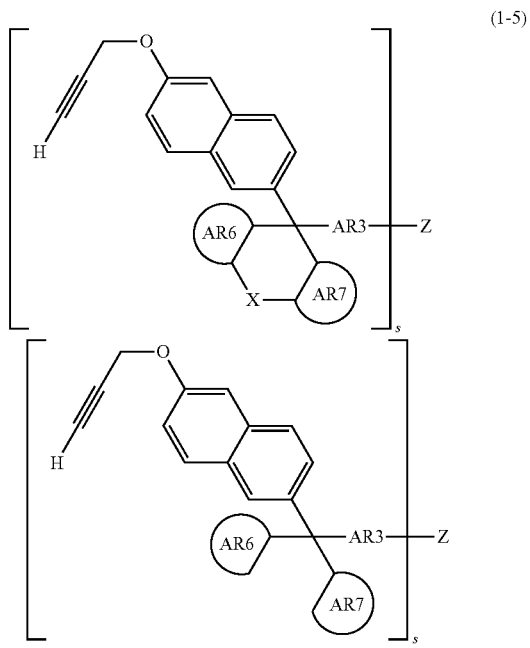

(1-5)

wherein:
AR3 represents a benzene ring, a thiophene ring, a pyridine ring, or a diazine ring optionally having a substituent;
AR6 and AR7 each represent a benzene ring, a thiophene ring, or a pyridine ring optionally having a substituent;
X represents a single bond or any of groups shown by the following formula (1-2-1');

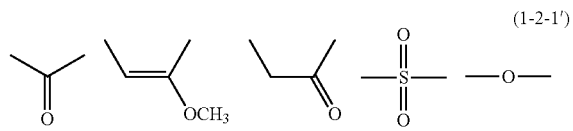

(1-2-1')

"s" is 2 to 4; when s=2, Z represents a single bond, a divalent atom, or a divalent organic group; and when s=3 or 4, Z represents a trivalent or quadrivalent atom or organic group, wherein and
when X is a single bond, at least one of AR6 and AR7 is a pyridine ring optionally having a substituent, and at least one of AR6 and AR7 is not a benzene ring.

* * * * *